US008535677B2

(12) United States Patent
Rohlff et al.

(10) Patent No.: US 8,535,677 B2
(45) Date of Patent: Sep. 17, 2013

(54) ANTIBODY DRUG CONJUGATE TREATMENT OF COLORECTAL CANCER

(75) Inventors: Christian Rohlff, Abingdon (GB); Jonathan Alexander Terrett, San Jose, CA (US)

(73) Assignee: Oxford Biotherapeutics, Ltd., Oxon (GB)

( * ) Notice: Subject to any disclaimer, the term of this patent is extended or adjusted under 35 U.S.C. 154(b) by 190 days.

(21) Appl. No.: 12/958,373

(22) Filed: Dec. 1, 2010

(65) Prior Publication Data
US 2011/0195026 A1 Aug. 11, 2011

Related U.S. Application Data

(63) Continuation-in-part of application No. 12/395,569, filed on Feb. 27, 2009, now abandoned, which is a continuation of application No. PCT/GB2007/050513, filed on Aug. 29, 2007, application No. 12/958,373, which is a continuation-in-part of application No. 12/329,500, filed on Dec. 5, 2008, now abandoned, which is a continuation of application No. PCT/EP2007/055537, filed on Jun. 5, 2007, application No. 12/958,373, which is a continuation-in-part of application No. PCT/US2010/031719, filed on Apr. 20, 2010.

(60) Provisional application No. 60/842,431, filed on Sep. 6, 2006, provisional application No. 60/811,681, filed on Jun. 7, 2006, provisional application No. 61/170,980, filed on Apr. 20, 2009.

(30) Foreign Application Priority Data

Jun. 6, 2006 (GB) .................................. 0611116.5
Aug. 29, 2006 (GB) .................................. 0616971.8

(51) Int. Cl.
*A61K 39/00* (2006.01)
(52) U.S. Cl.
USPC ...................................................... 424/178.1
(58) Field of Classification Search
None
See application file for complete search history.

(56) References Cited

U.S. PATENT DOCUMENTS

| 5,620,855 | A | 4/1997 | Dantzig et al. |
| 5,710,018 | A | 1/1998 | Dantzig et al. |
| 6,699,973 | B1 | 3/2004 | O'Mahony et al. |
| 6,703,362 | B1 | 3/2004 | Alvarez et al. |
| 7,053,177 | B1 | 5/2006 | Alvarez et al. |
| 7,135,457 | B1 | 11/2006 | Alvarez et al. |
| 2002/0076414 | A1* | 6/2002 | Xu et al. ................ 424/185.1 |

FOREIGN PATENT DOCUMENTS

| WO | 98/42736 | A | 10/1998 |
| WO | 01/49716 | A | 7/2001 |
| WO | 02/074156 | A | 9/2002 |
| WO | 02/083070 | A | 10/2002 |
| WO | 02/101357 | A | 12/2002 |
| WO | 03/020934 | A | 3/2003 |
| WO | 04/001072 | A | 12/2003 |
| WO | 2004/022778 | A | 3/2004 |
| WO | 2004/048529 | A | 6/2004 |
| WO | 2005/110338 | A | 11/2005 |
| WO | 2006/009805 | A | 1/2006 |
| WO | 2006/132971 | A | 12/2006 |
| WO | 2006/138275 | A | 12/2006 |
| WO | 2007/035676 | A | 3/2007 |
| WO | 2007/035690 | A | 3/2007 |
| WO | 2007/141280 | A | 6/2007 |

OTHER PUBLICATIONS

Stancovski et al (PNAS, 1991, 88:8691-8695).*
Reymond Ma, et al., "Expression and functional proteomics studies in colorectal cancer.", Pathol. Res. Pract., 2004, pp. 119-127, vol. 200, No. 2.
Ward DG, et al., "Identification of serum biomarkers for colon cancer by proteomic analysis.", British J. Cancer, 2006, pp. 1898-1905, vol. 94, No. 12.
Varghese S, et al., "Site-specific gene expression profiles and novel molecular prognostic factors in patients with lower gastrointestinal adenocarcinoma diffusely metastatic to liver or peritoneum." Ann. Surg. Oncol., 2007, pp. 3460-3471, vol. 14, No. 12.
Kwak JM, et al., "The prognostic significance of E-cadherin and liver intestine-cadherin expression in colorectal cancer.", Diseases of the Colon & Rectum, 2007, pp. 1873-1880, vol. 50, No. 11.
Kim HR, et al., "Comparative gene expression profiles of intestinal transporters in mice, rats and humans.", Pharmacol. Res., 2007, pp. 224-236, vol. 56, No. 3.
Holmes K, et al., "Genetic Mechanisms and Aberrant Gene Expression during the Development of Gastric Intestinal Metaplasia and Adenocarcinoma.", Curr. Genomics, 2007, pp. 379-397, vol. 8, No. 6.
Hilgendorf C, et al., "Expression of thirty-six drug transporter genes in human intestine, liver, kidney, and organotypic cell lines.", Drug Metab. Dispos., 2007, pp. 1333-1340, vol. 35, No. 8.
Wendeler MW, et al., "Intestinal L1-cadherin acts as a Ca2+-dependent adhesion switch.", J. Mol. Biol., 2007, pp. 220-230, vol. 370, No. 2.
Tian MM, et al., "Phenotypic classification of gastric signet ring cell carcinoma and its relationship with clinicopathologic parameters and prognosis.", World J. Gastroenterol., 2007, pp. 3189-3198, vol. 13, No. 23.
Chaturvedi P, et al., "MUC4 mucin potentiates pancreatic tumor cell proliferation, survival, and invasive properties and interferes with its interaction to extracellular matrix proteins.", Mol. Cancer Res., 2007, pp. 309-320, vol. 5, No. 4.
Dong W, et al., "Altered expression of a Li-cadherin in gastric cancer and intestinal metaplasia.", Dig. Dis. Sci., 2007, pp. 536-542, vol. 52, No. 2.
Park SS, et al., "Expression of liver-intestine cadherin and its correlation with lymph node metastasis in gastric cancer: can it predict N stage preoperatively?", Ann. Surg. Oncol., 2007, pp. 94-99, vol. 14, No. 1.
Kuhn A, et al. "Saccharide-induced peptide conformation in glycopeptides of the recognition region of L1-cadherin.", Angew. Chem. Int. Ed. Engl., 2007, pp. 454-458, vol. 46, No. 3.

(Continued)

*Primary Examiner* — Laura B Goddard
(74) *Attorney, Agent, or Firm* — Klauber & Jackson LLC

(57) ABSTRACT

The present invention provides methods and compositions for the treatment of and for screening, diagnosis and prognosis of colorectal cancer, for monitoring the effectiveness of colorectal cancer treatment, and for drug development.

3 Claims, 15 Drawing Sheets

(56) References Cited

OTHER PUBLICATIONS

Wang XQ, et al., "Liver intestine-cadherin (CDH17) haplotype is associated with increased risk of hepatocellular carcinoma.", Clin. Cancer Res., 2006, pp. 5248-5252, vol. 12, No. 17.

Heiner S, et al., "Hydrophilic photolabelling of glycopeptides from the murine liver-intestine (Ll) cadherin recognition domain.", Bioorg. Med. Chem., 2006, pp. 6149-6164, vol. 14, No. 18.

Wendeler MW, et al., "Unique gene structure and paralogy define the 7D-cadherin family.", Cell. Mol. Life Sci., 2006, pp. 1564-1573, vol. 63, No. 13.

Srebrow A, et al., "The connection between splicing and cancer.", J. Cell Sci., 2006, pp. 2635-2641, vol. 119.

Motoshita J, et al., "Molecular characteristics of differentiated-type gastric carcinoma with distinct mucin phenotype: Ll-cadherin is associated with intestinal phenotype.", Pathol. Int., 2006, pp. 200-205, vol. 56, No. 4.

Gendron FP, et al., "The CDX2 transcription factor regulates furin expression during intestinal epithelial cell differentiation.", Am. J. Physiol. Gastrointest. Liver Physiol., 2006, pp. G310-G318, vol. 290, No. 2.

Ito R, et al., "Clinicopathological significant and prognostic influence of cadherin-17 expression in gastric cancer.", Virchows Arch., 2005, pp. 717-722, vol. 447, No. 4.

Ko S, et al., "CDX2 co-localizes with liver-intestine cadherin in intestinal metaplasia and adenocarcinoma of the stomach.", J. Pathol., 2005, pp. 615-622, vol. 205, No. 5.

Ohnishi K, et al., "Lymphocyte-expressed BILL-cadherin/cadherin-17 contributes to the development of B cells at two stages.", Eur. J. Immunol., 2005, pp. 957-963, vol. 35, No. 3.

Yasui W, et al., "Molecular-pathological prognostic factors of gastric cancer: a review.", Gastric Cancer, 2005, pp. 86-94, vol. 8, No. 2.

Wang XQ, et al., "Alternative mRNA splicing of liver intestine-cadherin in hepatocellular carcinoma.", Clin. Cancer Res., 2005, pp. 483-489, vol. 11.

Takamura M, et al., "Reduced expression of liver-intestine cadherin is associated with progression and lymph node metastasis of human colorectal carcinoma.", Cancer Lett., 2004, pp. 253-259, vol. 212, No. 2.

Behrens I, et al., "Variation of peptide transporter (PepT1 and HPT1) expression in Caco-2 cells as a function of cell origin.", J. Pharm. Sci., 2004, pp. 1743-1754, vol. 93, No. 7.

Ouko L, et al., "Wnt11 signaling promotes proliferation, transformation, and migration of IEC6 intestinal epithelial cells.", J. Biol. Chem., 2004, pp. 26707-26715, vol. 279, No. 25.

Ko S, et al., "Overexpression of Ll-cadherin in gastric cancer is associated with lymph node metastasis.", Biochem. Biophys. Res. Commun., 2004, pp. 562-568, vol. 319, No. 2.

Jung R, et al., "Phylogenetic origin of Ll-cadherin revealed by protein and gene structure analysis.", Cell. Mol. Life Sci., 2004, pp. 1157-1166, vol. 61, No. 10.

Yasui W, et al., "Search for new biomarkers of gastric cancer through serial analysis of gene expression and its clinical implications.", Cancer Sci., 2004, pp. 385-392, vol. 95, No. 5.

Oue N, et al., "Gene expression profile of gastric carcinoma: identification of genes and tags potentially involved in invasion, metastasis, and carcinogenesis by serial analysis of gene expression.", Cancer Res., 2004, pp. 2397-2405, vol. 64.

Wendeler MW, et al., "Ksp-cadherin is a functional cell-cell adhesion molecule related to Ll-cadherin.", Exp. Cell Res., 2004, pp. 345-355, vol. 294, No. 2.

Danevad M, "Functional Analysis of the Murine Ll-Cadherin Promoter.", Doctoral Thesis, 2004, Germany.

Wagner M, et al., "The (2-phenyl-2-trimethylsilyl)ethyl-(PTMSEL)-linker in the synthesis of glycopeptide partial structures of complex cell surface glycoproteins.", Chemistry, 2003, pp. 6018-6030, vol. 9, No. 24.

Wong BW, et al., "Identification of liver-intestine cadherin in hepatocellular carcinoma-a potential disease marker.", Biochem. Biophys. Res. Commun., 2003, pp. 618-624, vol. 311, No. 3.

Behrens I, et al., "Do cell culture conditions influence the carrier-mediated transport of peptides in Caco-2 cell monolayers?", Eur. J. Pharm. Sci., 2003, pp. 433-442, vol. 19, No. 5.

Landowski CP, et al., "Gene expression in the human intestine and correlation with oral valacyclovir pharmacokinetic parameters.", J. Pharmacol. Exp. Ther., 2003, pp. 778-786, vol. 306, No. 2.

Takamura M, et al., "Expression of liver-intestine cadherin and its possible interaction with galectin-3 in ductal adenocarcinoma of the pancreas.", Cancer Sci., 2003, pp. 425-430, vol. 94, No. 5.

Hinoi T, et al., "CDX2 regulates liver intestine-cadherin expression in normal and malignant colon epithelium and intestinal metaplasia.", Gastroenterology, 2002, pp. 1565-1577, vol. 123, No. 5.

Horsfield J, et al., "Cadherin-17 is required to maintain pronephric duct integrity during zebrafish development.", Mech. Dev., 2002, pp. 15-26, vol. 115, Nos. 1-2.

Hippo Y, et al., "Global gene expression analysis of gastric cancer by oligonucleotide microarrays.", Cancer Res., 2002, pp. 233-240, vol. 62, No. 1.

Grotzinger C, et al., "Ll-cadherin: a marker of gastric metaplasia and neoplasia.", Gut, 2001, pp. 73-81, vol. 49, No. 1.

Rouzier R, et al., "The subtleties of intestinal metaplasia.", Gut, 2001, p. 8, vol. 49, No. 1.

Angres B, et al., "Ll-cadherin gene expression during mouse intestinal development.", Dev. Dyn., 2001, pp. 182-193, vol. 221, No. 2.

Herrera-Ruiz D, et al., "Spatial expression patterns of peptide transporters in the human and rat gastrointestinal tracts, Caco-2 in vitro cell culture model, and multiple human tissues.", AAPS PharmSci., 2001, pp. 100-111, vol. 3, No. 1.

Gessner R, et al., "Intestinal cell adhesion molecules. Liver-intestine cadherin.", Ann. N.Y. Acad. Sci., 2000, pp. 136-143, vol. 915.

Lucka L, et al., "Carcinoembryonic antigen-related cell-cell adhesion molecule C-CAM is greatly increased in serum and urine of rats with liver diseases.", FEBS Lett., 1998, pp. 37-40, vol. 438, Nos. 1-2.

Thomson RB, et al., "cDNA cloning and chromosomal localization of the human and mouse isoforms of Ksp-cadherin.", Genomics, 1998, pp. 445-451, vol. 51, No. 3.

Kremmidiotis G, et al., "Localization of human cadherin genes to chromosome regions exhibiting cancer-related loss of heterozygosity.", Genomics, 1998, pp. 467-471, vol. 49, No. 3.

Adibi SA, "The oligopeptide transporter (Pept-1) in human intestine: biology and function.", Gastroenterology, 1997, pp. 332-340, vol. 113, No. 1.

Reymond, et al., "Standardized Characterization of Gene Expression in Human Colorectal Epithelim by Two-Dimensional Electrophoresis." Electrophoresis, Wiley-VCH Verlag, Weinheim, DE, vol. 18, No. 15, Dec. 1997, pp. 2842-2848, XP002071492, ISSN: 017-0835.

Berndorff, et al., "Liver-Intestine Cadherin: Molecular Cloning and Characterization of a Novel Ca2+-dependent Cell Adhesion Molecule Expressed in Liver and Intestine," The Journal of Cell Biology, vol. 125, No. 6, Jun. 1994, pp. 1353-1369.

Kreft, et al., "LI-Cadherin-mediated Cell-Cell Adhesion Does Not Require Cytoplasmic Interactions," The Journal of Cell Biology, vol. 136, No. 5, Mar. 10, 1997, pp. 1109-1121.

* cited by examiner

Figure 1

CDH17 (SEQ ID No: 1)

Peptide Source: 1D-GEL, Colorectal Cancer

```
MILQAHLHSLCLLMLYLATGYGQEGKFSGPLKPMTFSIYEGQEPSQIIFQFKANPPAVTFELTGETDNI
FVIEREGLLYYNRALDRETRSTHNLQVAALDANGIIVEGPVPITIEVKDINDNRPTFLQSKYEGSVRQN
SRPGKPFLYVNATDLDDPATPNGQLYYQIVIQLPMINNVMYFQINNKTGAISLTREGSQELNPAKNPSY
NLVISVKDMGGQSENSFSDTTSVDIIVTENIWKAPKPVEMVENSTDPHPIKITQVRWNDPGAQYSLVDK
EKLPRFPFSIDQEGDIYVTQPLDREEKDAYVFYAVAKDEYGKPLSYPLEIHVKVKDINDNPPTCPSPVT
VFEVQENERLGNSIGTLTAHDRDEENTANSFLNYRIVEQTPKLPMDGLFLIQTYAGMLQLAKQSLKKQD
TPQYNLTIEVSDKDFKTLCFVQINVIDINDQIPIFEKSDYGNLTLAEDTNIGSTILTIQATDADEPFTG
SSKILYHIIKGDSEGRLGVDTDPHTNTGYVIIKKPLDFETAAVSNIVFKAENPEPLVFGVKYNASSFAK
FTLIVTDVNEAPQFSQHVFQAKVSEDVAIGTKVGNVTAKDPEGLDISYSLRGDTRGWLKIDHVTGEIFS
VAPLDREAGSPYRVQVVATEVGGSSLSSVSEFHLILMDVNDNPPRLAKDYTGLFFCHPLSAPGSLIFEA
TDDDQHLFRGPHFTFSLGSGSLQNDWEVSKINGTHARLSTRHTDFEERAYVVLIRINDGGRPPLEGIVS
LPVTFCSCVEGSCFRPAGHQTGIPTVGMAVGILLTTLLVIGIILAVVFIRIKKDKGKDNVESAQASEVK
PLRS
```

Mass Match Peptides (bold):
| | | |
|---|---|---|
| SEQID No.: 2 | AENPEPLVFGVK |
| SEQID No.: 4 | DEENTANSFLNYR |
| SEQID No.: 5 | DEYGKPLSYPLEIHVK |
| SEQID No.: 6 | DINDNRPTFLQSK |
| SEQID No.: 7 | DNVESAQASEVKPLR |
| SEQID No.:10 | IDHVTGEIFSVAPLDR |
| SEQID No.:13 | TGAISLTR |
| SEQID No.:16 | WNDPGAQYSLVDK |

Tandem Peptides (underline):
| | |
|---|---|
| SEQID No.: 2 | AENPEPLVFGVK |
| SEQID No.: 3 | DAYVFYAVAK |
| SEQID No.: 4 | DEENTANSFLNYR |
| SEQID No.: 7 | DNVESAQASEVKPLR |
| SEQID No.:16 | WNDPGAQYSLVDK |

Figure 2

CDH17 (SEQ ID No: 1)

Peptide Source: iTRAQ, Colorectal Cancer

```
MILQAHLHSLCLLMLYLATGYGQEGKFSGPLKPMTFSIYEGQEPSQIIFQFKANPPAVTFELTGETDNI
FVIEREGLLYYNRALDRETRSTHNLQVAALDANGIIVEGPVPITIEVKDINDNRPTFLQSKYEGSVRQN
SRPGKPFLYVNATDLDDPATPNGQLYYQIVIQLPMINNVMYFQINNKTGAISLTREGSQELNPAKNPSY
NLVISVKDMGGQSENSFSDTTSVDIIVTENIWKAPKPVEMVENSTDPHPIKITQVRWNDPGAQYSLVDK
EKLPRFPFSIDQEGDIYVTQPLDREEKDAYVFYAVAKDEYGKPLSYPLEIHVKVKDINDNPPTCPSPVT
VFEVQENERLGNSIGTLTAHDRDEENTANSFLNYRIVEQTPKLPMDGLFLIQTYAGMLQLAKQSLKKQD
TPQYNLTIEVSDKDFKTLCFVQINVIDINDQIPIFEKSDYGNLTLAEDTNIGSTILTIQATDADEPFTG
SSKILYHIIKGDSEGRLGVDTDPHTNTGYVIIKKPLDFETAAVSNIVFKAENPEPLVFGVKYNASSFAK
FTLIVTDVNEAPQFSQHVFQAKVSEDVAIGTKVGNVTAKDPEGLDISYSLRGDTRGWLKIDHVTGEIFS
VAPLDREAGSPYRVQVVATEVGGSSLSSVSEFHLILMDVNDNPPRLAKDYTGLFFCHPLSAPGSLIFEA
TDDDQHLFRGPHFTFSLGSGSLQNDWEVSKINGTHARLSTRHTDFEERAYVVLIRINDGGRPPLEGIVS
LPVTFCSCVEGSCFRPAGHQTGIPTVGMAVGILLTTLLVIGIILAVVFIRIKKDKGKDNVESAQASEVK
PLRS
```

Mass Match Peptides (bold):

| | | |
|---|---|---|
| SEQID No.: | 2 | AENPEPLVFGVK |
| SEQID No.: | 5 | DEYGKPLSYPLEIHVK |
| SEQID No.: | 8 | EGSQELNPAK |
| SEQID No.: | 9 | GWLK |
| SEQID No.: | 10 | IDHVTGEIFSVAPLDR |
| SEQID No.: | 11 | KPLDFETAAVSNIVFK |
| SEQID No.: | 12 | LGVDTDPHTNTGYVIIK |
| SEQID No.: | 14 | VKDINDNPPTCPSPVTVFEVQENER |
| SEQID No.: | 15 | VSEDVAIGTK |
| SEQID No.: | 17 | WNDPGAQYSLVDKEKLPR |

Tandem Peptides (underline):

| | | |
|---|---|---|
| SEQID No.: | 2 | AENPEPLVFGVK |
| SEQID No.: | 5 | DEYGKPLSYPLEIHVK |
| SEQID No.: | 8 | EGSQELNPAK |
| SEQID No.: | 9 | GWLK |
| SEQID No.: | 10 | IDHVTGEIFSVAPLDR |
| SEQID No.: | 11 | KPLDFETAAVSNIVFK |
| SEQID No.: | 12 | LGVDTDPHTNTGYVIIK |
| SEQID No.: | 14 | VKDINDNPPTCPSPVTVFEVQENER |
| SEQID No.: | 15 | VSEDVAIGTK |
| SEQID No.: | 17 | WNDPGAQYSLVDKEKLPR |

FACS: CDH17_A4 vs LoVo, LS 174T

SEQUENCE LISTING

```
<160> NUMBER OF SEQ ID NOS: 68

<210> SEQ ID NO 1
<211> LENGTH: 832
<212> TYPE: PRT
<213> ORGANISM: Homo sapiens

<400> SEQUENCE: 1

Met Ile Leu Gln Ala His Leu His Ser Leu Cys Leu Leu Met Leu Tyr
 1               5                  10                  15

Leu Ala Thr Gly Tyr Gly Gln Glu Gly Lys Phe Ser Gly Pro Leu Lys
            20                  25                  30

Pro Met Thr Phe Ser Ile Tyr Glu Gly Gln Glu Pro Ser Gln Ile Ile
        35                  40                  45

Phe Gln Phe Lys Ala Asn Pro Pro Ala Val Thr Phe Glu Leu Thr Gly
    50                  55                  60

Glu Thr Asp Asn Ile Phe Val Ile Glu Arg Glu Gly Leu Leu Tyr Tyr
65                  70                  75                  80

Asn Arg Ala Leu Asp Arg Glu Thr Arg Ser Thr His Asn Leu Gln Val
                85                  90                  95

Ala Ala Leu Asp Ala Asn Gly Ile Ile Val Glu Gly Pro Val Pro Ile
            100                 105                 110

Thr Ile Glu Val Lys Asp Ile Asn Asp Asn Arg Pro Thr Phe Leu Gln
        115                 120                 125

Ser Lys Tyr Glu Gly Ser Val Arg Gln Asn Ser Arg Pro Gly Lys Pro
    130                 135                 140

Phe Leu Tyr Val Asn Ala Thr Asp Leu Asp Asp Pro Ala Thr Pro Asn
145                 150                 155                 160

Gly Gln Leu Tyr Tyr Gln Ile Val Ile Gln Leu Pro Met Ile Asn Asn
                165                 170                 175

Val Met Tyr Phe Gln Ile Asn Asn Lys Thr Gly Ala Ile Ser Leu Thr
            180                 185                 190

Arg Glu Gly Ser Gln Glu Leu Asn Pro Ala Lys Asn Pro Ser Tyr Asn
        195                 200                 205

Leu Val Ile Ser Val Lys Asp Met Gly Gly Gln Ser Glu Asn Ser Phe
```

```
                    210                 215                 220
Ser Asp Thr Thr Ser Val Asp Ile Ile Val Thr Glu Asn Ile Trp Lys
225                 230                 235                 240

Ala Pro Lys Pro Val Glu Met Val Glu Asn Ser Thr Asp Pro His Pro
                245                 250                 255

Ile Lys Ile Thr Gln Val Arg Trp Asn Asp Pro Gly Ala Gln Tyr Ser
            260                 265                 270

Leu Val Asp Lys Glu Lys Leu Pro Arg Phe Pro Phe Ser Ile Asp Gln
        275                 280                 285

Glu Gly Asp Ile Tyr Val Thr Gln Pro Leu Asp Arg Glu Glu Lys Asp
    290                 295                 300

Ala Tyr Val Phe Tyr Ala Val Ala Lys Asp Glu Tyr Gly Lys Pro Leu
305                 310                 315                 320

Ser Tyr Pro Leu Glu Ile His Val Lys Val Lys Asp Ile Asn Asp Asn
                325                 330                 335

Pro Pro Thr Cys Pro Ser Pro Val Thr Val Phe Glu Val Gln Glu Asn
            340                 345                 350

Glu Arg Leu Gly Asn Ser Ile Gly Thr Leu Thr Ala His Asp Arg Asp
        355                 360                 365

Glu Glu Asn Thr Ala Asn Ser Phe Leu Asn Tyr Arg Ile Val Glu Gln
    370                 375                 380

Thr Pro Lys Leu Pro Met Asp Gly Leu Phe Leu Ile Gln Thr Tyr Ala
385                 390                 395                 400

Gly Met Leu Gln Leu Ala Lys Gln Ser Leu Lys Lys Gln Asp Thr Pro
                405                 410                 415

Gln Tyr Asn Leu Thr Ile Glu Val Ser Asp Lys Asp Phe Lys Thr Leu
            420                 425                 430

Cys Phe Val Gln Ile Asn Val Ile Asp Ile Asn Asp Gln Ile Pro Ile
        435                 440                 445

Phe Glu Lys Ser Asp Tyr Gly Asn Leu Thr Leu Ala Glu Asp Thr Asn
    450                 455                 460

Ile Gly Ser Thr Ile Leu Thr Ile Gln Ala Thr Asp Ala Asp Glu Pro
465                 470                 475                 480

Phe Thr Gly Ser Ser Lys Ile Leu Tyr His Ile Ile Lys Gly Asp Ser
                485                 490                 495

Glu Gly Arg Leu Gly Val Asp Thr Asp Pro His Thr Asn Thr Gly Tyr
            500                 505                 510

Val Ile Ile Lys Lys Pro Leu Asp Phe Glu Thr Ala Ala Val Ser Asn
        515                 520                 525

Ile Val Phe Lys Ala Glu Asn Pro Glu Pro Leu Val Phe Gly Val Lys
    530                 535                 540

Tyr Asn Ala Ser Ser Phe Ala Lys Phe Thr Leu Ile Val Thr Asp Val
545                 550                 555                 560

Asn Glu Ala Pro Gln Phe Ser Gln His Val Phe Gln Ala Lys Val Ser
                565                 570                 575

Glu Asp Val Ala Ile Gly Thr Lys Val Gly Asn Val Thr Ala Lys Asp
            580                 585                 590

Pro Glu Gly Leu Asp Ile Ser Tyr Ser Leu Arg Gly Asp Thr Arg Gly
        595                 600                 605

Trp Leu Lys Ile Asp His Val Thr Gly Glu Ile Phe Ser Val Ala Pro
    610                 615                 620

Leu Asp Arg Glu Ala Gly Ser Pro Tyr Arg Val Gln Val Val Ala Thr
625                 630                 635                 640
```

```
Glu Val Gly Gly Ser Ser Leu Ser Val Ser Glu Phe His Leu Ile
                645                 650                 655
Leu Met Asp Val Asn Asp Asn Pro Arg Leu Ala Lys Asp Tyr Thr
        660                 665                 670
Gly Leu Phe Phe Cys His Pro Leu Ser Ala Pro Gly Ser Leu Ile Phe
            675                 680                 685
Glu Ala Thr Asp Asp Gln His Leu Phe Arg Gly Pro His Phe Thr
    690                 695                 700
Phe Ser Leu Gly Ser Gly Ser Leu Gln Asn Asp Trp Glu Val Ser Lys
705                 710                 715                 720
Ile Asn Gly Thr His Ala Arg Leu Ser Thr Arg His Thr Asp Phe Glu
                725                 730                 735
Glu Arg Ala Tyr Val Val Leu Ile Arg Ile Asn Asp Gly Gly Arg Pro
                740                 745                 750
Pro Leu Glu Gly Ile Val Ser Leu Pro Val Thr Phe Cys Ser Cys Val
            755                 760                 765
Glu Gly Ser Cys Phe Arg Pro Ala Gly His Gln Thr Gly Ile Pro Thr
            770                 775                 780
Val Gly Met Ala Val Gly Ile Leu Leu Thr Thr Leu Leu Val Ile Gly
785                 790                 795                 800
Ile Ile Leu Ala Val Val Phe Ile Arg Ile Lys Lys Asp Lys Gly Lys
                805                 810                 815
Asp Asn Val Glu Ser Ala Gln Ala Ser Glu Val Lys Pro Leu Arg Ser
                820                 825                 830

<210> SEQ ID NO 2
<211> LENGTH: 12
<212> TYPE: PRT
<213> ORGANISM: Homo sapiens

<400> SEQUENCE: 2

Ala Glu Asn Pro Glu Pro Leu Val Phe Gly Val Lys
1               5                   10

<210> SEQ ID NO 3
<211> LENGTH: 10
<212> TYPE: PRT
<213> ORGANISM: Homo sapiens

<400> SEQUENCE: 3

Asp Ala Tyr Val Phe Tyr Ala Val Ala Lys
1               5                   10

<210> SEQ ID NO 4
<211> LENGTH: 13
<212> TYPE: PRT
<213> ORGANISM: Homo sapiens

<400> SEQUENCE: 4

Asp Glu Glu Asn Thr Ala Asn Ser Phe Leu Asn Tyr Arg
1               5                   10

<210> SEQ ID NO 5
<211> LENGTH: 16
<212> TYPE: PRT
<213> ORGANISM: Homo sapiens

<400> SEQUENCE: 5

Asp Glu Tyr Gly Lys Pro Leu Ser Tyr Pro Leu Glu Ile His Val Lys
1               5                   10                  15
```

```
<210> SEQ ID NO 6
<211> LENGTH: 13
<212> TYPE: PRT
<213> ORGANISM: Homo sapiens

<400> SEQUENCE: 6

Asp Ile Asn Asp Asn Arg Pro Thr Phe Leu Gln Ser Lys
1               5                   10

<210> SEQ ID NO 7
<211> LENGTH: 15
<212> TYPE: PRT
<213> ORGANISM: Homo sapiens

<400> SEQUENCE: 7

Asp Asn Val Glu Ser Ala Gln Ala Ser Glu Val Lys Pro Leu Arg
1               5                   10                  15

<210> SEQ ID NO 8
<211> LENGTH: 10
<212> TYPE: PRT
<213> ORGANISM: Homo sapiens

<400> SEQUENCE: 8

Glu Gly Ser Gln Glu Leu Asn Pro Ala Lys
1               5                   10

<210> SEQ ID NO 9
<211> LENGTH: 4
<212> TYPE: PRT
<213> ORGANISM: Homo sapiens

<400> SEQUENCE: 9

Gly Trp Leu Lys
1

<210> SEQ ID NO 10
<211> LENGTH: 16
<212> TYPE: PRT
<213> ORGANISM: Homo sapiens

<400> SEQUENCE: 10

Ile Asp His Val Thr Gly Glu Ile Phe Ser Val Ala Pro Leu Asp Arg
1               5                   10                  15

<210> SEQ ID NO 11
<211> LENGTH: 16
<212> TYPE: PRT
<213> ORGANISM: Homo sapiens

<400> SEQUENCE: 11

Lys Pro Leu Asp Phe Glu Thr Ala Ala Val Ser Asn Ile Val Phe Lys
1               5                   10                  15

<210> SEQ ID NO 12
<211> LENGTH: 17
<212> TYPE: PRT
<213> ORGANISM: Homo sapiens

<400> SEQUENCE: 12

Leu Gly Val Asp Thr Asp Pro His Thr Asn Thr Gly Tyr Val Ile Ile
1               5                   10                  15
Lys
```

```
<210> SEQ ID NO 13
<211> LENGTH: 8
<212> TYPE: PRT
<213> ORGANISM: Homo sapiens

<400> SEQUENCE: 13

Thr Gly Ala Ile Ser Leu Thr Arg
1               5

<210> SEQ ID NO 14
<211> LENGTH: 25
<212> TYPE: PRT
<213> ORGANISM: Homo sapiens

<400> SEQUENCE: 14

Val Lys Asp Ile Asn Asp Asn Pro Pro Thr Cys Pro Ser Pro Val Thr
1               5                   10                  15

Val Phe Glu Val Gln Glu Asn Glu Arg
            20                  25

<210> SEQ ID NO 15
<211> LENGTH: 10
<212> TYPE: PRT
<213> ORGANISM: Homo sapiens

<400> SEQUENCE: 15

Val Ser Glu Asp Val Ala Ile Gly Thr Lys
1               5                   10

<210> SEQ ID NO 16
<211> LENGTH: 13
<212> TYPE: PRT
<213> ORGANISM: Homo sapiens

<400> SEQUENCE: 16

Trp Asn Asp Pro Gly Ala Gln Tyr Ser Leu Val Asp Lys
1               5                   10

<210> SEQ ID NO 17
<211> LENGTH: 18
<212> TYPE: PRT
<213> ORGANISM: Homo sapiens

<400> SEQUENCE: 17

Trp Asn Asp Pro Gly Ala Gln Tyr Ser Leu Val Asp Lys Glu Lys Leu
1               5                   10                  15

Pro Arg

<210> SEQ ID NO 18
<211> LENGTH: 260
<212> TYPE: PRT
<213> ORGANISM: Mus musculus

<400> SEQUENCE: 18

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
            20                  25                  30

Pro Val Ala Lys Ala Glu Val Gln Leu Leu Glu Thr Gly Gly Val
        35                  40                  45

Val Lys Pro Gly Gly Ser Leu Lys Leu Ser Cys Ala Ala Ser Gly Phe
    50                  55                  60

Thr Phe Ser Asn Tyr Gly Met Ser Trp Val Arg Gln Thr Pro Glu Lys
```

```
                65                  70                  75                  80
Arg Leu Glu Trp Val Ala Ala Ile Asn Arg Asp Gly Gly Thr Thr Tyr
                    85                  90                  95

Tyr Thr Asp Asn Val Lys Gly Arg Phe Thr Ile Ser Arg Asp Asn Ala
                100                 105                 110

Lys Asn Ser Leu Tyr Leu Gln Met Ser Ser Leu Arg Ser Glu Asp Thr
                115                 120                 125

Ala Leu Tyr Tyr Cys Ala Arg Gln Phe Leu Leu Trp Asp Gly Trp Tyr
            130                 135                 140

Phe Asp Val Trp Gly Ala Gly Thr Thr Val Thr Val Ser Ser Ala Lys
145                 150                 155                 160

Thr Thr Pro Pro Ser Val Tyr Pro Leu Ala Pro Gly Ser Ala Ala Gln
                165                 170                 175

Thr Asn Ser Met Val Thr Leu Gly Cys Leu Val Lys Gly Tyr Phe Pro
            180                 185                 190

Glu Pro Val Thr Val Thr Trp Asn Ser Gly Ser Leu Ser Ser Gly Val
                195                 200                 205

His Thr Phe Pro Ala Val Leu Gln Ser Asp Leu Tyr Thr Leu Ser Ser
        210                 215                 220

Ser Val Thr Val Pro Ser Ser Thr Trp Pro Ser Glu Thr Val Thr Cys
225                 230                 235                 240

Asn Val Ala His Pro Ala Ser Ser Thr Lys Val Asp Lys Lys Ile Val
                245                 250                 255

Pro Arg Asp Cys
            260

<210> SEQ ID NO 19
<211> LENGTH: 258
<212> TYPE: PRT
<213> ORGANISM: Mus musculus

<400> SEQUENCE: 19

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
                20                  25                  30

Pro Val Ala Lys Ala Gln Val Gln Leu Gln Gln Ser Asp Ala Glu Leu
            35                  40                  45

Val Lys Pro Gly Ala Ser Val Lys Ile Ser Cys Lys Val Ser Gly Tyr
        50                  55                  60

Thr Phe Ser Asp His Ala Ile His Trp Met Ser Gln Arg Pro Gly Gln
65                  70                  75                  80

Gly Leu Lys Trp Ile Gly Tyr Ile Tyr Pro Arg His Gly Thr Thr Asn
                85                  90                  95

Tyr Asn Glu Asn Phe Lys Gly Lys Ala Thr Leu Thr Ala Asp Thr Ser
                100                 105                 110

Ser Ser Thr Ala Tyr Met Gln Leu Asn Ser Leu Thr Ser Glu Asp Ser
            115                 120                 125

Ala Val Tyr Phe Cys Ala Arg Met Arg Asn Tyr Phe Tyr Val Met Asp
        130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
```

```
                          180                 185                 190
Val Thr Val Thr Trp Asn Ser Gly Ser Leu Ser Ser Gly Val His Thr
            195                 200                 205

Phe Pro Ala Val Leu Gln Ser Asp Leu Tyr Thr Leu Ser Ser Ser Val
        210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 20
<211> LENGTH: 258
<212> TYPE: PRT
<213> ORGANISM: Mus musculus

<400> SEQUENCE: 20

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
            20                  25                  30

Pro Val Ala Lys Ala Gln Val Leu Leu Gln Gln Ser Asp Ala Glu Leu
        35                  40                  45

Val Lys Pro Gly Ala Ser Val Lys Ile Ser Cys Lys Ala Ser Gly Tyr
    50                  55                  60

Thr Phe Thr Asp His Ala Ile His Trp Val Lys Gln Arg Pro Glu Gln
65                  70                  75                  80

Gly Leu Glu Trp Ile Gly Tyr Ile Tyr Pro Glu His Gly Thr Ile Lys
                85                  90                  95

Tyr Asn Glu Lys Phe Lys Gly Lys Ala Thr Leu Thr Ala Asp Lys Ser
            100                 105                 110

Ser Ser Thr Ala Tyr Met Gln Leu Asn Ser Leu Thr Ser Glu Asp Ser
        115                 120                 125

Ala Val Tyr Phe Cys Ser Arg Leu Thr Asn Tyr Phe Tyr Val Met Glu
    130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 21
<211> LENGTH: 262
<212> TYPE: PRT
<213> ORGANISM: Mus musculus
```

-continued

```
<400> SEQUENCE: 21

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Glu Val Gln Leu Gln Gln Ser Val Ala Glu Leu
        35                  40                  45

Val Lys Pro Gly Ala Ser Val Lys Met Ser Cys Lys Val Ser Gly Tyr
    50                  55                  60

Thr Leu Thr Asp His Thr Ile His Trp Met Lys Gln Arg Pro Glu Gln
65                  70                  75                  80

Gly Leu Glu Trp Ile Gly Tyr Ile Tyr Pro Arg Asp Gly Ile Thr Gly
                85                  90                  95

Tyr Asn Glu Lys Phe Lys Gly Lys Ala Thr Leu Thr Ala Asp Thr Ser
            100                 105                 110

Ser Ser Thr Ala Tyr Met Gln Leu Asn Ser Leu Thr Ser Glu Asp Ser
        115                 120                 125

Ala Val Tyr Phe Cys Ala Arg Trp Gly Tyr Ser Tyr Arg Asn Tyr Ala
    130                 135                 140

Tyr Tyr Tyr Asp Tyr Trp Gly Gln Gly Thr Thr Leu Thr Val Ser Ser
145                 150                 155                 160

Ala Lys Thr Thr Pro Pro Ser Val Tyr Pro Leu Ala Pro Gly Ser Ala
                165                 170                 175

Ala Gln Thr Asn Ser Met Val Thr Leu Gly Cys Leu Val Lys Gly Tyr
            180                 185                 190

Phe Pro Glu Pro Val Thr Val Thr Trp Asn Ser Gly Ser Leu Ser Ser
        195                 200                 205

Gly Val His Thr Phe Pro Ala Val Leu Gln Ser Asp Leu Tyr Thr Leu
    210                 215                 220

Ser Ser Ser Val Thr Val Pro Ser Ser Thr Trp Pro Ser Glu Thr Val
225                 230                 235                 240

Thr Cys Asn Val Ala His Pro Ala Ser Ser Thr Lys Val Asp Lys Lys
                245                 250                 255

Ile Val Pro Arg Asp Cys
            260

<210> SEQ ID NO 22
<211> LENGTH: 258
<212> TYPE: PRT
<213> ORGANISM: Mus musculus

<400> SEQUENCE: 22

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Asp Ala Asp Leu
        35                  40                  45

Val Lys Pro Gly Ala Ser Val Lys Ile Ser Cys Lys Ala Ser Gly Tyr
    50                  55                  60

Thr Phe Thr Asp His Ala Ile His Trp Val Lys Gln Arg Pro Glu Gln
65                  70                  75                  80

Gly Leu Glu Trp Ile Gly Tyr Ile Tyr Pro Glu His Gly Thr Ile Lys
                85                  90                  95

Tyr Asn Glu Lys Phe Lys Gly Lys Ala Thr Leu Thr Ala Asp Lys Ser
```

```
                    100                 105                 110
Ser Ser Thr Ala Tyr Met Gln Leu Asn Ser Leu Thr Ser Glu Asp Ser
            115                 120                 125

Ala Val Tyr Phe Cys Ala Arg Leu Arg Asn Tyr Leu Tyr Ile Met Asp
            130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
            165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
            195                 200                 205

Phe Pro Ala Val Leu Gln Ser Asp Leu Tyr Thr Leu Ser Ser Ser Val
            210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
            245                 250                 255

Asp Cys

<210> SEQ ID NO 23
<211> LENGTH: 258
<212> TYPE: PRT
<213> ORGANISM: Mus musculus

<400> SEQUENCE: 23

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Asp Ala Glu Leu
            35                  40                  45

Val Lys Pro Gly Ala Ser Val Lys Ile Ser Cys Lys Ala Ser Gly Tyr
50                  55                  60

Thr Phe Thr Asp His Ala Ile His Trp Val Lys Gln Arg Pro Glu Gln
65                  70                  75                  80

Gly Leu Glu Trp Ile Gly Tyr Ile Tyr Pro Glu His Gly Thr Ile Lys
            85                  90                  95

Tyr Asn Glu Lys Phe Lys Gly Lys Ala Thr Leu Thr Ala Asp Lys Ser
            100                 105                 110

Ser Ser Thr Ala Tyr Met Gln Leu Asn Ser Leu Thr Ser Glu Asp Ser
            115                 120                 125

Ala Val Tyr Phe Cys Ser Arg Leu Thr Asn Tyr Phe Tyr Val Met Glu
            130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
            165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
            195                 200                 205

Phe Pro Ala Val Leu Gln Ser Asp Leu Tyr Thr Leu Ser Ser Ser Val
            210                 215                 220
```

```
Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys
```

<210> SEQ ID NO 24
<211> LENGTH: 258
<212> TYPE: PRT
<213> ORGANISM: Mus musculus

<400> SEQUENCE: 24

```
Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
                20                  25                  30

Pro Val Ala Lys Ala Gln Val Gln Leu Gln Gln Ser Asp Ala Glu Leu
            35                  40                  45

Val Lys Pro Gly Ala Ser Val Lys Ile Ser Cys Lys Val Ser Gly Tyr
50                  55                  60

Thr Phe Thr Asp His Ala Ile His Trp Met Lys Gln Arg Pro Glu Gln
65                  70                  75                  80

Gly Leu Glu Trp Ile Gly Tyr Ile Tyr Pro Arg Asp Gly Phe Thr Lys
                85                  90                  95

Tyr Asn Glu Lys Phe Lys Gly Lys Ala Thr Leu Thr Ala Asp Thr Ser
            100                 105                 110

Ser Ser Thr Ala Tyr Met Gln Leu Asn Ser Leu Thr Ser Glu Asp Ser
        115                 120                 125

Thr Val Tyr Phe Cys Ala Arg Met Thr Asn Tyr Phe Tyr Thr Met Asp
130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys
```

<210> SEQ ID NO 25
<211> LENGTH: 258
<212> TYPE: PRT
<213> ORGANISM: Mus musculus

<400> SEQUENCE: 25

```
Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
                20                  25                  30
```

```
Pro Val Ala Lys Ala Gln Val Gln Leu Gln Gln Ser Asp Ala Asp Leu
            35                  40                  45

Val Lys Pro Gly Ala Ser Val Lys Ile Ser Cys Lys Ala Ser Gly Tyr
 50                  55                  60

Thr Phe Thr Asp His Ala Ile His Trp Val Lys Gln Arg Pro Glu Gln
 65                  70                  75                  80

Gly Leu Glu Trp Ile Gly Tyr Ile Tyr Pro Glu His Gly Thr Ile Lys
                 85                  90                  95

Tyr Asn Glu Lys Phe Lys Gly Lys Ala Thr Leu Thr Ala Asp Lys Ser
            100                 105                 110

Ser Ser Thr Ala Tyr Met Gln Leu Asn Ser Leu Thr Ser Glu Asp Ser
            115                 120                 125

Ala Val Tyr Phe Cys Ser Arg Leu Thr Asn Tyr Phe Tyr Val Met Glu
130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
            195                 200                 205

Phe Pro Ala Val Leu Gln Ser Asp Leu Tyr Thr Leu Ser Ser Ser Val
210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 26
<211> LENGTH: 258
<212> TYPE: PRT
<213> ORGANISM: Mus musculus

<400> SEQUENCE: 26

Leu Gly Lys Pro Trp Arg Tyr Pro Arg Phe Val His Gly Glu Asn Lys
1               5                  10                  15

Val Lys Gln Ser Thr Ile Ala Leu Ala Leu Leu Pro Leu Leu Phe Thr
             20                  25                  30

Pro Val Ala Lys Ala Gln Val Gln Leu Gln Gln Ser Asp Ala Glu Leu
            35                  40                  45

Val Lys Pro Gly Ala Ser Val Lys Ile Ser Cys Lys Ala Ser Gly Tyr
 50                  55                  60

Thr Phe Thr Asp His Ala Ile His Trp Val Lys Gln Arg Pro Glu Gln
 65                  70                  75                  80

Gly Leu Glu Trp Ile Gly Tyr Ile Tyr Pro Glu His Gly Ser Ile Thr
                 85                  90                  95

Tyr Asn Glu Lys Phe Lys Gly Lys Ala Thr Leu Thr Ala Asp Lys Ser
            100                 105                 110

Ser Ser Thr Val Tyr Met His Leu Asn Ser Leu Thr Ser Glu Asp Ser
            115                 120                 125

Ala Val Tyr Phe Cys Ala Arg Leu Arg Asn Tyr Leu Tyr Val Met Asp
130                 135                 140
```

```
Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 27
<211> LENGTH: 258
<212> TYPE: PRT
<213> ORGANISM: Mus musculus

<400> SEQUENCE: 27

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Glu Ala Glu Leu
        35                  40                  45

Val Lys Pro Gly Ala Ser Val Lys Leu Ser Cys Lys Ala Ser Gly Tyr
    50                  55                  60

Thr Phe Thr Asp His Ala Ile His Trp Met Lys Gln Arg Pro Glu Gln
65                  70                  75                  80

Gly Leu Glu Trp Ile Gly Tyr Ile Tyr Pro Arg Asp Asp Phe Ala Lys
                85                  90                  95

Val Asn Glu Lys Phe Lys Gly Lys Ala Thr Leu Thr Ala Asp Thr Ser
            100                 105                 110

Ser Ser Thr Ala Tyr Met Gln Leu Asn Ser Leu Thr Ser Glu Asp Ser
        115                 120                 125

Ala Val Tyr Phe Cys Ala Arg Met Thr Asn Tyr Leu Tyr Ile Met Asp
130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys
```

<210> SEQ ID NO 28
<211> LENGTH: 258
<212> TYPE: PRT
<213> ORGANISM: Mus musculus

<400> SEQUENCE: 28

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Asp Ala Glu Leu
        35                  40                  45

Val Lys Pro Gly Ala Ser Val Lys Ile Ser Cys Lys Ala Ser Gly Tyr
    50                  55                  60

Thr Phe Thr Asp His Ala Ile His Trp Val Lys Gln Arg Pro Glu Gln
65                  70                  75                  80

Gly Leu Glu Trp Ile Gly Tyr Ile Tyr Pro Glu His Gly Thr Ile Thr
                85                  90                  95

Tyr Asn Glu Lys Phe Lys Gly Lys Ala Thr Leu Thr Ala Asp Lys Ser
            100                 105                 110

Ser Ser Thr Val Tyr Met His Leu Asn Ser Leu Thr Ser Glu Asp Ser
        115                 120                 125

Ala Val Tyr Phe Cys Ala Arg Leu Arg Asn Tyr Leu Tyr Ile Met Asp
    130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 29
<211> LENGTH: 258
<212> TYPE: PRT
<213> ORGANISM: Mus musculus

<400> SEQUENCE: 29

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Asp Ala Ala Leu
        35                  40                  45

Val Lys Pro Gly Ala Ser Val Lys Ile Ser Cys Lys Val Ser Gly Tyr
    50                  55                  60

Thr Phe Ser Asp His Ala Ile His Trp Met Lys Gln Arg Pro Glu Gln

```
                65                  70                  75                  80
Gly Leu Glu Trp Ile Gly Tyr Ile Phe Pro Arg Asp Ala Phe Ser Leu
                    85                  90                  95

Asn Asn Glu Lys Phe Lys Gly Lys Ala Thr Leu Ser Ala Asp Thr Ser
                100                 105                 110

Ser Ser Thr Ala Tyr Met Glu Leu Thr Ser Leu Thr Phe Glu Asp Ser
            115                 120                 125

Ala Val Tyr Phe Cys Ala Arg Met Arg Asn Tyr Phe Tyr Val Met Asp
        130                 135                 140

Tyr Trp Gly Gln Gly Thr Ser Val Thr Val Ser Ser Ala Lys Thr Thr
145                 150                 155                 160

Pro Pro Ser Val Tyr Thr Leu Ala Pro Gly Ser Ala Ala Gln Thr Asn
                165                 170                 175

Ser Met Val Thr Leu Gly Cys Leu Val Lys Gly Tyr Phe Pro Glu Pro
                180                 185                 190

Val Thr Val Thr Trp Asn Ser Gly Ser Leu Ser Ser Gly Val His Thr
                195                 200                 205

Phe Pro Ala Val Leu Gln Ser Asp Leu Tyr Thr Leu Ser Ser Ser Val
210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 30
<211> LENGTH: 275
<212> TYPE: PRT
<213> ORGANISM: Mus musculus

<400> SEQUENCE: 30

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
                20                  25                  30

Ala Ala Ala Gly Leu Leu Leu Ala Ala Gln Pro Ala Met Ala Asp
            35                  40                  45

Val Val Leu Thr Gln Thr Pro Leu Ser Leu Pro Val Thr Leu Gly Asp
        50                  55                  60

Gln Ala Ser Ile Ser Cys Arg Ser Ser Gln Ser Leu Leu His Ser Asn
65                  70                  75                  80

Gly Asn Thr Tyr Leu His Trp Tyr Leu Leu Lys Pro Gly Gln Ser Pro
                85                  90                  95

Lys Leu Leu Ile Tyr Lys Val Ser Asn Arg Phe Ser Gly Val Pro Asp
                100                 105                 110

Arg Phe Ser Gly Ser Gly Ser Gly Thr Asp Phe Thr Leu Lys Ile Thr
            115                 120                 125

Arg Val Glu Ala Glu Asp Leu Gly Val Tyr Phe Cys Ser Gln Ser Thr
        130                 135                 140

His Val Leu Thr Phe Gly Ala Gly Thr Lys Leu Glu Leu Lys Arg Ala
145                 150                 155                 160

Asp Ala Ala Pro Thr Val Ser Ile Phe Pro Pro Ser Ser Glu Gln Leu
                165                 170                 175

Thr Ser Gly Gly Ala Ser Val Val Cys Phe Leu Asn Asn Phe Tyr Pro
                180                 185                 190
```

```
Lys Asp Ile Asn Val Lys Trp Lys Ile Asp Gly Ser Glu Arg Gln Asn
            195                 200                 205
Gly Val Leu Asn Ser Trp Thr Asp Gln Asp Ser Lys Asp Ser Thr Tyr
        210                 215                 220
Ser Met Ser Ser Thr Leu Thr Leu Thr Lys Asp Glu Tyr Glu Arg His
225                 230                 235                 240
Asn Ser Tyr Thr Cys Glu Ala Thr His Lys Thr Ser Thr Ser Pro Ile
                245                 250                 255
Val Lys Ser Phe Asn Arg Asn Glu Ser Tyr Pro Tyr Asp Val Pro Asp
            260                 265                 270
Tyr Ala Ser
    275

<210> SEQ ID NO 31
<211> LENGTH: 276
<212> TYPE: PRT
<213> ORGANISM: Mus musculus

<400> SEQUENCE: 31

Arg Ile Leu Pro Asp Ala Phe Tyr Arg Asn Ser Leu Leu Phe Leu His
1               5                   10                  15
Thr Arg Phe Phe Gly Trp Ser Glu Thr Met Lys Tyr Leu Leu Pro Thr
            20                  25                  30
Ala Ala Ala Gly Leu Leu Leu Ala Ala Gln Pro Ala Met Ala Asp
        35                  40                  45
Ile Val Met Thr Gln Ala Ala Pro Ser Val Pro Val Thr Pro Gly Glu
    50                  55                  60
Ser Val Ser Ile Ser Cys Thr Ser Ser Lys Ser Leu Leu Arg Ser Asn
65                  70                  75                  80
Gly Asn Thr Tyr Leu Tyr Trp Phe Leu Gln Arg Pro Gly Gln Ser Pro
                85                  90                  95
Gln Leu Leu Ile Tyr Arg Met Ser Asn Leu Ala Ser Gly Val Pro Asp
            100                 105                 110
Arg Phe Ser Gly Ser Gly Ser Gly Thr Ala Phe Thr Leu Arg Ile Ser
        115                 120                 125
Arg Val Glu Ala Glu Asp Val Gly Val Tyr Tyr Cys Met Gln His Leu
    130                 135                 140
Glu Tyr Pro Phe Thr Phe Gly Ser Gly Thr Lys Leu Glu Ile Lys Arg
145                 150                 155                 160
Ala Asp Ala Ala Pro Thr Val Ser Ile Phe Pro Pro Ser Ser Glu Gln
                165                 170                 175
Leu Thr Ser Gly Gly Ala Ser Val Val Cys Phe Leu Asn Asn Phe Tyr
            180                 185                 190
Pro Lys Asp Ile Asn Val Lys Trp Lys Ile Asp Gly Ser Glu Arg Gln
        195                 200                 205
Asn Gly Val Leu Asn Ser Trp Thr Asp Gln Asp Ser Lys Asp Ser Thr
    210                 215                 220
Tyr Ser Met Ser Ser Thr Leu Thr Leu Thr Lys Asp Glu Tyr Glu Arg
225                 230                 235                 240
His Asn Ser Tyr Thr Cys Glu Ala Thr His Lys Thr Ser Thr Ser Pro
                245                 250                 255
Ile Val Lys Ser Phe Asn Arg Asn Glu Ser Tyr Pro Tyr Asp Val Pro
            260                 265                 270
Asp Tyr Ala Ser
        275
```

```
<210> SEQ ID NO 32
<211> LENGTH: 277
<212> TYPE: PRT
<213> ORGANISM: Mus musculus

<400> SEQUENCE: 32

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45

Ile Val Met Ser Gln Ser Pro Ser Ser Leu Ala Val Ser Val Gly Glu
    50                  55                  60

Lys Val Thr Met Ser Cys Lys Ser Ser Gln Ser Leu Leu His Ser Ser
65                  70                  75                  80

Asn Gln Lys Asn Tyr Leu Ala Trp Tyr Gln Gln Lys Pro Gly Gln Ser
                85                  90                  95

Pro Lys Val Leu Ile Tyr Trp Ala Ser Thr Arg Glu Ser Gly Val Pro
            100                 105                 110

Asp Arg Phe Thr Gly Ser Gly Ser Gly Thr Asp Phe Thr Leu Thr Ile
        115                 120                 125

Thr Ser Val Lys Ser Glu Asp Leu Ala Val Tyr Tyr Cys Gln Gln Tyr
130                 135                 140

Tyr Ser Tyr Pro Trp Thr Phe Gly Gly Gly Thr Arg Leu Glu Ile Lys
145                 150                 155                 160

Arg Ala Asp Ala Ala Pro Thr Val Ser Ile Phe Pro Pro Ser Ser Glu
                165                 170                 175

Gln Leu Thr Ser Gly Gly Ala Ser Val Val Cys Phe Leu Asn Asn Phe
            180                 185                 190

Tyr Pro Lys Asp Ile Asn Val Lys Trp Lys Ile Asp Gly Ser Glu Arg
        195                 200                 205

Gln Asn Gly Val Leu Asn Ser Trp Thr Asp Gln Asp Ser Lys Asp Ser
    210                 215                 220

Thr Tyr Ser Met Ser Ser Thr Leu Thr Leu Thr Lys Asp Glu Tyr Glu
225                 230                 235                 240

Arg His Asn Ser Tyr Thr Cys Glu Ala Thr His Lys Thr Ser Thr Ser
                245                 250                 255

Pro Ile Val Lys Ser Phe Asn Arg Asn Glu Ser Tyr Pro Tyr Asp Val
            260                 265                 270

Pro Asp Tyr Ala Ser
        275

<210> SEQ ID NO 33
<211> LENGTH: 276
<212> TYPE: PRT
<213> ORGANISM: Mus musculus

<400> SEQUENCE: 33

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45
```

Ile Val Met Thr Gln Ala Ala Pro Ser Val Pro Val Thr Pro Gly Glu
            50                  55                  60

Ser Val Ser Ile Ser Cys Arg Ser Ser Lys Ser Leu Leu Arg Ser Asn
 65                  70                  75                  80

Gly Asn Thr Tyr Leu Tyr Trp Phe Leu Gln Arg Pro Gly Gln Ser Pro
                 85                  90                  95

Gln Leu Leu Ile Tyr Arg Leu Ser Asn Leu Ala Ser Gly Val Pro Asp
            100                 105                 110

Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
        130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
            195                 200                 205

Asn Gly Val Leu Asn Ser Trp Thr Asp Gln Asp Ser Lys Asp Ser Thr
        210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
            260                 265                 270

Asp Tyr Ala Ser
        275

<210> SEQ ID NO 34
<211> LENGTH: 276
<212> TYPE: PRT
<213> ORGANISM: Mus musculus

<400> SEQUENCE: 34

Arg Ile Leu Pro Asp Ala Phe Tyr Arg Asn Ser Leu Leu Phe Leu His
 1               5                  10                  15

Thr Arg Phe Phe Gly Trp Ser Glu Thr Ile Lys Tyr Leu Leu Pro Thr
                20                  25                  30

Ala Ala Ala Gly Leu Leu Leu Ala Ala Gln Pro Ala Met Ala Asp
            35                  40                  45

Ile Val Met Thr Gln Ala Ala Pro Ser Val Pro Val Thr Pro Gly Glu
            50                  55                  60

Ser Val Ser Ile Ser Cys Thr Ser Ser Lys Ser Leu Leu Arg Ser Asn
 65                  70                  75                  80

Gly Asn Thr Tyr Leu Tyr Trp Phe Leu Gln Arg Pro Gly Gln Ser Pro
                 85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
        130                 135                 140

```
Glu Tyr Pro Phe Thr Phe Gly Ser Gly Thr Lys Leu Glu Ile Lys Arg
145                 150                 155                 160

Ala Asp Ala Ala Pro Thr Val Ser Ile Leu Pro Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
        195                 200                 205

Asn Gly Val Leu Asn Ser Trp Thr Asp Gln Asp Ser Lys Asp Ser Thr
    210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
            260                 265                 270

Asp Tyr Ala Ser
        275

<210> SEQ ID NO 35
<211> LENGTH: 276
<212> TYPE: PRT
<213> ORGANISM: Mus musculus

<400> SEQUENCE: 35

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
                20                  25                  30

Ala Ala Ala Gly Leu Leu Leu Ala Ala Gln Pro Ala Met Ala Asp
            35                  40                  45

Ile Val Met Thr Gln Ala Ala Pro Ser Val Pro Val Thr Pro Gly Glu
        50                  55                  60

Ser Val Ser Ile Ser Cys Arg Ser Ser Lys Ser Leu Leu Arg Thr Asn
65                  70                  75                  80

Gly Asn Thr Tyr Leu His Trp Phe Leu Gln Arg Pro Gly Gln Ser Pro
                85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Val Phe Thr Leu Arg Ile Ser
        115                 120                 125

Arg Val Glu Ala Glu Asp Val Gly Val Tyr Tyr Cys Met Gln His Leu
    130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
        195                 200                 205

Asn Gly Val Leu Asn Ser Trp Thr Asp Gln Asp Ser Lys Asp Ser Thr
    210                 215                 220

Tyr Ser Met Ser Ser Thr Leu Thr Leu Thr Lys Asp Glu Tyr Glu Arg
225                 230                 235                 240
```

His Asn Ser Tyr Thr Cys Glu Ala Thr His Lys Thr Ser Thr Ser Pro
            245                 250                 255

Ile Val Lys Ser Phe Asn Arg Asn Glu Ser Tyr Pro Tyr Asp Val Pro
            260                 265                 270

Asp Tyr Ala Ser
            275

<210> SEQ ID NO 36
<211> LENGTH: 276
<212> TYPE: PRT
<213> ORGANISM: Mus musculus

<400> SEQUENCE: 36

Arg Ile Leu Pro Tyr Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
            35                  40                  45

Ile Val Met Thr Gln Ala Ala Pro Ser Val Pro Val Thr Pro Gly Glu
50                  55                  60

Ser Val Ser Ile Ser Cys Arg Ser Ser Lys Ser Leu Leu Arg Ser Asn
65                  70                  75                  80

Gly Asn Thr Tyr Leu Tyr Trp Phe Leu Gln Arg Pro Gly Gln Ser Pro
                85                  90                  95

Gln Leu Leu Ile Tyr Arg Leu Ser Asn Leu Ala Ser Gly Val Pro Asp
            100                 105                 110

Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
            195                 200                 205

Asn Gly Val Leu Asn Ser Trp Thr Asp Gln Asp Ser Lys Asp Ser Thr
210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
            260                 265                 270

Asp Tyr Ala Ser
            275

<210> SEQ ID NO 37
<211> LENGTH: 276
<212> TYPE: PRT
<213> ORGANISM: Mus musculus

<400> SEQUENCE: 37

Arg Ile Leu Pro Asp Ala Phe Tyr Arg Asn Ser Leu Leu Phe Leu His

```
   1               5                  10                 15
Thr Arg Phe Phe Gly Trp Ser Glu Thr Met Lys Tyr Leu Leu Pro Thr
                20                 25                 30

Ala Ala Ala Gly Leu Leu Leu Ala Ala Gln Pro Ala Met Ala Asp
            35                 40                 45

Ile Val Met Thr Gln Ala Ala Pro Ser Val Pro Val Thr Pro Gly Glu
        50                 55                 60

Ser Val Ser Ile Ser Cys Thr Ser Lys Ser Leu Arg Ser Asn
65                 70                 75                 80

Gly Asn Thr Tyr Leu Tyr Trp Phe Leu Gln Arg Pro Gly Gln Ser Pro
                85                 90                 95

Gln Leu Leu Ile Tyr Arg Met Ser Asn Leu Ala Ser Gly Val Pro Asp
                100                105                110

Arg Phe Ser Gly Ser Gly Ser Gly Thr Ala Phe Thr Leu Arg Ile Ser
                115                120                125

Arg Val Glu Ala Glu Asp Val Gly Val Tyr Tyr Cys Met Gln His Leu
            130                135                140

Glu Tyr Pro Phe Thr Phe Gly Ser Gly Thr Lys Leu Glu Ile Lys Arg
145                150                155                160

Ala Asp Ala Ala Pro Thr Val Ser Ile Ser Pro Ser Ser Glu Gln
                165                170                175

Leu Thr Ser Gly Gly Ala Ser Val Val Cys Phe Leu Asn Asn Phe Tyr
            180                185                190

Pro Lys Asp Ile Asn Val Lys Trp Lys Ile Asp Gly Ser Glu Arg Gln
                195                200                205

Asn Gly Val Leu Asn Ser Trp Thr Asp Gln Asp Ser Lys Asp Ser Thr
                210                215                220

Tyr Ser Met Ser Ser Thr Leu Thr Leu Thr Lys Asp Glu Tyr Glu Arg
225                230                235                240

His Asn Ser Tyr Thr Cys Glu Ala Thr His Lys Thr Ser Thr Ser Pro
                245                250                255

Ile Val Lys Ser Phe Asn Arg Asn Glu Ser Tyr Pro Tyr Asp Val Pro
                260                265                270

Asp Tyr Ala Ser
            275

<210> SEQ ID NO 38
<211> LENGTH: 276
<212> TYPE: PRT
<213> ORGANISM: Mus musculus

<400> SEQUENCE: 38

Arg Ile Leu Pro Asp Ala Phe Tyr Arg Asn Ser Leu Leu Phe Leu His
1               5                  10                 15

Thr Arg Phe Phe Gly Trp Ser Glu Thr Met Lys Tyr Leu Leu Pro Thr
                20                 25                 30

Ala Ala Ala Gly Leu Leu Leu Ala Ala Gln Pro Ala Met Ala Asp
            35                 40                 45

Ile Val Met Thr Gln Ala Ala Pro Ser Val Pro Val Thr Pro Gly Glu
        50                 55                 60

Ser Val Ser Ile Ser Cys Arg Ser Lys Ser Leu Arg Ser Asn
65                 70                 75                 80

Gly Asn Thr Tyr Leu Tyr Trp Phe Leu Gln Arg Pro Gly Gln Ser Pro
                85                 90                 95

Gln Leu Leu Ile Tyr Arg Met Ser Asn Leu Ala Ser Gly Val Pro Asp
```

```
                100                 105                 110
Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
        130                 135                 140

Glu Tyr Pro Phe Thr Phe Gly Gly Gly Thr Lys Leu Glu Ile Lys Arg
145                 150                 155                 160

Ala Asp Ala Ala Pro Thr Val Ser Ile Phe Pro Pro Ser Ser Glu Gln
            165                 170                 175

Leu Thr Ser Gly Gly Ala Ser Val Val Cys Phe Leu Asn Asn Phe Tyr
        180                 185                 190

Pro Lys Asp Ile Asn Val Lys Trp Lys Ile Asp Gly Ser Glu Arg Gln
            195                 200                 205

Asn Gly Val Leu Asn Ser Trp Thr Asp Gln Asp Ser Lys Asp Ser Thr
        210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
            245                 250                 255

Ile Val Lys Ser Phe Asn Arg Asn Glu Ser Tyr Pro Tyr Asp Val Pro
            260                 265                 270

Asp Tyr Ala Ser
        275

<210> SEQ ID NO 39
<211> LENGTH: 276
<212> TYPE: PRT
<213> ORGANISM: Mus musculus

<400> SEQUENCE: 39

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45

Ile Val Met Thr Gln Ala Ala Pro Ser Val Ser Val Thr Pro Gly Glu
    50                  55                  60

Ser Val Ser Ile Ser Cys Arg Ser Thr Lys Ser Leu Leu Arg Ser Asn
65                  70                  75                  80

Gly Asn Thr Tyr Leu Tyr Trp Phe Leu Gln Arg Pro Gly Gln Ser Pro
                85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
        130                 135                 140

Glu Tyr Pro Phe Thr Phe Gly Gly Gly Thr Lys Leu Glu Ile Lys Arg
145                 150                 155                 160

Ala Asp Ala Ala Pro Thr Val Ser Ile Phe Pro Pro Ser Ser Glu Gln
            165                 170                 175

Leu Thr Ser Gly Gly Ala Ser Val Val Cys Phe Leu Asn Asn Phe Tyr
        180                 185                 190

Pro Lys Asp Ile Asn Val Lys Trp Lys Ile Asp Gly Ser Glu Arg Gln
```

-continued

```
                195                 200                 205
Asn Gly Val Leu Asn Ser Trp Thr Asp Gln Asp Ser Lys Asp Ser Thr
210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
                260                 265                 270

Asp Tyr Ala Ser
            275

<210> SEQ ID NO 40
<211> LENGTH: 276
<212> TYPE: PRT
<213> ORGANISM: Mus musculus

<400> SEQUENCE: 40

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
                20                  25                  30

Ala Ala Ala Gly Leu Leu Leu Ala Ala Gln Pro Ala Met Ala Asp
            35                  40                  45

Ile Val Met Thr Gln Ala Ala Pro Ser Val Pro Val Thr Pro Gly Glu
            50                  55                  60

Ser Val Ser Ile Ser Cys Arg Ser Ser Lys Ser Leu Leu Arg Ser Asn
65                  70                  75                  80

Gly Asn Thr Tyr Leu Tyr Trp Phe Leu Gln Arg Pro Gly Gln Ser Pro
                85                  90                  95

Gln Leu Leu Ile Tyr Arg Leu Ser Asn Leu Ala Ser Gly Val Pro Asp
            100                 105                 110

Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Gln Tyr Ser Glu Gln
                165                 170                 175

Leu Thr Thr Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
            195                 200                 205

Asn Gly Val Leu Asn Ser Trp Thr Asp Gln Asp Ser Lys Asp Ser Thr
210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
                260                 265                 270

Asp Tyr Ala Ser
            275
```

<210> SEQ ID NO 41
<211> LENGTH: 199
<212> TYPE: PRT
<213> ORGANISM: Mus musculus

<400> SEQUENCE: 41

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45

Ile Val Met Thr Gln Ala Ala Pro Ser Val Pro Val Thr Pro Gly Glu
50                  55                  60

Ser Val Ser Ile Ser Cys Thr Ser Lys Ser Leu Arg Ser Asn
65                  70                  75                  80

Gly Asn Thr Tyr Leu Tyr Trp Phe Leu Gln Arg Pro Gly Gln Ser Pro
                85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Ala Phe Thr Leu Arg Ile Ser
        115                 120                 125

Arg Val Glu Ala Glu Asp Val Gly Val Tyr Tyr Cys Met Gln His Leu
130                 135                 140

Glu Tyr Pro Phe Thr Phe Gly Ser Gly Thr Asn Leu Glu Ile Lys Arg
145                 150                 155                 160

Ala Asp Ala Ala Pro Thr Val Ser Ile Phe Thr Thr Ser Arg Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys
        195

<210> SEQ ID NO 42
<211> LENGTH: 783
<212> TYPE: DNA
<213> ORGANISM: Mus musculus

<400> SEQUENCE: 42
tgactgggaa aaccctggcg ttacccacgc tttgtacatg agaaaataa agtgaaacaa      60 agcactattg cactggcact cttaccgctc ttatttaccc ctgtggcaaa agccgaagtg    120
cagctgttgg agactggggg aggcgtagtg aagcccggag ggtcccttaa actctcctgt    180
gcagcctctg gattcacttt cagtaactat ggcatgtctt gggttcgcca gactccggag    240
aagaggctgg agtgggtcgc agccattaat cgtgatggtg gtaccaccta ctatacagac    300
aatgtgaagg gccgattcac catctccaga gacaatgcca gaacagcct gtacctgcaa    360 atgagcagtc tgaggtctga ggacacagcc ttgtattact gtgcaagaca gttccttctc    420
tgggacggct ggtacttcga tgtctggggc gcaggacca cggtcaccgt ctcctcagcc    480
aaaacgacac cccatctgt ctatccactg gcccctggat ctgctgccca aactaactcc    540
atggtgaccc tgggatgcct ggtcaagggc tatttccctg agccagtgac agtgacctgg    600
aactctggat ccctgtccag cggtgtgcac accttccag ctgtcctgca gtctgacctc    660
tacactctga gcagctcagt gactgtcccc tccagcacct ggcccagcga gaccgtcacc    720
tgcaacgttg cccacccggc cagcagcacc aaggtggaca agaaaattgt gcccagggat    780
tgt 783

<210> SEQ ID NO 43
<211> LENGTH: 777
<212> TYPE: DNA
<213> ORGANISM: Mus musculus

<400> SEQUENCE: 43

| | | | | | | |
|---|---|---|---|---|---|---|
| tgactgggaa | aaccctggcg | ttacccacgc | tttgtacatg | gagaaaataa | agtgaaacaa | 60 |
| agcactattg | cactggcact | cttaccgctc | ttatttaccc | ctgtggcaaa | agcccaggtt | 120 |
| cagctgcaac | agtctgacgc | tgagttggtg | aaacctggag | cttcagtgaa | gatatcctgc | 180 |
| aaggtttctg | gctacacctt | cagtgaccat | gctattcact | ggatgagtca | gagacctgga | 240 |
| cagggcctga | atggattgg | atatatttat | cctagacatg | gactactaa | ctacaatgag | 300 |
| aacttcaagg | gcaaggccac | actgactgca | gacacatcct | ccagcacagc | ctacatgcag | 360 |
| ctcaacagcc | tgacatctga | agattctgcc | gtctatttct | gtgcaagaat | gagaaactac | 420 |
| ttctatgtta | tggactactg | gggtcaagga | acctcagtca | ccgtctcctc | agccaaaacg | 480 |
| acaccccat | ctgtctatcc | actggcccct | ggatctgctg | cccaaactaa | ctccatggtg | 540 |
| accctgggat | gcctggtcaa | gggctatttc | cctgagccag | tgacagtgac | ctggaactct | 600 |
| ggatccctgt | ccagcggtgt | gcacaccttc | ccagctgtcc | tgcagtctga | cctctacact | 660 |
| ctgagcagct | cagtgactgt | cccctccagc | acctggccca | gcgagaccgt | cacctgcaac | 720 |
| gttgcccacc | cggccagcag | caccaaggtg | gacaagaaaa | ttgtgcccag | ggattgt | 777 |

<210> SEQ ID NO 44
<211> LENGTH: 777
<212> TYPE: DNA
<213> ORGANISM: Mus musculus

<400> SEQUENCE: 44

| | | | | | | |
|---|---|---|---|---|---|---|
| tgactgggaa | aaccctggcg | ttacccacgc | tttgtacatg | gagaaaataa | agtgaaacaa | 60 |
| agcactattg | cactggcact | cttaccgctc | ttatttaccc | ctgtggcaaa | agcccaggtt | 120 |
| ctgctgcaac | agtctgacgc | tgagttggtg | aaacctgggg | cttcagtgaa | gatatcctgc | 180 |
| aaggcttctg | gctacacctt | cactgaccat | gctattcact | gggtgaagca | gaggcctgaa | 240 |
| cagggcctgg | aatggattgg | atatatttat | cctgaacatg | gaactattaa | gtataatgag | 300 |
| aagttcaagg | gcaaggccac | attgactgca | gataaatcct | ccagcactgc | ctatatgcag | 360 |
| ctcaacagcc | tgacatctga | ggattcagca | gtgtatttct | gttcaagact | cactaactac | 420 |
| ttctatgtta | tggagtattg | gggtcaagga | acctcagtca | ccgtctcctc | agccaaaacg | 480 |
| acaccccat | ctgtctatcc | actggcccct | ggatctgctg | cccaaactaa | ctccatggtg | 540 |
| accctgggat | gcctggtcaa | gggctatttc | cctgagccag | tgacagtgac | ctggaactct | 600 |
| ggatccctgt | ccagcggtgt | gcacaccttc | ccagctgtcc | tgcagtctga | cctctacact | 660 |
| ctgagcagct | cagtgactgt | cccctccagc | acctggccca | gcgagaccgt | cacctgcaac | 720 |
| gttgcccacc | cggccagcag | caccaaggtg | gacaagaaaa | ttgtgcccag | ggattgt | 777 |

<210> SEQ ID NO 45
<211> LENGTH: 789
<212> TYPE: DNA
<213> ORGANISM: Mus musculus

<400> SEQUENCE: 45

| | | | | | | |
|---|---|---|---|---|---|---|
| tgactgggaa | aaccctggcg | ttacccacgc | tttgtacatg | gagaaaataa | agtgaaacaa | 60 |

```
agcactattg cactggcact cttaccgctc ttatttaccc ctgtggcaaa agccgaggtt      120
cagctgcagc agtctgtcgc tgagttggtg aaacctggag cttcagtgaa gatgtcatgc      180
aaggtttctg gctacaccct cactgaccat actattcact ggatgaagca gaggcctgaa      240
cagggcctgg aatggattgg atatatttac cctagagatg gaataactgg gtacaatgag      300
aagttcaagg gcaaggccac actgactgca gacacttctt ccagcacagc ctacatgcag      360
ctcaacagcc tgacatctga ggattctgca gtctatttct gtgccagatg gggctatagt      420
tacaggaatt acgcgtacta ctatgactac tggggccaag gcaccactct cacagtctcc      480
tcagccaaaa cgacaccccc atctgtctat ccactggccc ctggatctgc tgcccaaact      540
aactccatgg tgaccctggg atgcctggtc aagggctatt tccctgagcc agtgacagtg      600
acctggaact ctggatccct gtccagcggt gtgcacacct tcccagctgt cctgcagtct      660
gacctctaca ctctgagcag ctcagtgact gtcccctcca gcacctggcc cagcgagacc      720
gtcacctgca acgttgccca cccggccagc agcaccaagg tggacaagaa aattgtgccc      780
agggattgt                                                             789
```

```
<210> SEQ ID NO 46
<211> LENGTH: 777
<212> TYPE: DNA
<213> ORGANISM: Mus musculus

<400> SEQUENCE: 46
tgactgggaa aaccctggcg ttacccacgc tttgtacatg gagaaaataa agtgaaacaa       60
agcactattg cactggcact cttaccgctc ttatttaccc ctgtggcaaa agcccaggtt      120
cagctgcaac agtctgacgc tgacttggtg aaacctgggg cttcagtgaa gatatcctgc      180
aaggcttctg gctacaccct cactgaccat gctattcact gggtgaaaca gaggcctgaa      240
cagggcctgg aatggattgg atatatttat cctgaacatg gaactattaa gtataatgag      300
aagttcaagg gcaaggccac attgactgca gataaatcct ccagcactgc ctatatgcag      360
ctcaacagcc tgacatctga ggattcagca gtgtatttct gtgcaagact caggaactat      420
ttgtatatta tggactactg gggtcaagga acctcagtca ccgtctcctc agccaaaacg      480
acacccccat ctgtctatcc actggcccct ggatctgctg cccaaactaa ctccatggtg      540
accctgggat gcctggtcaa gggctatttc cctgagccag tgacagtgac ctggaactct      600
ggatccctgt ccagcggtgt gcacaccttc cagctgtcc tgcagtctga cctctacact      660
ctgagcagct cagtgactgt cccctccagc acctggccca gcgagaccgt cacctgcaac      720
gttgcccacc cggccagcag caccaaggtg gacaagaaaa ttgtgcccag ggattgt        777
```

```
<210> SEQ ID NO 47
<211> LENGTH: 777
<212> TYPE: DNA
<213> ORGANISM: Mus musculus

<400> SEQUENCE: 47
tgactgggaa aaccctggcg ttacccacgc tttgtacatg gagaaaataa agtgaaacaa       60
agcactattg cactggcact cttaccgctc ttatttaccc ctgtggcaaa agcccaggtt      120
cagctgcaac agtctgacgc tgagttggtg aaacctgggg cttcagtgaa gatatcctgc      180
aaggcttctg gctacaccct cactgaccat gctattcact gggtgaagca gaggcctgaa      240
cagggcctgg aatggattgg atatatttat cctgaacatg gaactattaa gtataatgag      300
aagttcaagg gcaaggccac attgactgca gataaatcct ccagcactgc ctatatgcag      360
```

```
ctcaacagcc tgacatctga ggattcagca gtgtatttct gttcaagact cactaactac    420
ttctatgtta tggagtattg gggtcaagga acctcagtca ccgtctcctc agccaaaacg    480 acaccccat  ctgtctatcc actggcccct ggatctgctg cccaaactaa ctccatggtg    540
accctgggat gcctggtcaa ggctatttc  cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg acaagaaaa  ttgtgcccag ggattgt       777

<210> SEQ ID NO 48
<211> LENGTH: 777
<212> TYPE: DNA
<213> ORGANISM: Mus musculus

<400> SEQUENCE: 48
tgactgggaa aaccctggcg ttacccacgc tttgtacatg gagaaaataa agtgaaacaa     60
agcactattg cactggcact cttaccgctc ttatttaccc ctgtggcaaa gcccaggtt    120 cagctgcaac agtctgacgc tgagttggtg aaacctggag cctcagtgaa gatatcctgc    180
aaggtttctg gctacacctt cactgaccat gctattcact ggatgaaaca gaggcctgaa    240
cagggcctgg aatggattgg atatatttat cctagagatg gttttactaa gtacaatgag    300
aagttcaagg gcaaggccac actgactgca gacacatcct ccagcacagc ctacatgcag    360
ctcaacagcc tgacatctga ggattctaca gtctatttct gtgcaagaat gactaactac    420
ttctatacta tggactactg gggtcaagga acctcagtca ccgtctcctc agccaaaacg    480 acaccccat  ctgtctatcc actggcccct ggatctgctg cccaaactaa ctccatggtg    540
accctgggat gcctggtcaa ggctatttc  cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg acaagaaaa  ttgtgcccag ggattgt       777

<210> SEQ ID NO 49
<211> LENGTH: 777
<212> TYPE: DNA
<213> ORGANISM: Mus musculus

<400> SEQUENCE: 49
tgactgggaa aaccctggcg ttacccacgc tttgtacatg gagaaaataa agtgaaacaa     60
agcactattg cactggcact cttaccgctc ttatttaccc ctgtggcaaa gcccaggtt    120 cagctgcaac agtctgacgc tgacttggtg aaacctgggg cttcagtgaa gatatcctgc    180
aaggcttctg gctacacctt cactgaccat gctattcact gggtgaaaca gaggcctgaa    240
cagggcctgg aatggattgg atatatttat cctgaacatg aactattaa  gtataatgag    300 aagttcaagg gcaaggccac attgactgca gataaatcct ccagcactgc ctatatgcag    360
ctcaacagcc tgacatctga ggattcagca gtgtatttct gttcaagact cactaactac    420
ttctatgtta tggagtattg gggtcaagga acctcagtca ccgtctcctc agccaaaacg    480 acaccccat  ctgtctatcc actggcccct ggatctgctg cccaaactaa ctccatggtg    540
accctgggat gcctggtcaa ggctatttc  cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
```

| | |
|---|---|
| gttgcccacc cggccagcag caccaaggtg acaagaaaa ttgtgcccag ggattgt | 777 |

<210> SEQ ID NO 50
<211> LENGTH: 777
<212> TYPE: DNA
<213> ORGANISM: Mus musculus

<400> SEQUENCE: 50

| | |
|---|---|
| tgactgggaa aaccctggcg ttacccacgc tttgtacatg gagaaaataa agtgaaacaa | 60 |
| agcactattg cactggcact cttaccgctc ttatttaccc ctgtggcaaa agcccaggtt | 120 |
| cagctgcaac agtctgacgc tgagttggtg aaacctgggg cttcagtgaa gatatcctgc | 180 |
| aaggcttctg gctacacctt cactgaccat gctattcact gggtgaagca gaggcctgaa | 240 |
| cagggcctgg aatggattgg atatatttat cctgaacatg gtagtattac gtataatgag | 300 |
| aagttcaagg gcaaggccac attgactgca gataaatcct ccagtactgt ctatatgcac | 360 |
| ctcaatagcc tgcatctga ggattcagca gtgtatttct gtgcaagact caggaactac | 420 |
| ttgtatgtta tggactactg gggtcaagga acctcagtca ccgtctcctc agccaaaacg | 480 |
| acaccccat ctgtctatcc actggcccct ggatctgctg cccaaactaa ctccatggtg | 540 |
| accctgggat gcctggtcaa gggctatttc cctgagccag tgacagtgac ctggaactct | 600 |
| ggatccctgt ccagcggtgt gcacaccttc ccagctgtcc tgcagtctga cctctacact | 660 |
| ctgagcagct cagtgactgt cccctccagc acctggccca gcgagaccgt cacctgcaac | 720 |
| gttgcccacc cggccagcag caccaaggtg acaagaaaa ttgtgcccag ggattgt | 777 |

<210> SEQ ID NO 51
<211> LENGTH: 777
<212> TYPE: DNA
<213> ORGANISM: Mus musculus

<400> SEQUENCE: 51

| | |
|---|---|
| tgactgggaa aaccctggcg ttacccacgc tttgtacatg gagaaaataa agtgaaacaa | 60 |
| agcactattg cactggcact cttaccgctc ttatttaccc ctgtggcaaa agcccaggtt | 120 |
| cagctgcaac agtctgaggc tgagcttgtg aagcctgggg cttcagtgaa gctgtcctgc | 180 |
| aaggcttctg gctacacctt cactgaccat gctattcact ggatgaaaca gaggcctgaa | 240 |
| cagggcctgg aatggattgg atatatctac cccagagatg attttgctaa ggtgaatgag | 300 |
| aagttcaagg gcaaggccac actgacagca gacacatcct ccagcacagc ctacatgcag | 360 |
| ctcaacagcc tgcatctga ggattctgca gtctatttct gtgcaagaat gactaactac | 420 |
| ctctatatta tggactactg gggtcaagga acctcagtca ccgtctcctc agccaaaacg | 480 |
| acaccccat ctgtctatcc actggcccct ggatctgctg cccaaactaa ctccatggtg | 540 |
| accctgggat gcctggtcaa gggctatttc cctgagccag tgacagtgac ctggaactct | 600 |
| ggatccctgt ccagcggtgt gcacaccttc ccagctgtcc tgcagtctga cctctacact | 660 |
| ctgagcagct cagtgactgt cccctccagc acctggccca gcgagaccgt cacctgcaac | 720 |
| gttgcccacc cggccagcag caccaaggtg acaagaaaa ttgtgcccag ggattgt | 777 |

<210> SEQ ID NO 52
<211> LENGTH: 777
<212> TYPE: DNA
<213> ORGANISM: Mus musculus

<400> SEQUENCE: 52

| | |
|---|---|
| tgactgggaa aaccctggcg ttacccacgc tttgtacatg gagaaaataa agtgaaacaa | 60 |

```
agcactattg cactggcact cttaccgctc ttatttaccc ctgtggcaaa agcccaggtt      120
cagctgcaac agtctgacgc tgagttggtg aaacctgggg cttcagtgaa gatatcctgc      180
aaggcttctg gctacacctt cactgaccat gctattcact gggtgaagca gaggcctgaa      240
cagggcctgg aatggattgg atatatttat cctgaacatg gtactattac gtataatgag      300
aagttcaagg gcaaggccac attgactgca gataaatcct ccagtactgt ctatatgcac      360
ctcaatagcc tgacatctga ggattcagca gtgtatttct gtgcaagact caggaactat      420
ttgtatatta tggactactg gggtcaagga acctcagtca ccgtctcctc agccaaaacg      480 acaccccat ctgtctatcc actggccccc ggatctgctg cccaaactaa ctccatggtg       540
accctgggat gcctggtcaa gggctatttc cctgagccag tgacagtgac ctggaactct      600
ggatccctgt ccagcggtgt gcacaccttc ccagctgtcc tgcagtctga cctctacact      660
ctgagcagct cagtgactgt cccctccagc acctggccca gcgagaccgt cacctgcaac      720
gttgcccacc cggccagcag caccaaggtg acaagaaaa ttgtgcccag ggattgt         777
```

```
<210> SEQ ID NO 53
<211> LENGTH: 777
<212> TYPE: DNA
<213> ORGANISM: Mus musculus

<400> SEQUENCE: 53
```

```
tgactgggaa aaccctggcg ttacccacgc tttgtacatg agaaaataa agtgaaacaa        60 agcactattg cactggcact cttaccgctc ttatttaccc ctgtggcaaa agcccaggtt      120
cagctgcaac agtctgacgc cgcgttggtg aaacctggag cttcagtgaa gatatcgtgc      180
aaggtttctg gctacacctt cagtgaccat gctattcact ggatgaagca gaggcctgaa      240
cagggcctgg aatggattgg atatattttt cctagagatg cttttagttt gaacaatgag      300
aagttcaagg gcaaggccac actgagtgca gacacatcct ccagcacagc ctacatggag      360
ctcaccagcc tgacatttga ggattctgca gtctatttct gtgcaagaat gagaaactac      420
ttctatgtta tggactactg gggtcaagga acctcagtca ccgtctcctc agccaaaacg      480 acaccccat ctgtctatac actggcccct ggatctgctg cccaaactaa ctccatggtg       540
accctgggat gcctggtcaa gggctatttc cctgagccag tgacagtgac ctggaactct      600
ggatccctgt ccagcggtgt gcacaccttc ccagctgtcc tgcagtctga cctctacact      660
ctgagcagct cagtgactgt cccctccagc acctggccca gcgagaccgt cacctgcaac      720
gttgcccacc cggccagcag caccaaggtg acaagaaaa ttgtgcccag ggattgt         777
```

```
<210> SEQ ID NO 54
<211> LENGTH: 837
<212> TYPE: DNA
<213> ORGANISM: Mus musculus

<400> SEQUENCE: 54
```

```
taagattagc ggatcctacc tgacgctttt tatcgcaact ctctactgtt tctccatacc       60 cgttttttg gatggagtga aacgatgaaa tacctattgc ctacggcagc cgctggattg       120
ttattactcg ctgcccaacc agccatggcc gatgttgtgc tgacccagac tccactctcc      180
ctgcctgtca ctcttggaga tcaagcctcc atctcttgca gatctagtca gagccttta       240 cacagtaatg gaaacaccta tttacattgg tacctgctga agccaggcca gtctccaaag      300
ctcctgatct acaagttttc caaccgattt tctggggtcc cagacaggtt cagtggcagt      360
ggatcaggga cagatttcac actcaagatc accagagtgg aggctgagga tctgggagtt      420
```

| | |
|---|---:|
| tatttctgct ctcaaagtac acatgtgctc acgttcggtg ctgggaccaa gctggagctg | 480 |
| aaacgggctg atgctgcacc aactgtatcc atcttccac catccagtga gcagttaaca | 540 |
| tctggaggtg cctcagtcgt gtgcttcttg aacaacttct accccaaaga catcaatgtc | 600 |
| aagtggaaga ttgatggcag tgaacgacaa aatggcgtcc tgaacagttg gactgatcag | 660 |
| gacagcaaag acagcaccta cagcatgagc agcaccctca cgttgaccaa ggacgagtat | 720 |
| gaacgacata cagctatac ctgtgaggcc actcacaaga catcaacttc acccattgtc | 780 |
| aagagcttca acaggaatga gtcttatcca tatgatgtgc cagattatgc gagctaa | 837 |

<210> SEQ ID NO 55
<211> LENGTH: 840
<212> TYPE: DNA
<213> ORGANISM: Mus musculus

<400> SEQUENCE: 55

| | |
|---|---:|
| taagattagc ggatcctacc tgacgctttt tatcgcaact ctctactgtt tctccatacc | 60 |
| cgttttttg gatggagtga aacgatgaaa tacctattgc ctacggcagc cgctggattg | 120 |
| ttattactcg ctgcccaacc agccatggcc gatattgtga tgacccaggc tgcaccctct | 180 |
| gtacctgtca ctcctggaga gtcagtatcc atctcctgca cgtctagtaa gagtctcctg | 240 |
| cgtagtaatg caacactta cttgtattgg ttcctgcaga ggccaggcca gtctcctcag | 300 |
| ctcctgatat atcggatgtc caaccttgcc tcgggagtcc cagacaggtt cagtggcagt | 360 |
| gggtcaggaa ctgctttcac actgagaatc agtagagtgg aggctgagga tgtgggtgtt | 420 |
| tattactgta tgcaacatct agaatatcct ttcacgttcg gctcggggac aaagttggaa | 480 |
| ataaaacggg ctgatgctgc accaactgta tccatcttcc caccatccag tgagcagtta | 540 |
| acatctggag gtgcctcagt cgtgtgcttc ttgaacaact tctaccccaa agacatcaat | 600 |
| gtcaagtgga gagattgatgg cagtgaacga caaaatggcg tcctgaacag ttggactgat | 660 |
| caggacagca aagacagcac ctacagcatg agcagcaccc tcacgttgac caaggacgag | 720 |
| tatgaacgac ataacagcta cctgtgtgag gccactcaca agacatcaac ttcacccatt | 780 |
| gtcaagagct tcaacaggaa tgagtcttat ccatatgatg tgccagatta tgcgagctaa | 840 |

<210> SEQ ID NO 56
<211> LENGTH: 843
<212> TYPE: DNA
<213> ORGANISM: Mus musculus

<400> SEQUENCE: 56

| | |
|---|---:|
| taagattagc ggatcctacc tgacgctttt tatcgcaact ctctactgtt tctccatacc | 60 |
| cgttttttg gatggagtga aacgatgaaa tacctattgc ctacggcagc cgctggattg | 120 |
| ttattactcg ctgcccaacc agccatggcc gacatcgtta tgtctcagtc tccatcctcc | 180 |
| ctagctgtgt cagttggaga aaggttact atgagctgca agtccagcca gagccttta | 240 |
| catagtagca atcaaaagaa ctacttggcc tggtaccagc agaaaccagg gcagtctcct | 300 |
| aaagtgctga tttactgggc atccactaga gaatctgggg tccctgatcg cttcacaggc | 360 |
| agtggatctg ggacagattt cactctcacc atcaccagtg tgaagtctga agacctggca | 420 |
| gtttattact gtcagcaata ttatagctat ccgtggacgt tcggtggcgg caccaggctg | 480 |
| gaaatcaaac gggctgatgc tgcaccaact gtatccatct tcccaccatc cagtgagcag | 540 |
| ttaacatctg gaggtgcctc agtcgtgtgc ttcttgaaca acttctaccc caaagacatc | 600 |
| aatgtcaagt ggaagattga tggcagtgaa cgacaaaatg gcgtcctgaa cagttggact | 660 |

| | |
|---|---|
| gatcaggaca gcaaagacag cacctacagc atgagcagca ccctcacgtt gaccaaggac | 720 |
| gagtatgaac gacataacag ctatacctgt gaggccactc acaagacatc aacttcaccc | 780 |
| attgtcaaga gcttcaacag gaatgagtct tatccatatg atgtgccaga ttatgcgagc | 840 |
| taa | 843 |

<210> SEQ ID NO 57
<211> LENGTH: 840
<212> TYPE: DNA
<213> ORGANISM: Mus musculus

<400> SEQUENCE: 57

| | |
|---|---|
| taagattagc ggatcctacc tgacgctttt tatcgcaact ctctactgtt tctccatacc | 60 |
| cgttttttg gatggagtga aacgatgaaa tacctattgc ctacggcagc cgctggattg | 120 |
| ttattactcg ctgcccaacc agccatggcc gatattgtga tgacccaggc tgcaccctct | 180 |
| gtacctgtca ctcctggaga gtcagtatcc atctcctgca ggtctagtaa gagtctcctg | 240 |
| cgcagtaatg gcaacactta cttgtattgg ttcctgcaga ggccaggcca gtctcctcag | 300 |
| ctcctgatat atcggctgtc caaccttgcc tcaggagtcc cagacaggtt cagtggcagt | 360 |
| gggtctggaa ctgctttcac actgagaatc agtagagtgg aggctgagga tgtgggtgtt | 420 |
| tattactgta tgcaacatct agaatatcct ttcacattcg gctcggggac aaagttggaa | 480 |
| ataaaacggg ctgatgctgc accaactgta tccatcttcc caccatccag tgagcagtta | 540 |
| acatctggag gtgcctcagt cgtgtgcttc ttgaacaact tctaccccaa agacatcaat | 600 |
| gtcaagtgga agattgatgg cagtgaacga caaaatggcg tcctgaacag ttggactgat | 660 |
| caggacagca agacagcac ctacagcatg agcagcaccc tcacgttgac caaggacgag | 720 |
| tatgaacgac ataacagcta tacctgtgag gccactcaca agacatcaac ttcacccatt | 780 |
| gtcaagagct tcaacaggaa tgagtcttat ccatatgatg tgccagatta tgcgagctaa | 840 |

<210> SEQ ID NO 58
<211> LENGTH: 840
<212> TYPE: DNA
<213> ORGANISM: Mus musculus

<400> SEQUENCE: 58

| | |
|---|---|
| taagattagc ggatcctacc tgacgctttt tatcgcaact ctctactgtt tctccatacc | 60 |
| cgttttttg gatggagtga aacgataaaa tacctattgc ctacggcagc cgctggattg | 120 |
| ttattactcg ctgcccaacc agccatggcc gatattgtga tgacccaggc tgcaccctct | 180 |
| gtacctgtca ctcctggaga gtcagtatcc atctcctgca cgtctagtaa gagtctcctg | 240 |
| cgtagtaatg gcaacactta cttgtattgg ttcctgcaga ggccaggcca gtctcctcag | 300 |
| ctcctgatat atcggatgtc caaccttgcc tcgggagtcc cagacaggtt cagtggcagt | 360 |
| gggtcaggaa ctgctttcac actgagaatc agtagagtgg aggctgagga tgtgggtgtt | 420 |
| tattactgta tgcaacatct agaatatcct ttcacgttcg gctcggggac aaagttggaa | 480 |
| ataaaacggg ctgatgctgc accaactgta tccatcctcc caccatccag tgagcagtta | 540 |
| acatctggag gtgcctcagt cgtgtgcttc ttgaacaact tctaccccaa agacatcaat | 600 |
| gtcaagtgga agattgatgg cagtgaacga caaaatggcg tcctgaacag ttggactgat | 660 |
| caggacagca agacagcac ctacagcatg agcagcaccc tcacgttgac caaggacgag | 720 |
| tatgaacgac ataacagcta tacctgtgag gccactcaca agacatcaac ttcacccatt | 780 |
| gtcaagagct tcaacaggaa tgagtcttat ccatatgatg tgccagatta tgcgagctaa | 840 |

<210> SEQ ID NO 59
<211> LENGTH: 840
<212> TYPE: DNA
<213> ORGANISM: Mus musculus

<400> SEQUENCE: 59

```
taagattagc ggatcctacc tgacgctttt tatcgcaact ctctactgtt tctccatacc    60
cgttttttg  gatggagtga aacgatgaaa tacctattgc ctacggcagc cgctggattg   120
ttattactcg ctgcccaacc agccatggcc gatattgtga tgacccaggc tgcaccctct   180
gtacctgtca ctcctggaga gtcagtttcc atctcctgca ggtcttctaa gagtctcctg   240
cgtactaatg gcaacactta cttgcattgg ttcctgcaga ggccaggcca gtctcctcag   300
ctcctgatat atcggatgtc caaccttgcc tcaggagtcc cagacaggtt cagtggcagt   360
gggtcaggaa ctgttttcac actgagaatc agtagagtgg aggctgagga tgtgggtgtt   420
tattactgta tgcaacatct agaatatcca ttcacgttcg gctcggggac aaagttggaa   480
ataaaaggg  ctgatgctgc accaactgta tccatcttcc caccatccag tgagcagtta   540
acatctggag gtgcctcagt cgtgtgcttc ttgaacaact ctacccccaa agacatcaat   600
gtcaagtgga agattgatgg cagtgaacga caaaatggcg tcctgaacag ttggactgat   660
caggacagca agacagcac  ctacagcatg agcagcaccc tcacgttgac caaggacgag   720
tatgaacgac ataacagcta tacctgtgag gccactcaca agacatcaac ttcacccatt   780
gtcaagagct tcaacaggaa tgagtcttat ccatatgatg tgccagatta tgcgagctaa   840
```

<210> SEQ ID NO 60
<211> LENGTH: 840
<212> TYPE: DNA
<213> ORGANISM: Mus musculus

<400> SEQUENCE: 60

```
taagattagc ggatcctacc ttacgctttt tatcgcaact ctctactgtt tctccatacc    60
cgttttttg  gatggagtga aacgatgaaa tacctattgc ctacggcagc cgctggattg   120
ttattactcg ctgcccaacc agccatggcc gatattgtga tgacccaggc tgcaccctct   180
gtacctgtca ctcctggaga atcagtatcc atctcctgca ggtctagtaa gagtctcctg   240
cgtagtaatg gcaacactta cttgtattgg ttcctgcaga ggccaggcca gtctcctcag   300
ctcctgatat atcggctgtc taaccttgcc tcaggagtcc cagacaggtt cagtggcagt   360
gggtcaggaa ctgctttcac actgagaatc agtagagtgg aggctgagga tgtgggtgtt   420
tattactgta tgcaacatct agaatatcct ttcacattcg gctcggggac aaagttggaa   480
ataaaacggg ctgatgctgc accaactgta tccatcttcc caccatccag tgagcagtta   540
acatctggag gtgcctcagt cgtgtgcttc ttgaacaact ctacccccaa agacatcaat   600
gtcaagtgga agattgatgg cagtgaacga caaaatggcg tcctgaacag ttggactgat   660
caggacagca agacagcac  ctacagcatg agcagcaccc tcacgttgac caaggacgag   720
tatgaacgac ataacagcta tacctgtgag gccactcaca agacatcaac ttcacccatt   780
gtcaagagct tcaacaggaa tgagtcttat ccatatgatg tgccagatta tgcgagctaa   840
```

<210> SEQ ID NO 61
<211> LENGTH: 840
<212> TYPE: DNA
<213> ORGANISM: Mus musculus

<400> SEQUENCE: 61

```
taagattagc ggatcctacc tgacgctttt tatcgcaact ctctactgtt tctccatacc      60 cgttttttg datggagtga aacgatgaaa tacctattgc ctacggcagc cgctggattg     120
ttattactcg ctgcccaacc agccatggcc gatattgtga tgacccaggc tgcaccctct    180
gtacctgtca ctcctggaga gtcagtatcc atctcctgca cgtctagtaa gagtctcctg    240
cgtagtaatg gcaacactta cttgtattgg ttcctgcaga ggccaggcca gtctcctcag    300
ctcctgatat atcggatgtc caaccttgcc tcgggagtcc cagacaggtt cagtggcagt    360
gggtcaggaa ctgctttcac actgagaatc agtagagtgg aggctgagga tgtgggtgtt    420
tattactgta tgcaacatct agaatatcct ttcacgttcg gctcggggac aaagttggaa    480
ataaaacggg ctgatgctgc accaactgta tccatctccc caccatccag tgagcagtta    540
acatctggag gtgcctcagt cgtgtgcttc ttgaacaact ctaccccaa agacatcaat    600 gtcaagtgga agattgatgg cagtgaacga caaaatggcg tcctgaacag ttggactgat    660
caggacagca agacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840

<210> SEQ ID NO 62
<211> LENGTH: 840
<212> TYPE: DNA
<213> ORGANISM: Mus musculus

<400> SEQUENCE: 62
taagattagc ggatcctacc tgacgctttt tatcgcaact ctctactgtt tctccatacc      60 cgttttttg datggagtga aacgatgaaa tacctattgc ctacggcagc cgctggattg     120
ttattactcg ctgcccaacc agccatggcc gatattgtga tgacccaggc tgcaccctct    180
gtacctgtca ctcctggaga gtcagtatcc atctcctgca ggtccagtaa gagtctcctg    240
cgtagtaatg gcaacactta cttgtattgg ttcctgcaga ggccaggcca gtctcctcag    300
ctcctcatat atcggatgtc caaccttgcc tcaggagtcc cagacaggtt cagtggcagt    360
gggtcaggaa ctgccttcac actgagaatc agtagagtgg aggctgagga tgtgggtgtt    420
tattactgta tgcaacatct agaatatcct ttcacgttcg gaggggggac caagctggaa    480
ataaaacggg ctgatgctgc accaactgta tccatcttcc caccatccag tgagcagtta    540
acatctggag gtgcctcagt cgtgtgcttc ttgaacaact ctaccccaa agacatcaat    600 gtcaagtgga agattgatgg cagtgaacga caaaatggcg tcctgaacag ttggactgat    660
caggacagca agacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840

<210> SEQ ID NO 63
<211> LENGTH: 840
<212> TYPE: DNA
<213> ORGANISM: Mus musculus

<400> SEQUENCE: 63
taagattagc ggatcctacc tgacgctttt tatcgcaact ctcttctgtt tctccatacc      60 cgttttttg datggagtga aacgatgaaa tacctattgc ctacggcagc cgctggattg     120
ttattactcg ctgcccaacc agccatggcc gatattgtga tgacccaggc tgcaccctct    180
gtatctgtca ctcctggaga gtcagtatcc atctcctgca ggtctactaa gagtctcctg    240
```

```
cgtagtaatg gcaacactta cttgtattgg ttcctccaga ggccaggcca gtctcctcag    300
ctcctgatat atcggatgtc caaccttgcc tcaggagtcc cagacaggtt cagtggcagt    360
gggtcaggaa ctgctttcac actgagaatc agtagagtgg aggctgagga tgtgggtgtt    420
tattactgta tgcaacatct agaatatcct ttcacgttcg gagggggac caagctggaa    480 ataaaacggg ctgatgctgc accaactgta tccatcttcc caccatccag tgagcagtta    540
acatctggag gtgcctcagt cgtgtgcttc ttgaacaact ctacccaa agacatcaat    600 gtcaagtgga agattgatgg cagtgaacga caaaatggcg tcctgaacag ttggactgat    660
caggacagca agacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840
```

<210> SEQ ID NO 64
<211> LENGTH: 840
<212> TYPE: DNA
<213> ORGANISM: Mus musculus
<400> SEQUENCE: 64

```
taagattagc ggatcctacc tgacgctttt tatcgcaact ctctactgtt tctccatacc     60 cgttttttg gatggagtga aacgatgaaa tacctattgc ctacggcagc cgctggattg    120
ttattactcg ctgcccaacc agccatggcc gatattgtga tgacccaggc tgcaccctct    180
gtacctgtca ctcctggaga gtcagtatcc atctcctgca ggtctagtaa gagtctccta    240
cgtagtaatg gcaacactta cttgtattgg ttcctgcaga ggccaggcca gtctcctcag    300
ctcctgatat atcggatgtc caaccttgcc tcaggagtcc cagacaggtt cagtggcagt    360
gggtcaggaa ctgccttcac actgagaatc agtagagtgg aggctgagga tgtgggtgtt    420
tattactgta tgcaacatct agaatatcct ttcacgttcg gagggggac caagctggaa    480 ataaaacggg ctgatgctgc accaactgta tccatcttcc caccatccag tgagcagtta    540
acatctggag gtgcctcagt cgtgtgcttc ttgaacaact ctacccaa agacatcaat    600 gtcaagtgga agattgatgg cagtgaacga caaaatggcg tcctgaacag ttggactgat    660
caggacagca agacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840
```

<210> SEQ ID NO 65
<211> LENGTH: 840
<212> TYPE: DNA
<213> ORGANISM: Mus musculus
<400> SEQUENCE: 65

```
taagattagc ggatcctacc tgacgctttt tatcgcaact ctctactgtt tctccatacc     60 cgttttttg gatggagtga aacgatgaaa tacctattgc ctacggcagc cgctggattg    120
ttattactcg ctgcccaacc agccatggcc gatattgtga tgacccaggc tgcaccctct    180
gtacctgtca ctcctggaga gtcagtatcc atctcctgca ggtctagtaa gagtctcctg    240
cgcagtaatg gcaacactta cttgtattgg ttcctgcaga ggccaggcca gtctcctcag    300
ctcctgatat atcggctgtc caaccttgcc tcaggagtcc cagacaggtt cagtggcagt    360
gggtcaggaa ctgctttcac actgagaatc agtagagtgg aggctgagga tgtgggtgtt    420
tattactgta tgcaacatct agaatatcct ttcacattcg gctcggggac aaagttggaa    480
```

-continued

```
ataaaacggg ctgatgctgc accaactgta tccatcttcc cacaatacag tgagcagtta      540
acaactggag gtgcctcagt cgtgtgcttc ttgaacaact tctacccaa agacatcaat       600 gtcaagtgga agattgatgg cagtgaacga caaaatggcg tcctgaacag ttggactgat      660
caggacagca aagacagcac ctacagcatg agcagcaccc tcacgttgac caaggacgag      720
tatgaacgac ataacagcta tacctgtgag gccactcaca agacatcaac ttcacccatt      780
gtcaagagct tcaacaggaa tgagtcttat ccatatgatg tgccagatta tgcgagctaa      840
```

<210> SEQ ID NO 66
<211> LENGTH: 597
<212> TYPE: DNA
<213> ORGANISM: Mus musculus

<400> SEQUENCE: 66

```
cggatcctac ctgacgcttt ttatcgcaac tctctactgt ttctccatac ccgttttttt       60
ggatggagtg aaacgatgaa atacctattg cctacggcag ccgctggatt gttattactc      120
gctgcccaac cagccatggc cgatattgtg atgacccagg ctgcaccctc tgtacctgtc      180
actcctggag agtcagtatc catctcctgc acgtctagta agagtctcct gcgtagtaat      240
ggcaacactt acttgtattg gttcctgcag aggccaggcc agtctcctca gctcctgata      300
tatcggatgt ccaaccttgc ctcgggagtc ccagacaggt tcagtggcag tgggtcagga      360
actgctttca cactgagaat cagtagagtg gaggctgagg atgtgggtgt ttattactgt      420
atgcaacatc tagaatatcc tttcacgttc ggctcgggga caaatttgga aataaaacgg      480
gctgatgctg caccaactgt atccatcttc acaacatcca gagagcagtt aacatctgga      540
ggtgcctcag tcgtgtgctt cttgaacaac ttctacccca agacatcaa tgtcaag         597
```

<210> SEQ ID NO 67
<211> LENGTH: 765
<212> TYPE: PRT
<213> ORGANISM: Homo sapiens

<400> SEQUENCE: 67

```
Gln Glu Gly Lys Phe Ser Gly Pro Leu Lys Pro Met Thr Phe Ser Ile
1               5                   10                  15

Tyr Glu Gly Gln Glu Pro Ser Gln Ile Ile Phe Gln Phe Lys Ala Asn
            20                  25                  30

Pro Pro Ala Val Thr Phe Glu Leu Thr Gly Glu Thr Asp Asn Ile Phe
        35                  40                  45

Val Ile Glu Arg Glu Gly Leu Leu Tyr Tyr Asn Arg Ala Leu Asp Arg
    50                  55                  60

Glu Thr Arg Ser Thr His Asn Leu Gln Val Ala Ala Leu Asp Ala Asn
65                  70                  75                  80

Gly Ile Ile Val Glu Gly Pro Val Pro Ile Thr Ile Lys Val Lys Asp
                85                  90                  95

Ile Asn Asp Asn Arg Pro Thr Phe Leu Gln Ser Lys Tyr Glu Gly Ser
            100                 105                 110

Val Arg Gln Asn Ser Arg Pro Gly Lys Pro Phe Leu Tyr Val Asn Ala
        115                 120                 125

Thr Asp Leu Asp Asp Pro Ala Thr Pro Asn Gly Gln Leu Tyr Tyr Gln
    130                 135                 140

Ile Val Ile Gln Leu Pro Met Ile Asn Asn Val Met Tyr Phe Gln Ile
145                 150                 155                 160

Asn Asn Lys Thr Gly Ala Ile Ser Leu Thr Arg Glu Gly Ser Gln Glu
                165                 170                 175
```

Leu Asn Pro Ala Lys Asn Pro Ser Tyr Asn Leu Val Ile Ser Val Lys
            180                 185                 190

Asp Met Gly Gly Gln Ser Glu Asn Ser Phe Ser Asp Thr Thr Ser Val
            195                 200                 205

Asp Ile Ile Val Thr Glu Asn Ile Trp Lys Ala Pro Lys Pro Val Glu
            210                 215                 220

Met Val Glu Asn Ser Thr Asp Pro His Pro Ile Lys Ile Thr Gln Val
225                 230                 235                 240

Arg Trp Asn Asp Pro Gly Ala Gln Tyr Ser Leu Val Asp Lys Glu Lys
            245                 250                 255

Leu Pro Arg Phe Pro Phe Ser Ile Asp Gln Glu Gly Asp Ile Tyr Val
            260                 265                 270

Thr Gln Pro Leu Asp Arg Glu Glu Lys Asp Ala Tyr Val Phe Tyr Ala
            275                 280                 285

Val Ala Lys Asp Glu Tyr Gly Lys Pro Leu Ser Tyr Pro Leu Glu Ile
            290                 295                 300

His Val Lys Val Lys Asp Ile Asn Asp Asn Pro Pro Thr Cys Pro Ser
305                 310                 315                 320

Pro Val Thr Val Phe Glu Val Gln Glu Asn Glu Arg Leu Gly Asn Ser
            325                 330                 335

Ile Gly Thr Leu Thr Ala His Asp Arg Asp Glu Glu Asn Thr Ala Asn
            340                 345                 350

Ser Phe Leu Asn Tyr Arg Ile Val Glu Gln Thr Pro Lys Leu Pro Met
            355                 360                 365

Asp Gly Leu Phe Leu Ile Gln Thr Tyr Ala Gly Met Leu Gln Leu Ala
            370                 375                 380

Lys Gln Ser Leu Lys Lys Gln Asp Thr Pro Gln Tyr Asn Leu Thr Ile
385                 390                 395                 400

Glu Val Ser Asp Lys Asp Phe Lys Thr Leu Cys Phe Val Gln Ile Asn
            405                 410                 415

Val Ile Asp Ile Asn Asp Gln Ile Pro Ile Phe Glu Lys Ser Asp Tyr
            420                 425                 430

Gly Asn Leu Thr Leu Ala Glu Asp Thr Asn Ile Gly Ser Thr Ile Leu
            435                 440                 445

Thr Ile Gln Ala Thr Asp Ala Asp Glu Pro Phe Thr Gly Ser Ser Lys
            450                 455                 460

Ile Leu Tyr His Ile Ile Lys Gly Asp Ser Glu Gly Arg Leu Gly Val
465                 470                 475                 480

Asp Thr Asp Pro His Thr Asn Thr Gly Tyr Val Ile Ile Lys Lys Pro
            485                 490                 495

Leu Asp Phe Glu Thr Ala Ala Val Ser Asn Ile Val Phe Lys Ala Glu
            500                 505                 510

Asn Pro Glu Pro Leu Val Phe Gly Val Lys Tyr Asn Ala Ser Ser Phe
            515                 520                 525

Ala Lys Phe Thr Leu Ile Val Thr Asp Val Asn Glu Ala Pro Gln Phe
            530                 535                 540

Ser Gln His Val Phe Gln Ala Lys Val Ser Glu Asp Val Ala Ile Gly
545                 550                 555                 560

Thr Lys Val Gly Asn Val Thr Ala Lys Asp Pro Glu Gly Leu Asp Ile
            565                 570                 575

Ser Tyr Ser Leu Arg Gly Asp Thr Arg Gly Trp Leu Lys Ile Asp His
            580                 585                 590

Val Thr Gly Glu Ile Phe Ser Val Ala Pro Leu Asp Arg Glu Ala Gly

```
                    595                 600                 605
Ser Pro Tyr Arg Val Gln Val Ala Thr Glu Val Gly Gly Ser Ser
        610                 615                 620

Leu Ser Ser Val Ser Glu Phe His Leu Ile Leu Met Asp Val Asn Asp
625                 630                 635                 640

Asn Pro Pro Arg Leu Ala Lys Asp Tyr Thr Gly Leu Phe Phe Cys His
                645                 650                 655

Pro Leu Ser Ala Pro Gly Ser Leu Ile Phe Glu Ala Thr Asp Asp Asp
            660                 665                 670

Gln His Leu Phe Arg Gly Pro His Phe Thr Phe Ser Leu Gly Ser Gly
        675                 680                 685

Ser Leu Gln Asn Asp Trp Glu Val Ser Lys Ile Asn Gly Thr His Ala
    690                 695                 700

Arg Leu Ser Thr Arg His Thr Asp Phe Glu Glu Arg Glu Tyr Val Val
705                 710                 715                 720

Leu Ile Arg Ile Asn Asp Gly Gly Arg Pro Pro Leu Glu Gly Ile Val
                725                 730                 735

Ser Leu Pro Val Thr Phe Cys Ser Cys Val Glu Gly Ser Cys Phe Arg
            740                 745                 750

Pro Ala Gly His Gln Thr Gly Ile Pro Thr Val Gly Met
        755                 760                 765

<210> SEQ ID NO 68
<211> LENGTH: 222
<212> TYPE: PRT
<213> ORGANISM: Homo sapiens

<400> SEQUENCE: 68

Gln Glu Gly Lys Phe Ser Gly Pro Leu Lys Pro Met Thr Phe Ser Ile
1               5                   10                  15

Tyr Glu Gly Gln Glu Pro Ser Gln Ile Ile Phe Gln Phe Lys Ala Asn
                20                  25                  30

Pro Pro Ala Val Thr Phe Glu Leu Thr Gly Glu Thr Asp Asn Ile Phe
            35                  40                  45

Val Ile Glu Arg Glu Gly Leu Leu Tyr Tyr Asn Arg Ala Leu Asp Arg
        50                  55                  60

Glu Thr Arg Ser Thr His Asn Leu Gln Val Ala Ala Leu Asp Ala Asn
65                  70                  75                  80

Gly Ile Ile Val Glu Gly Pro Val Pro Ile Thr Ile Lys Val Lys Asp
                85                  90                  95

Ile Asn Asp Asn Arg Pro Thr Phe Leu Gln Ser Lys Tyr Glu Gly Ser
                100                 105                 110

Val Arg Gln Asn Ser Arg Pro Gly Lys Pro Phe Leu Tyr Val Asn Ala
            115                 120                 125

Thr Asp Leu Asp Asp Pro Ala Thr Pro Asn Gly Gln Leu Tyr Tyr Gln
130                 135                 140

Ile Val Ile Gln Leu Pro Met Ile Asn Asn Val Met Tyr Phe Gln Ile
145                 150                 155                 160

Asn Asn Lys Thr Gly Ala Ile Ser Leu Thr Arg Glu Gly Ser Gln Glu
                165                 170                 175

Leu Asn Pro Ala Lys Asn Pro Ser Tyr Asn Leu Val Ile Ser Val Lys
            180                 185                 190
```

-continued

```
Asp Met Gly Gly Gln Ser Glu Asn Ser Phe Ser Asp Thr Thr Ser Val
        195                 200                 205
Asp Ile Ile Val Thr Glu Asn Ile Trp Lys Ala Pro Lys Pro
    210                 215                 220
```

ANTIBODY DRUG CONJUGATE TREATMENT OF COLORECTAL CANCER

RELATED APPLICATIONS

The present application is a Continuation-In-Part of co-pending U.S. Non-Provisional application Ser. No. 12/928,274, filed Dec. 8, 2010, which is in turn, a continuation of Non-Provisional application Ser. No. 12/395,569, filed Feb. 27, 2009, which in turn, is a continuation of PCT Application No. PCT/GB2007/050513 filed Aug. 29, 2007, which in turn, claims priority from G.B. Application No. 0616971.8 filed Aug. 29, 2006 and U.S. Provisional Application Ser. No. 60/842,431 filed Sep. 6, 2006.

The present application is also a Continuation-In-Part of co-pending U.S. Non-Provisional application Ser. No. 12/329,500, filed Dec. 5, 2008, which in turn, is a continuation of PCT Application No. PCT/EP2007/055537 filed Jun. 5, 2007, which in turn, claims priority from G.B. Application No. 0611116.5 filed Jun. 6, 2006 and U.S. Provisional Application Ser. No. 60/811,681 filed Jun. 7, 2006.

The present application is also a Continuation-In-Part of co-pending PCT Application No. PCT/US2010/031719, filed Apr. 20, 2010, which in turn, claims priority from U.S. Provisional Application Ser. No. 61/170,980, filed Apr. 20, 2009.

Applicants claim the benefits of 35 U.S.C. §120 as to the U.S. Non-Provisional Applications and the PCT applications, and priority under 35 U.S.C. §119 as to the said G.B. and U.S. Provisional applications, and the entire disclosures of all applications are incorporated herein by reference in their entireties.

INTRODUCTION

The present invention relates to the identification of a membrane protein associated with colorectal cancer which has utility as a target for the treatment of colorectal cancer, in particular using antibodies which bind to said membrane protein, and has utility as a marker for colorectal cancer and colorectal cancer metastases and which also forms a biological target against which therapeutic antibodies (or other affinity reagents such as Affibodies, Nanobodies or Unibodies) or other pharmaceutical agents can be made.

BACKGROUND OF THE INVENTION

Colorectal Cancer:

Colorectal cancer (CRC) is one of the leading causes of cancer-related morbidity and mortality, responsible for an estimated half a million deaths per year, mostly in Western, well developed countries. In these territories, CRC is the third most common malignancy (estimated number of new cases per annum in USA and EU is approximately 350,000 per year). Estimated healthcare costs related to treatment for colorectal cancer in the United States are more than $8 billion.

Colorectal Cancer Diagnosis:

Today, the fecal occult blood test and colonoscopy, a highly invasive procedure, are the most frequently used screening and diagnostic methods for colorectal cancer.

Other diagnostic tools include Flexible Sigmoidoscopy (allowing the observation of only about half of the colon) and Double Contrast Barium Enema (DCBE, to obtain X-ray images).

Colorectal Cancer Staging:

CRC has four distinct stages: patients with stage I disease, have a five-year survival rate of >90%, while those with metastatic stage IV disease have a <5% survival rate according to the US National Institutes of Health (NIH).

Colorectal Cancer Treatment:

Once CRC has been diagnosed, the correct treatment needs to be selected. Surgery is usually the main treatment for rectal cancer, although radiation and chemotherapy will often be given before surgery. Possible side effects of surgery include bleeding from the surgery, deep vein thrombosis, and damage to nearby organs during the operation.

Currently, 60 percent of colorectal cancer patients receive chemotherapy to treat their disease; however, this form of treatment only benefits a few percent of the population, while carrying with it high risks of toxicity, thus demonstrating a need to better define the patient selection criteria.

Colorectal cancer has a 30 to 40 percent recurrence rate within an average of 18 months after primary diagnosis. As with all cancers, the earlier it is detected the more likely it can be cured, especially as pathologists have recognised that the majority of CRC tumours develop in a series of well-defined stages from benign adenomas.

Colon Cancer Survival by Stage

| Stage | Survival Rate |
|---|---|
| I | 93% |
| IIA | 85% |
| IIB | 72% |
| IIIA | 83% |
| IIIB | 64% |
| IIIC | 44% |
| IV | 8% |

Therapeutic Challenges

The major challenges in colorectal cancer treatment are to improve early detection rates, to find new non-invasive markers that can be used to follow disease progression and identify relapse, and to find improved and less toxic therapies, especially for more advanced disease where 5 year survival is still very poor. There is a great need to identify targets which are more specific to the cancer cells, e.g. ones which are expressed on the surface of the tumour cells so that they can be attacked by promising new approaches like immunotherapeutics and targeted toxins.

SUMMARY OF THE INVENTION

The present invention provides methods and compositions for screening, diagnosis, prognosis and therapy of colorectal cancer, for colorectal cancer patients' stratification, for monitoring the effectiveness of colorectal cancer treatment, and for drug development for treatment of colorectal cancer.

We have used mass spectrometry to identify peptides generated by gel electrophoresis or tagging with iTRAQ reagents and tryptic digest of membrane proteins extracted from colorectal cancer tissue samples. Peptide sequences were compared to existing protein and cDNA databases and the corresponding gene sequences identified. The protein of the invention has not been previously reported to originate from colorectal cancer cell membranes and represents a protein of new diagnostic and therapeutic value.

Thus, a first aspect of the invention provides methods for diagnosis of colorectal cancer that comprises analysing a sample of colon tissue e.g. by gel electrophoresis, iTRAQ or other appropriate protein separation technique to detect the protein of the invention. Such methods are also set forth in commonly assigned, co-pending parent application Ser. No.

12/329,500, filed Dec. 5, 2008, the disclosure of which is incorporated herein in its entirety. These methods are also suitable for screening, prognosis, monitoring the results of therapy, drug development and discovery of new targets for drug treatment.

A second aspect of the invention provides methods of treating colorectal cancer, comprising administering to a patient a therapeutically effective amount of a compound that modulates (e.g., upregulates or downregulates) or complements the expression or the biological activity (or both) of the protein of the invention in patients having colorectal cancer, in order to (a) prevent the onset or development of colorectal cancer; (b) prevent the progression of colorectal cancer; or (c) ameliorate the symptoms of colorectal cancer.

A third aspect of the invention provides methods of screening for compounds that modulate (e.g., upregulate or downregulate) the expression or biological activity of the protein of the invention.

A fourth aspect of the invention provides monoclonal and polyclonal antibodies or other affinity reagents such as Affibodies, Nanobodies or Unibodies capable of immunospecific binding to the protein of the invention.

Thus, in a fifth aspect, the present invention provides a method for screening for and/or diagnosis of colorectal cancer in a human subject, which method comprises the step of identifying the presence or absence of the protein of the invention, in a biological sample obtained from said human subject.

In a sixth aspect, the present invention provides a method for monitoring and/or assessing colorectal cancer treatment in a human subject, which comprises the step of identifying the presence or absence of the protein of the invention, in a biological sample obtained from said human subject.

In a seventh aspect, the present invention provides a method for identifying the presence or absence of metastatic colorectal cancer cells in a biological sample obtained from a human subject, which comprises the step of identifying the presence or absence of the protein of the invention.

In an eighth aspect, the present invention provides a method for monitoring and/or assessing colorectal cancer treatment in a human subject, which comprises the step of determining whether the protein of the invention is increased/decreased in a biological sample obtained from a patient.

The biological sample used can be from any source such as a serum sample or a tissue sample, e.g. colorectal tissue. For instance, when looking for evidence of metastatic colorectal cancer, one would look at major sites of colorectal cancer metastasis, e.g. the liver, the peritoneal cavity, the pelvis, the retroperitoneum and the lungs.

Other aspects of the present invention are set out below and in the claims herein.

BRIEF DESCRIPTION OF THE FIGURES

FIG. 1 shows the amino acid sequence of the protein of the invention isolated from colorectal cancer samples using 1D-gel electrophoresis technology. The tryptic fragments detected experimentally by mass spectrometry are highlighted, mass match peptides are shown in bold and tandem peptides are underlined.

FIG. 2 is similar to FIG. 1, except the protein of the invention was isolated from colorectal cancer samples using iTRAQ.

DETAILED DESCRIPTION OF THE INVENTION

Figure 3A:
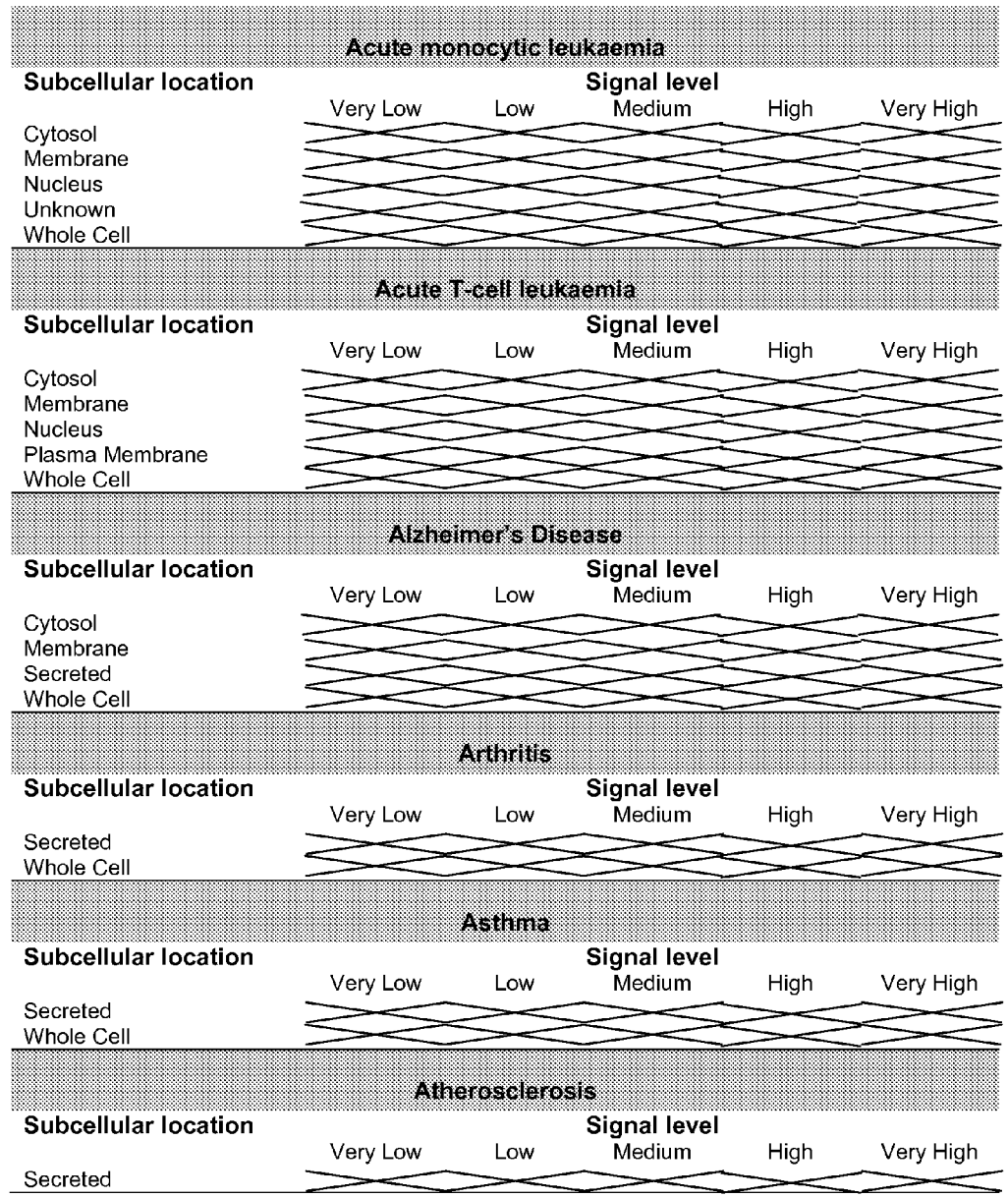
FIGS. 3a-3i-show the Protein Index for the protein of the invention in various diseases. The list of dieases investigated is shown in Table 3a with Table 3b indicating subcellular locations.
Figure 3B:
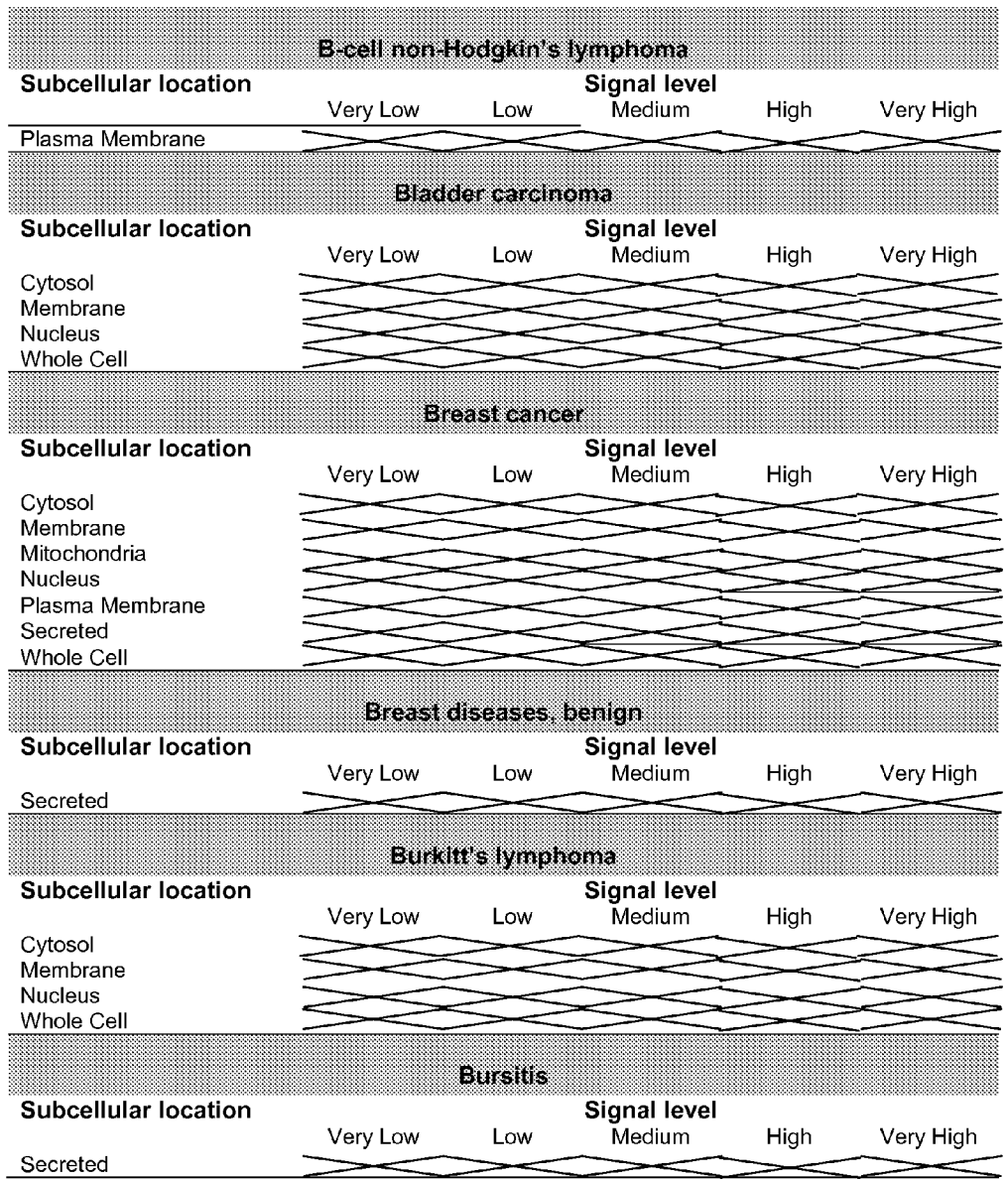
Figure 3C:
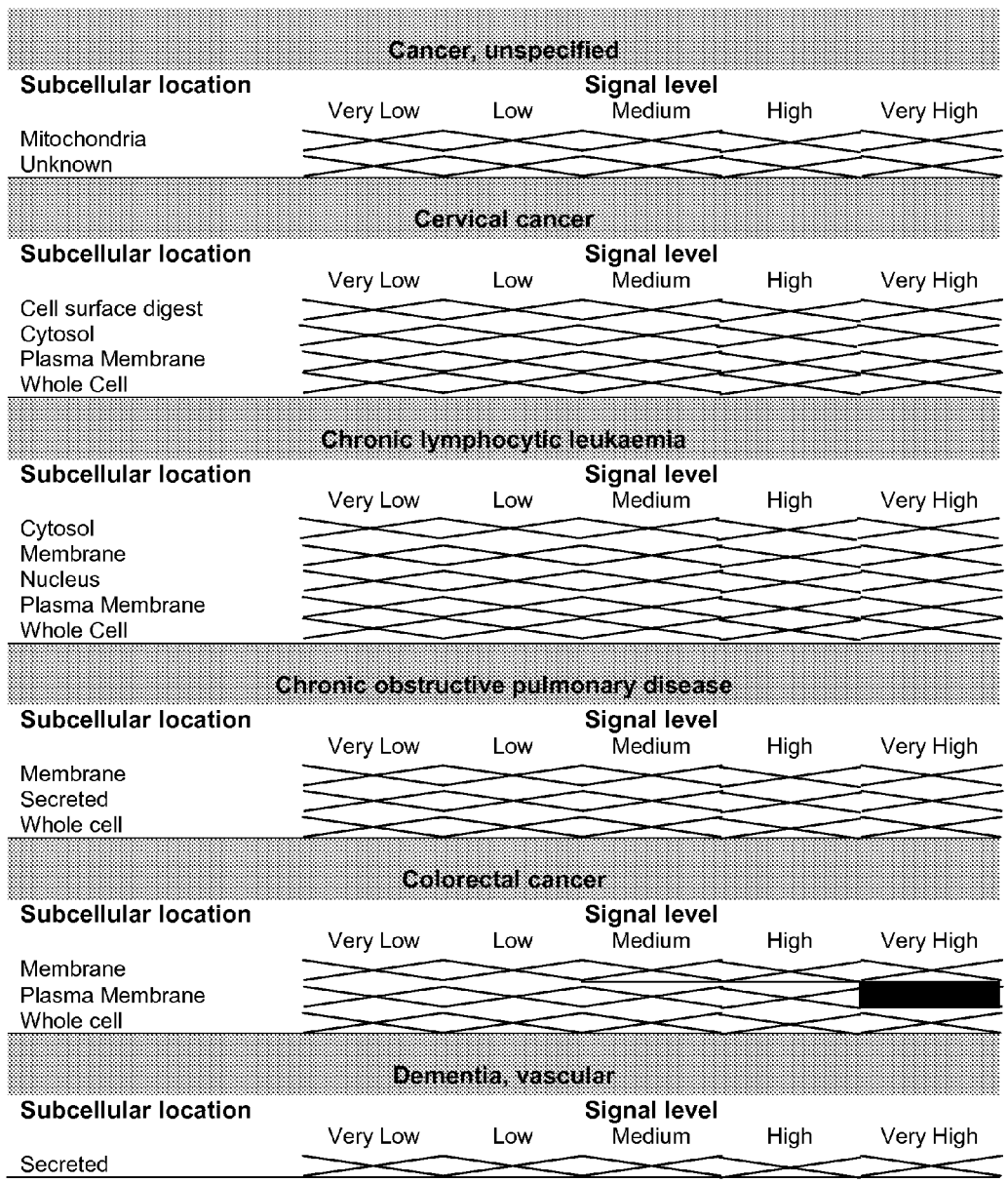
Figure 3D:
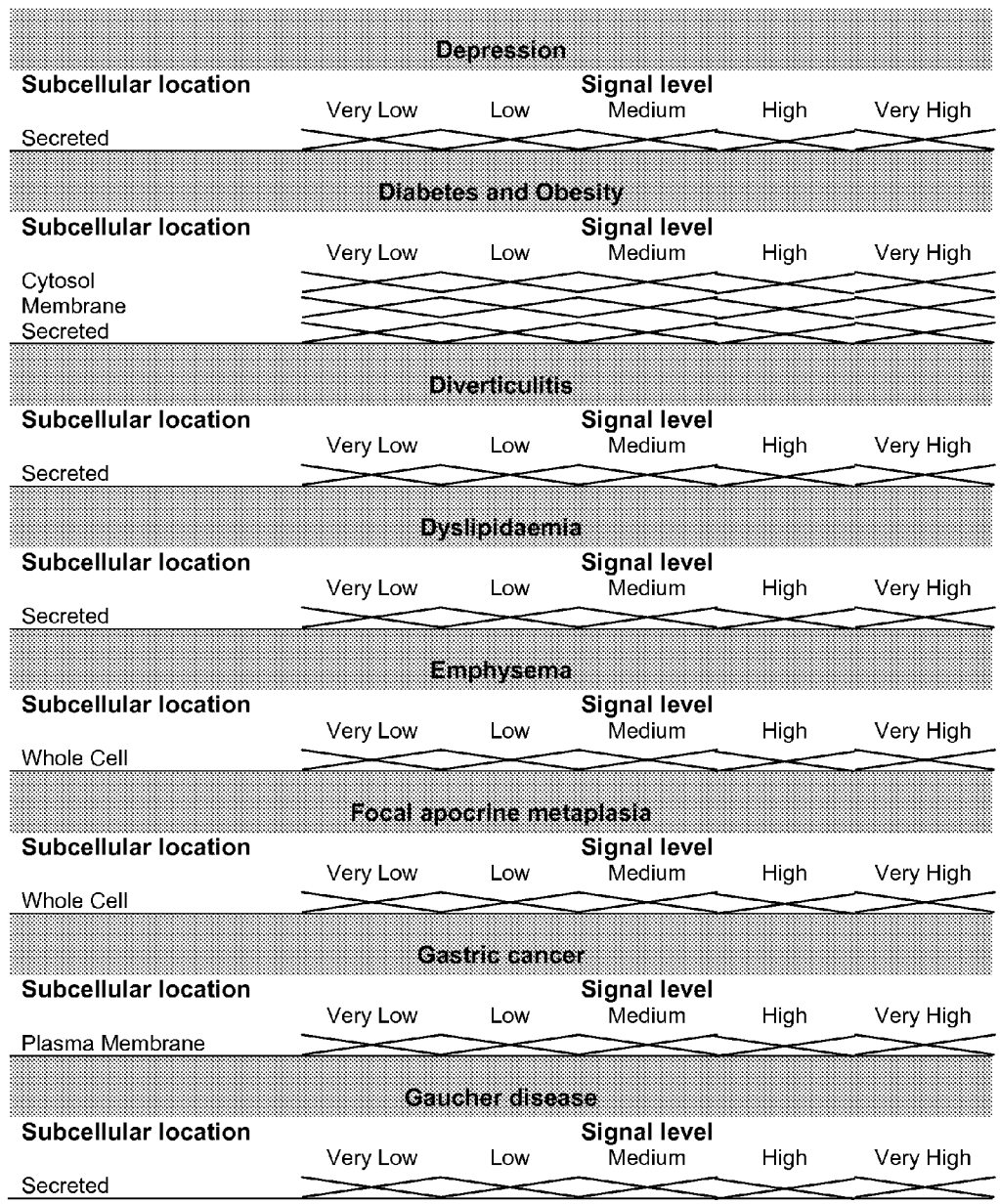
Figure 3E:
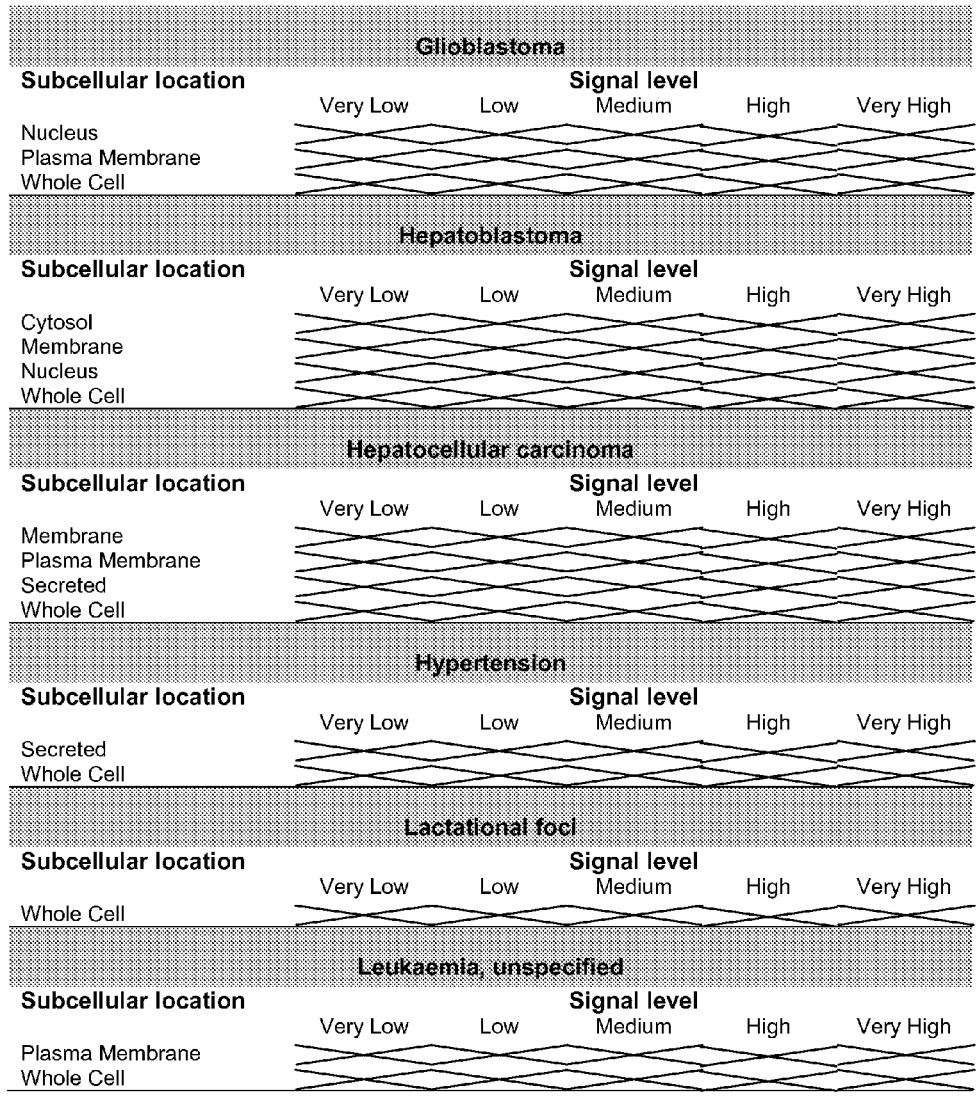
Figure 3F:
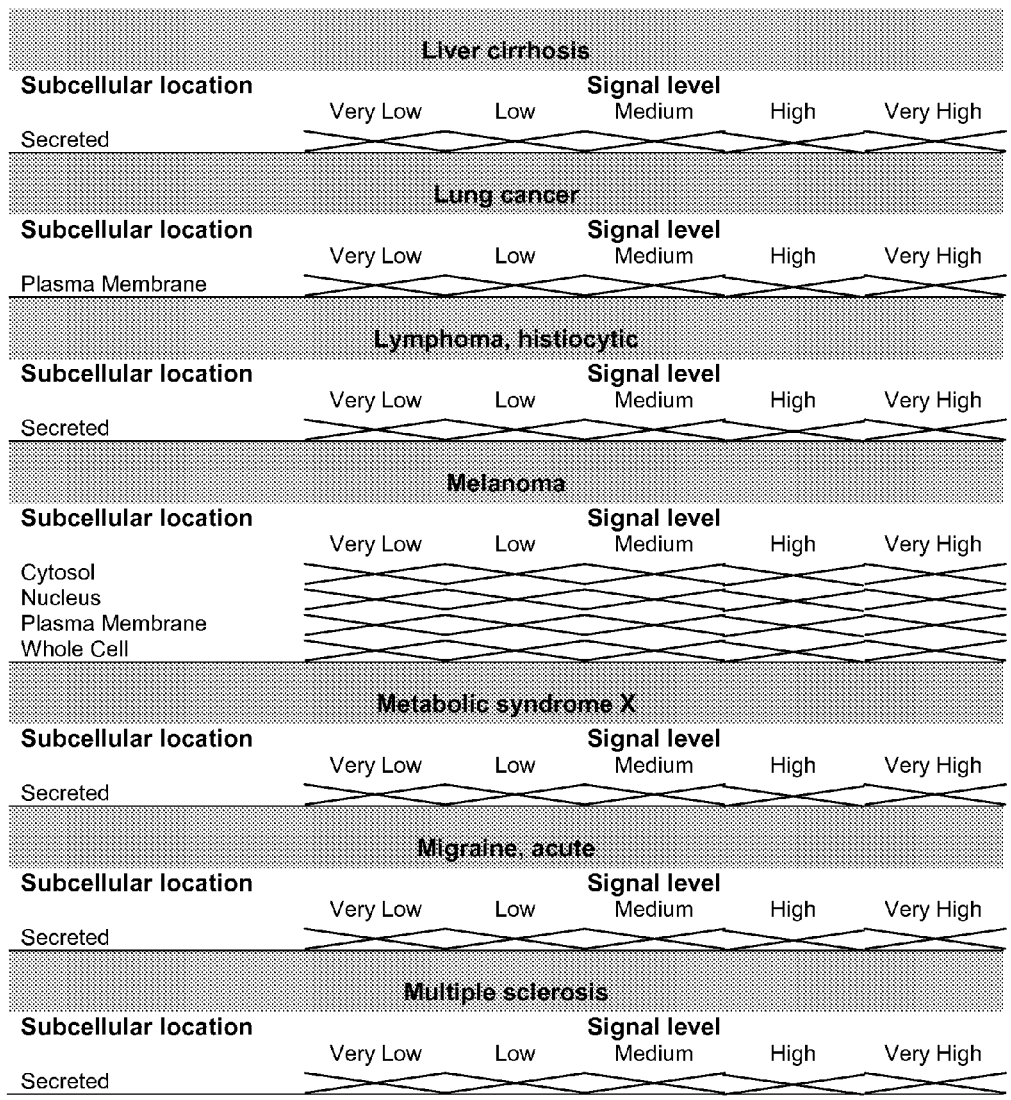
Figure 3G:
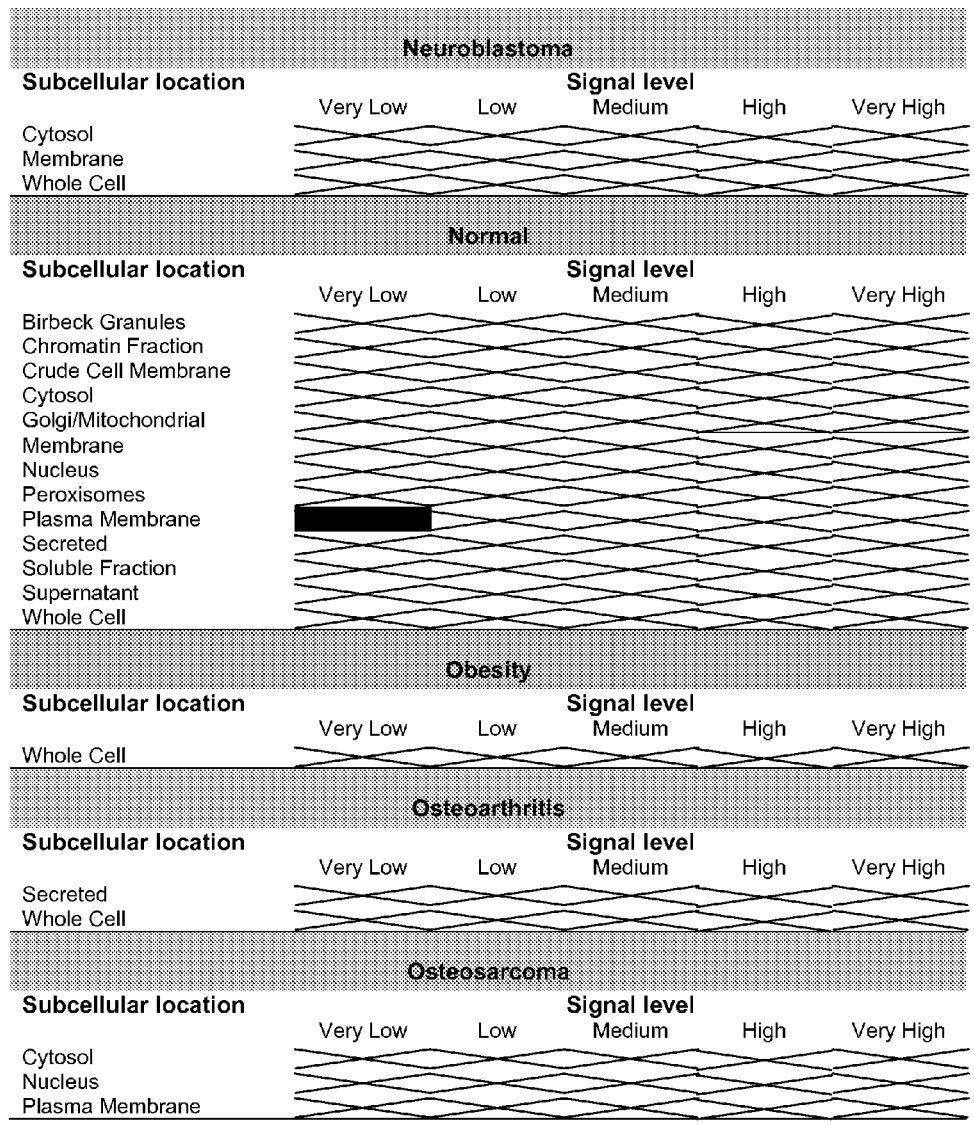
Figure 3H:
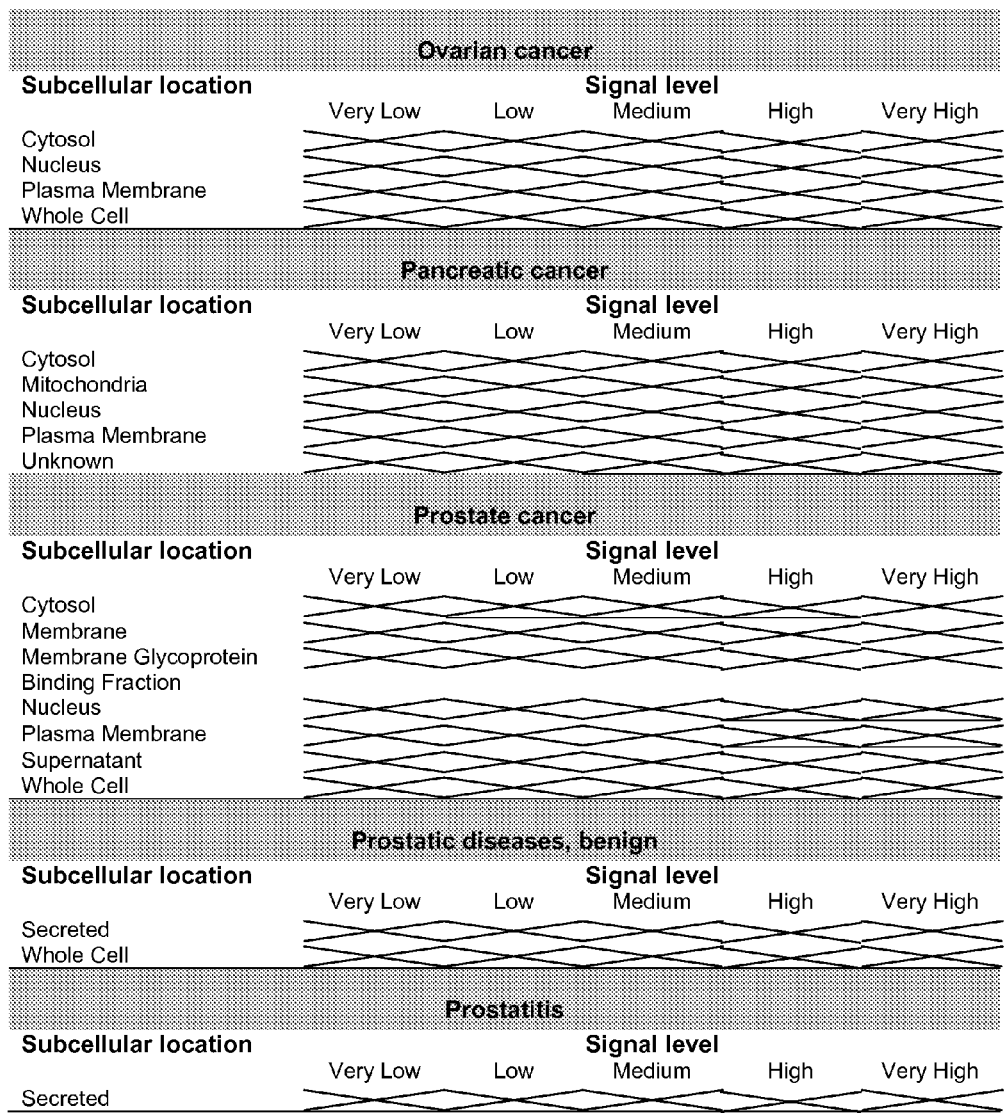
Figure 3I:
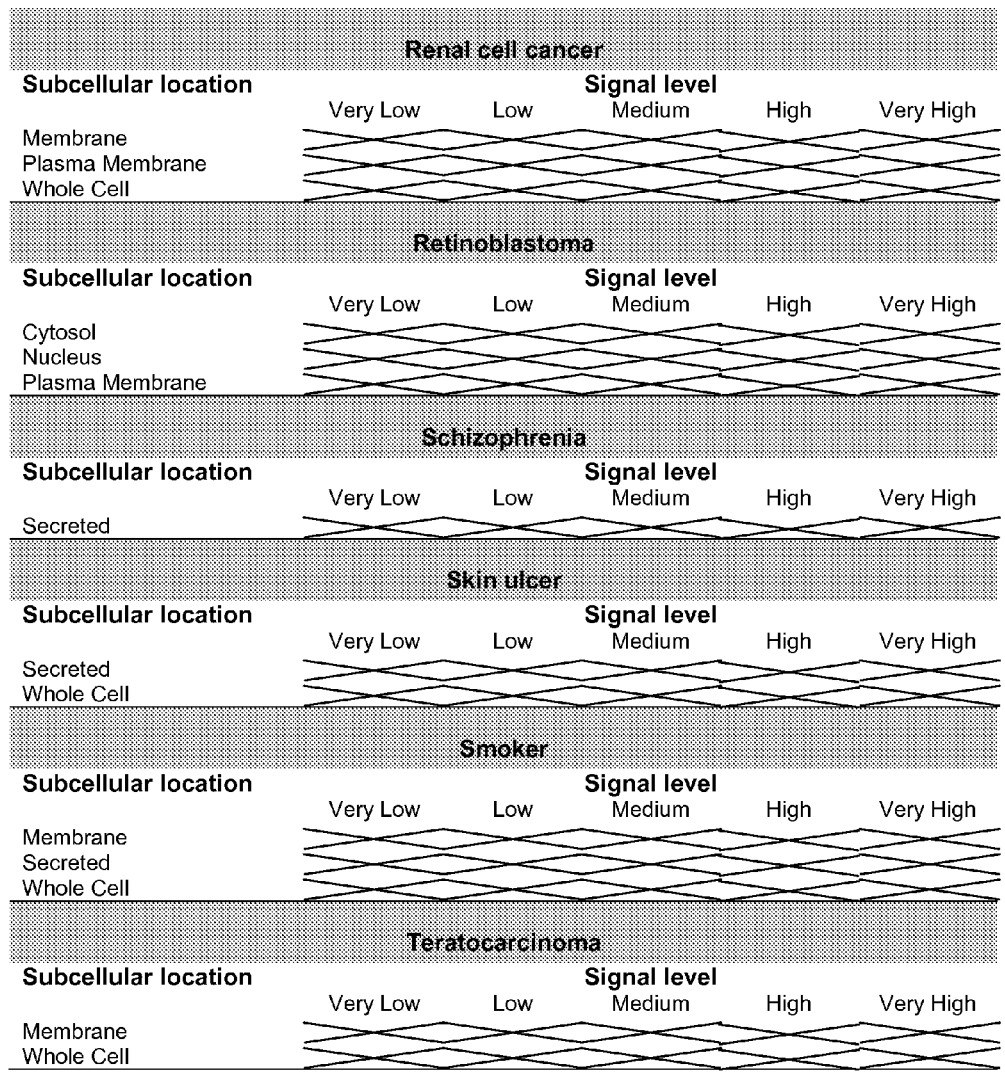

The invention described in detail below provides methods and compositions for clinical screening, diagnosis and prognosis of colorectal cancer in a mammalian subject for identifying patients most likely to respond to a particular therapeutic treatment, for monitoring the results of colorectal cancer therapy, for drug screening and drug development. The invention also encompasses the administration of therapeutic compositions to a mammalian subject to treat or prevent colorectal cancer. The mammalian subject may be a non-human mammal, but is preferably human, more preferably a human adult, i.e. a human subject at least 21 (more preferably at least 35, at least 50, at least 60, at least 70, or at least 80) years old. For clarity of disclosure, and not by way of limitation, the invention will be described with respect to the analysis of colon tissue. However, as one skilled in the art will appreciate, the assays and techniques described below can be applied to other types of patient samples, including body fluids (e.g. blood, urine or saliva), a tissue sample from a patient at risk of having colorectal cancer (e.g. a biopsy such as a colorectal biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

As used herein, colon tissue refers to the colon itself, as well as the tissue adjacent to and/or within the strata underlying the colon.

OGTA001

In one aspect of the invention, one-dimensional electrophoresis or isobaric tags for relative and absolute quantification (iTRAQ) are used to analyze colorectal cancer tissue samples from a subject, preferably a living subject, in order to measure the expression of the protein of the invention for screening or diagnosis of colorectal cancer, to determine the prognosis of a colorectal cancer patient, to monitor the effectiveness of colorectal cancer therapy, or for drug development.

As used herein, the term "Protein of the invention", or "OGTA001", refers to the protein illustrated in FIG. 1 detected experimentally by 1D gel electrophoresis and iTRAQ analysis of colorectal tissue samples. Protein derivatives of this sequence may also be useful for the same purposes as described herein.

This protein has been identified in membrane protein extracts of colorectal tissue samples from colorectal cancer patients, through the methods and apparatus of the Preferred Technologies (1D gel electrophoresis or iTRAQ together with tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at www.expasy.com), and the following entry: Q12864, Cadherin-17, was identified.

According to SWISS-PROT, Cadherin-17 is known to be predominantly expressed in the gastrointestinal tract and pancreatic duct. It is not detected in kidney, lung, liver, brain, adrenal gland or skin. Cadherins are calcium dependent cell adhesion proteins. They preferentially interact with themselves in a homophilic manner in connecting cells; cadherins may thus contribute to the sorting of heterogeneous cell types. Cadherin-17 may have a role in the morphological organization of liver and intestine. It is involved in intestinal peptide transport.

The protein of the invention is useful as are fragments e.g. antigenic or immunogenic fragments thereof and derivatives thereof. Antigenic or immunogenic fragments will typically be of length 12 amino acids or more e.g. 20 amino acids or more e.g. 50 or 100 amino acids or more. Fragments may be 10% or more of the length of the full protein e.g. 25% or more e.g. 50% or 75% or 90% or 95% or more of the length of the full protein.

Antigenic or immunogenic fragments will be capable of eliciting a relevant immune response in a patient. DNA encoding the protein of the invention is also useful as are fragments thereof e.g. DNA encoding fragments of the protein of the invention such as immunogenic fragments thereof. Fragments of nucleic acid (e.g. DNA) encoding the protein of the invention may be 10% or more of the length of the full coding region e.g. 25% or more e.g. 50% or 75% or 90% or 95% or more of the length of the full coding region. Fragments of nucleic acid (e.g. DNA) may be 36 nucleotides or more e.g. 60 nucleotides or more e.g. 150 or 300 nucleotides or more in length.

Derivatives of the protein of the invention include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. For example derivatives may have sequence identity of 80% or more e.g. 90% or more e.g. 95% or more as compared with the reference sequence over the full length of the reference sequence. Derivatives will typically have essentially the same biological function as the protein from which they are derived. Derivatives will typically be comparably antigenic or immunogenic to the protein from which they are derived.

Table 1 below illustrates the different occurrences of OGTA001 as detected by 1D gel electrophoresis and mass spectrometry of membrane protein extracts of colorectal tissue samples from colorectal cancer patients. The first column provides the molecular weight, the second column gives information on the subfractionation protocol used, if any (see Example 1 below), and the last column provides a list of the sequences observed by mass spectrometry and the corresponding SEQ ID Nos.

Table 2 below illustrates the different occurrences of OGTA001 as detected by iTRAQ and mass spectrometry of membrane protein extracts of colorectal tissue samples from colorectal cancer patients. The first column provides the sample number, the second column gives information on the iTRAQ experiment number for that sample and the last column provides a list of the sequences observed by mass spectrometry and the corresponding SEQ ID Nos.

TABLE 1

Colorectal cancer 1D gel

| MW (Da) | Subfractionation | Tryptics identified [SEQ ID No] |
|---|---|---|
| 91099 | | DEENTANSFLNYR [4], DNVESAQASEVKPLR [7], WNDPGAQYSLVDK [13] |
| 114588 | Nucleotide Binding | AENPEPLVFGVK [2], DAYVFYAVAK [3], DEENTANSFLNYR [4], DINDNRPTFLQSK [6], DNVESAQASEVKPLR [7] |
| 117144 | Nucleotide Binding | DEENTANSFLNYR [4], DEYGKPLSYPLEIHVK [5], DNVESAQASEVKPLR [7], IDHVTGEIFSVAPLDR [10] |
| 119837 | Nucleotide Binding | AENPEPLVFGVK [2], DEENTANSFLNYR [4], DNVESAQASEVKPLR [7], TGAISLTR [13] |
| 125678 | Nucleotide Binding | DEENTANSFLNYR [4], DNVESAQASEVKPLR [7] |

TABLE 2

Colorectal cancer iTRAQ

| Sample no. | Experiment no. | Tryptics identified [SEQ ID No] |
|---|---|---|
| Sample 1 | Experiment 1 | AENPEPLVFGVK [2], DEYGKPLSYPLEIHVK [5], GWLK [9], IDHVTGEIFSVAPLDR [10], KPLDFETAAVSNIVFK [11], LGVDTDPHTNTGYVIIK [12], VKDINDNPPTCPSPVTVFEVQENER [14], VSEDVAIGTK [15], WNDPGAQYSLVDKEKLPR [17] |
| Sample 1 | Experiment 2 | AENPEPLVFGVK [2], IDHVTGEIFSVAPLDR [10] |
| Sample 2 | Experiment 1 | EGSQELNPAK [8] |

For OGTA001, the detected level obtained upon analyzing tissue from subjects having colorectal cancer relative to the detected level obtained upon analyzing tissue from subjects free from colorectal cancer will depend upon the particular analytical protocol and detection technique that is used. Accordingly, the present invention contemplates that each laboratory will establish a reference range in subjects free from colorectal cancer according to the analytical protocol and detection technique in use, as is conventional in the diagnostic art. Preferably, at least one control positive tissue sample from a subject known to have colorectal cancer or at least one control negative tissue sample from a subject known to be free from colorectal cancer (and more preferably both positive and negative control samples) are included in each batch of test samples analysed.

OGTA001 can be used for detection, prognosis, diagnosis, or monitoring of colorectal cancer or for drug development. In one embodiment of the invention, tissue from a subject (e.g., a subject suspected of having colorectal cancer) is analysed by 1D electrophoresis or iTRAQ for detection of OGTA001. An increased abundance of OGTA001 in the tissue from the subject relative to tissue from a subject or subjects free from colorectal cancer (e.g., a control sample) or a previously determined reference range indicates the presence of colorectal cancer.

In relation to fragments, immunogenic fragments or antigenic fragments of OGTA001, for colorectal cancer applications, preferably these comprise one or more of the sequences identified as tryptic sequences in the $3^{rd}$ column of Table 1 or the $3^{rd}$ column of Table 2.

OGTA001 may, in particular, be characterized as an isoform having a MW substantially as recited (eg +/−10%, particularly +/−5% of the value) in column 1 of any of the rows of Table 1.

The present invention additionally provides: (a) a preparation comprising isolated OGTA001; (b) a preparation comprising one or more fragments of OGTA001; and (c) antibodies or other affinity reagents such as Affibodies, Nanobodies or Unibodies that bind to OGTA001, to said fragments, or both to OGTA001 and to said fragments. As used herein, OGTA001 is "isolated" when it is present in a preparation that is substantially free of contaminating proteins, i.e., a preparation in which less than 10% (preferably less than 5%, more preferably less than 1%) of the total protein present is contaminating protein(s). A contaminating protein is a protein having a significantly different amino acid sequence from that of isolated OGTA001, as determined by mass spectral analysis. As used herein, a "significantly different" sequence is one that permits the contaminating protein to be resolved from OGTA001 by mass spectral analysis, performed according to the Reference Protocols.

OGTA001 can be assayed by any method known to those skilled in the art, including but not limited to, the Preferred Technologies described herein, kinase assays, enzyme assays, binding assays and other functional assays, immunoassays, and western blotting. In one embodiment, OGTA001 is separated on a 1-D gel by virtue of its MW and visualized by staining the gel. In one embodiment, OGTA001 is stained with a fluorescent dye and imaged with a fluorescence scanner. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety. In another embodiment, OGTA001 is analysed using isobaric tags for relative and absolute quantification (iTRAQ).

Alternatively, OGTA001 can be detected in an immunoassay. In one embodiment, an immunoassay is performed by contacting a sample from a subject to be tested with an anti-OGTA001 antibody (or other affinity reagent such as an Affibody, Nanobody or Unibody) under conditions such that immunospecific binding can occur if OGTA001 is present, and detecting or measuring the amount of any immunospecific binding by the affinity reagent. Anti-OGTA001 affinity reagents can be produced by the methods and techniques taught herein.

OGTA001 may be detected by virtue of the detection of a fragment thereof e.g. an immunogenic or antigenic fragment thereof. Fragments may have a length of at least 10, more typically at least 20 amino acids eg at least 50 or 100 amino acids eg at least 200 or 500 amino acids.

In one embodiment, binding of antibody (or other affinity reagent such as an Affibody, Nanobody or Unibody) in tissue sections can be used to detect aberrant OGTA001 localization or an aberrant level of OGTA001. In a specific embodiment, an antibody (or other affinity reagent such as an Affibody, Nanobody or Unibody) to OGTA001 can be used to assay a patient tissue (e.g., a colon tissue) for the level of OGTA001 where an aberrant level of OGTA001 is indicative of colorectal cancer. As used herein, an "aberrant level" means a level that is increased compared with the level in a subject free from colorectal cancer or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, OGTA001 can be detected in a fluid sample (e.g., blood, urine, or saliva) by means of a two-step sandwich assay. In the first step, a capture reagent (e.g., an anti-OGTA001 antibody or other affinity reagent such as an Affibody, Nanobody or Unibody) is used to capture OGTA001. The capture reagent can optionally be immobilized on a solid phase. In the second step, a directly or indirectly labeled detection reagent is used to detect the captured OGTA001. In one embodiment, the detection reagent is a lectin. Any lectin can be used for this purpose that preferentially binds to OGTA001 rather than to other isoforms that have the same core protein as OGTA001 or to other proteins that share the antigenic determinant recognized by the affinity reagent. In a preferred embodiment, the chosen lectin binds OGTA001 with at least 2-fold greater affinity, more preferably at least 5-fold greater affinity, still more preferably at least 10-fold greater affinity, than to said other isoforms that have the same core protein as OGTA001 or to said other proteins that share the antigenic determinant recognized by the affinity reagent. Based on the present description, a lectin that is suitable for detecting OGTA001 can readily be identified by methods well known in the art, for instance upon testing one or more lectins enumerated in Table I on pages 158-159 of Sumar et al., Lectins as Indicators of Disease-Associated Glycoforms, In: Gabius H-J & Gabius S (eds.), 1993, Lectins and Glycobiology, at pp. 158-174 (which is incorporated herein by reference in its entirety). In an alternative embodiment, the detection reagent is an antibody (or other affinity reagent such as an Affibody, Nanobody or Unibody), e.g., an antibody that immunospecifically detects other post-translational modifications, such as an antibody that immunospecifically binds to phosphorylated amino acids. Examples of such antibodies include those that bind to phosphotyrosine (BD Transduction Laboratories, catalog nos.: P11230-050/P11230-150; P11120; P38820; P39020), those that bind to phosphoserine (Zymed Laboratories Inc., South San Francisco, Calif., catalog no. 61-8100) and those that bind to phosphothreonine (Zymed Laboratories Inc., South San Francisco, Calif., catalogue nos. 71-8200, 13-9200).

If desired, a gene encoding OGTA001, a related gene, or related nucleic acid sequences or subsequences, including complementary sequences, can also be used in hybridization assays. A nucleotide encoding OGTA001, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding OGTA001, or for differential diagnosis of subjects with signs or symptoms suggestive of colorectal cancer. In particular, such a hybridization assay can be carried out by a method comprising contacting a subject's sample containing nucleic acid with a nucleic acid probe capable of hybridizing to a DNA or RNA that encodes OGTA001, under conditions such that hybridization can occur, and detecting or measuring any resulting hybridization.

The invention also provides diagnostic kits, comprising an anti-OGTA001 antibody (or other affinity reagent such as an Affibody, Nanobody or Unibody). In addition, such a kit may optionally comprise one or more of the following: (1) instructions for using the anti-OGTA001 affinity reagent for diagnosis, prognosis, therapeutic monitoring or any combination of these applications; (2) a labeled binding partner to the affinity reagent; (3) a solid phase (such as a reagent strip) upon which the anti-OGTA001 affinity reagent is immobilized; and (4) a label or insert indicating regulatory approval for diagnostic, prognostic or therapeutic use or any combination thereof. If no labeled binding partner to the affinity reagent is provided, the anti-OGTA001 affinity reagent itself can be labeled with a detectable marker, e.g., a chemiluminescent, enzymatic, fluorescent, or radioactive moiety.

The invention also provides a kit comprising a nucleic acid probe capable of hybridizing to RNA encoding OGTA001. In a specific embodiment, a kit comprises in one or more containers a pair of primers (e.g., each in the size range of 6-30 nucleotides, more preferably 10-30 nucleotides and still more preferably 10-20 nucleotides) that under appropriate reaction conditions can prime amplification of at least a portion of a nucleic acid encoding OGTA001, such as by polymerase chain reaction (see, e.g., Innis et al., 1990, PCR Protocols, Academic Press, Inc., San Diego, Calif.), ligase chain reaction (see EP 320,308) use of Qβ replicase, cyclic probe reaction, or other methods known in the art.

A kit can optionally further comprise a predetermined amount of OGTA001 or a nucleic acid encoding OGTA001, e.g., for use as a standard or control.

Use in Clinical Studies

The diagnostic methods and compositions of the present invention can assist in monitoring a clinical study, e.g. to evaluate drugs for therapy of colorectal cancer. In one embodiment, candidate molecules are tested for their ability to restore OGTA001 levels in a subject having colorectal cancer to levels found in subjects free from colorectal cancer or, in a treated subject, to preserve OGTA001 levels at or near non-colorectal cancer values.

In another embodiment, the methods and compositions of the present invention are used to screen candidates for a clinical study to identify individuals having colorectal cancer; such individuals can then be excluded from the study or can be placed in a separate cohort for treatment or analysis.

Production of Protein of the Invention and Corresponding Nucleic Acid

A DNA of the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al's method (DNA Research Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined. Furthermore, databases of known genes are searched for homology using the thus obtained terminal nucleotide sequences as queries. The entire nucleotide sequence of a clone revealed to be novel as a result is determined. In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from colorectal tissue. Such a DNA may also be a synthetic DNA or the like. Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptide consisting of an amino acid sequence that is substantially identical to the amino acid sequence of OGTA001 or DNA encoding the above polypeptide consisting of an amino acid sequence derived from the amino acid sequence of OGTA001 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present invention are preferably conserved.

Furthermore, examples of DNA of the present invention include DNA comprising a nucleotide sequence that encodes the amino acid sequence of OGTA001 and DNA hybridizing under stringent conditions to the DNA and encoding a polypeptide (protein) having biological activity (function) equivalent to the function of the polypeptide consisting of the amino acid sequence of OGTA001. Under such conditions, an example of such DNA capable of hybridizing to DNA comprising the nucleotide sequence that encodes the amino acid sequence of OGTA001 is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

Where it is provided for use with the methods of the invention OGTA001 is preferably provided in isolated form. More preferably the OGTA001 polypeptide has been purified to at least to some extent. OGTA001 polypeptide may be provided in substantially pure form, that is to say free, to a substantial extent, from other proteins. OGTA001 polypeptide can also be produced using recombinant methods, synthetically produced or produced by a combination of these methods. OGTA001 can be easily prepared by any method known by persons skilled in the art, which involves producing an expression vector containing a DNA of the present invention or a gene containing a DNA of the present invention, culturing a transformant transformed using the expression vector, generating and accumulating a polypeptide of the present invention or a recombinant protein containing the polypeptide, and then collecting the resultant.

Recombinant OGTA001 polypeptide may be prepared by processes well known in the art from genetically engineered host cells comprising expression systems. Accordingly, the present invention also relates to expression systems which comprise an OGTA001 polypeptide or nucleic acid, to host cells which are genetically engineered with such expression systems and to the production of OGTA001 polypeptide by recombinant techniques. For recombinant OGTA001 polypeptide production, host cells can be genetically engineered to incorporate expression systems or portions thereof for nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N.Y., 1989).

As host cells, for example, bacteria of the genus *Escherichia, Streptococci, Staphylococci, Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used. As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127, 3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda]

phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an 1 pp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRα promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the OGTA001 polypeptide to allow secretion of the translated protein into the lumen of the endoplasmic reticulum, the periplasmic space or the extracellular environment. These signals may be endogenous to the OGTA001 polypeptide or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If an OGTA001 polypeptide is to be expressed for use in cell-based screening assays, it is preferred that the polypeptide be produced at the cell surface. In this event, the cells may be harvested prior to use in the screening assay. If the OGTA001 polypeptide is secreted into the medium, the medium can be recovered in order to isolate said polypeptide. If produced intracellularly, the cells must first be lysed before the OGTA001 polypeptide is recovered.

OGTA001 polypeptide can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to an OGTA001 polypeptide can be used to deplete a sample comprising an OGTA001 polypeptide of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art may be used for refolding to regenerate native or active conformations of the OGTA001 polypeptide when the polypeptide has been denatured during isolation and or purification. In the context of the present invention, OGTA001 polypeptide can be obtained from a biological sample from any source, such as and without limitation, a blood sample or tissue sample, e.g. a colorectal tissue sample.

OGTA001 polypeptide may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

An additional sequence that may provide stability during recombinant production may also be used. Such sequences may be optionally removed as required by incorporating a cleavable sequence as an additional sequence or part thereof. Thus, an OGTA001 polypeptide may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to OGTA001

According to those in the art, there are three main types of affinity reagent—monoclonal antibodies, phage display antibodies and small molecules such as Affibodies, Domain Antibodies (dAbs), Nanobodies or Unibodies. In general in applications according to the present invention where the use of antibodies is stated, other affinity reagents (e.g. Affibodies, domain antibodies, Nanobodies or Unibodies) may be employed.

Production of Antibodies to OGTA001

According to the invention OGTA001, an OGTA001 analog, an OGTA001-related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody." Antibodies of the invention include, but are not limited to polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The immunoglobulin molecules of the invention can be of any class (e.g., IgG, IgE, IgM, IgD and IgA) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least $10^6$ M$^{-1}$. Preferred antibodies bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$.

Affinity is calculated as $K_d=k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c).

The data are graphed using the Scatchard equation: r/c=K(n−r):

where
r=moles of bound ligand/mole of receptor at equilibrium;
c=free ligand concentration at equilibrium;
K=equilibrium association constant; and
n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1\times10^{-6}$ moles/liter, is more preferably at least about $1\times10^{-7}$ moles/liter, is even more preferably at least about $1\times10^{-8}$ moles/liter, is yet even more preferably at least about $1\times10^{-9}$ moles/liter, and is most preferably at least about $1\times10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

In one embodiment, antibodies that recognize gene products of genes encoding OGTA001 are publicly available. In another embodiment, methods known to those skilled in the art are used to produce antibodies that recognize OGTA001, an OGTA001 analog, an OGTA001-related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of OGTA001 are produced. In a specific embodiment, hydrophilic fragments of OGTA001 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of OGTA001, one may assay generated hybridomas for a product which binds to an OGTA001 fragment containing such domain. For selection of an antibody that specifically binds a first OGTA001 homolog but which does not specifically bind to (or binds less avidly to) a second OGTA001 homolog, one can select on the basis of positive binding to the first OGTA001 homolog and a lack of binding to (or reduced binding to) the second OGTA001 homolog. Similarly, for selection of an antibody that specifically binds OGTA001 but which does not specifically bind to (or binds less avidly to) a different isoform of the same protein (such as a different glycoform having the same core peptide as OGTA001), one can select on the basis of positive binding to OGTA001 and a lack of binding to (or reduced binding to) the different isoform (e.g., a different glycoform). Thus, the present invention provides an antibody (preferably a monoclonal antibody) that binds with greater affinity (preferably at least 2-fold, more preferably at least 5-fold, still more preferably at least 10-fold greater affinity) to OGTA001 than to a different isoform or isoforms (e.g., glycoforms) of OGTA001.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to OGTA001, a fragment of OGTA001, an OGTA001-related polypeptide, or a fragment of an OGTA001-related polypeptide. For example, one way is to purify polypeptides of interest or to synthesize the polypeptides of interest using, e.g., solid phase peptide synthesis methods well known in the art. See, e.g., *Guide to Protein Purification*, Murray P. Deutcher, ed., *Meth. Enzymol. Vol* 182 (1990); Solid Phase Peptide Synthesis, Greg B. Fields ed., *Meth. Enzymol. Vol* 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. The Preferred Technology described herein in Example 1 provides isolated OGTA001 suitable for such immunization. If OGTA001 is purified by gel electrophoresis, OGTA001 can be used for immunization with or without prior extraction from the polyacrylamide gel. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *corynebacterium parvum*. Additional adjuvants are also well known in the art.

For preparation of monoclonal antibodies (mAbs) directed toward OGTA001, a fragment of OGTA001, an OGTA001-related polypeptide, or a fragment of an OGTA001-related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g., human-mouse chimeras). A chimeric antibody is a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239: 1534; and Beidler et al., 1988, J. Immunol. 141:4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g., all or a portion of OGTA001. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Bio/technology 12:899-903).

The antibodies of the present invention can also be generated by the use of phage display technology to produce and screen libraries of polypeptides for binding to a selected target. See, e.g., Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057, 098, which is hereby incorporated in its entirety, including all tables, figures, and claims. In particular, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121: 210.

The invention provides functionally active fragments, derivatives or analogs of the anti-OGTA001 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g., a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of OGTA001, e.g., for imaging this protein, measuring levels thereof in appropriate physiological samples, in diagnostic methods, etc.

Production of Affibodies to OGTA001

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J. Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

Production of Domain Antibodies to OGTA001

References to antibodies herein embrace references to Domain Antibodies. Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human $V_H$ and $V_L$ dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to OGTA001

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$), Importantly, the cloned and isolated VHH domain is a perfectly stable polypeptide harbouring the full antigen-binding capacity of the original heavy-chain antibody. Nanobodies have a high homology with the VH domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts, Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), moulds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanocione method (see e.g. WO 06/079372, which is herein incorporated bye reference in its entirety) is a proprietary method for generating Nanobodies against a desired target, based on automated high-throughout selection of B-cells.

Production of Unibodies to OGTA001

UniBody is a new proprietary antibody technology that creates a stable, smaller antibody format with an anticipated longer therapeutic window than current small antibody formats. IgG4 antibodies are considered inert and thus do not interact with the immune system. Genmab modified fully human IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to disease targets and the UniBody therefore binds univalently to only one site on target cells. This univalent binding does not stimulate cancer cells to grow like bivalent antibodies might and opens the door for treatment of some types of cancer which ordinary antibodies cannot treat.

The UniBody is about half the size of a regular IgG4 antibody. This small size can be a great benefit when treating some forms of cancer, allowing for better distribution of the molecule over larger solid tumors and potentially increasing efficacy.

Fabs typically do not have a very long half-life. UniBodies, however, were cleared at a similar rate to whole IgG4 antibodies and were able to bind as well as whole antibodies and antibody fragments in pre-clinical studies. Other antibodies primarily work by killing the targeted cells whereas UniBodies only inhibit or silence the cells.

Further details of Unibodies may be obtained by reference to patent WO2007/059782, which is herein incorporated by reference in its entirety.

Expression of Affinity Reagents

Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g., PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCR based methods, etc.

In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g., humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as Escherichia coli, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, Gene 45:101; Cockett et al., 1990, Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited to, the E. coli expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system) may be utilized.

As discussed above, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g., neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g., ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitrilo-acetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies. Animal antibodies may be raised in animals using the human protein (e.g. OGTA001) as immunogen. Humanisation typically involves grafting CDRs identified thereby into human framework regions. Normally some subsequent retromutation to optimize the conformation of chains is required. Such processes are known to persons skilled in the art.

Expression of Affibodies

The construction of affibodies has been described elsewhere (Ronnmark J, Gronlund H, Uhle'n, M., Nygren P. A°, Human immunoglobulin A (IgA)-specific ligands from combinatorial engineering of protein A, 2002, Eur. J. Biochem. 269, 2647-2655.), including the construction of affibody phage display libraries (Nord, K., Nilsson, J., Nilsson, B., Uhle'n, M. & Nygren, P. A°, A combinatorial library of an a-helical bacterial receptor domain, 1995, Protein Eng. 8, 601-608. Nord, K., Gunneriusson, E., Ringdahl, J., Sta°hl, S., Uhle'n, M. & Nygren, P. A°, Binding proteins selected from combinatorial libraries of an a-helical bacterial receptor domain, 1997, Nat. Biotechnol. 15, 772-777.)

The biosensor analyses to investigate the optimal affibody variants using biosensor binding studies has also been described elsewhere (Ronnmark J, Gronlund H, Uhle' n, M., Nygren P. A°, Human immunoglobulin A (IgA)-specific ligands from combinatorial engineering of protein A, 2002, Eur. J. Biochem. 269, 2647-2655.).

Conjugated Affinity Reagents

In a preferred embodiment, anti-OGTA001 affinity reagents such as antibodies or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and non-radioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc. $^{68}$Ga may also be employed.

Anti-OGTA001 antibodies or fragments thereof can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, -interferon, -interferon, nerve growth factor, platelet derived growth factor, tissue plasminogen activator, a thrombotic agent or an anti-angiogenic agent, e.g., angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

Diagnosis of Colorectal Cancer

In accordance with the present invention, test samples of colorectal tissue, serum, plasma or urine obtained from a subject suspected of having or known to have colorectal cancer can be used for diagnosis or monitoring. In one embodiment, a change in the abundance of OGTA001 in a test sample relative to a control sample (from a subject or subjects free from colorectal cancer) or a previously determined reference range indicates the presence of colorectal cancer. In another embodiment, the relative abundance of OGTA001 in a test sample compared to a control sample or a previously determined reference range indicates a subtype of colorectal cancer (e.g., familial or sporadic colorectal cancer). In yet another embodiment, the relative abundance of OGTA001 in a test sample relative to a control sample or a previously determined reference range indicates the degree or severity of colorectal cancer (e.g., the likelihood for metastasis). In any of the aforesaid methods, detection of OGTA001 may optionally be combined with detection of one or more of additional biomarkers for colorectal cancer. Any suitable method in the art can be employed to measure the level of OGTA001, including but not limited to the Preferred Technologies described herein, kinase assays, immunoassays to detect and/or visualize the OGTA001 (e.g., Western blot, immunoprecipitation followed by sodium dodecyl sulfate polyacrylamide gel electrophoresis, immunocytochemistry, etc.). In a further embodiment, a change in the abundance of mRNA encoding OGTA001 in a test sample relative to a control sample or a previously determined reference range indicates the presence of colorectal cancer. Any suitable hybridization assay can be used to detect OGTA001 expression by detecting and/or visualizing mRNA encoding the OGTA001 (e.g., Northern assays, dot blots, in situ hybridization, etc.).

In another embodiment of the invention, labeled antibodies (or other affinity reagents such as Affibodies, Nanobodies or Unibodies), derivatives and analogs thereof, which specifically bind to OGTA001 can be used for diagnostic purposes to detect, diagnose, or monitor colorectal cancer. Preferably, colorectal cancer is detected in an animal, more preferably in a mammal and most preferably in a human.

Screening Assays

The invention provides methods for identifying agents (e.g., candidate compounds or test compounds) that bind to OGTA001 or have a stimulatory or inhibitory effect on the expression or activity of OGTA001. The invention also provides methods of identifying agents, candidate compounds or test compounds that bind to an OGTA001-related polypeptide or an OGTA001 fusion protein or have a stimulatory or inhibitory effect on the expression or activity of an OGTA001-related polypeptide or an OGTA001 fusion protein. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g., presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310), each of which is incorporated herein in its entirety by reference.

In one embodiment, agents that interact with (i.e., bind to) OGTA001, an OGTA001 fragment (e.g. a functionally active fragment), an OGTA001-related polypeptide, a fragment of an OGTA001-related polypeptide, or an OGTA001 fusion protein are identified in a cell-based assay system. In accordance with this embodiment, cells expressing OGTA001, a fragment of an OGTA001, an OGTA001-related polypeptide, a fragment of the OGTA001-related polypeptide, or an OGTA001 fusion protein are contacted with a candidate compound or a control compound and the ability of the candidate compound to interact with OGTA001 is determined. If desired, this assay may be used to screen a plurality (e.g. a library) of candidate compounds. The cell, for example, can be of prokaryotic origin (e.g., E. coli) or eukaryotic origin (e.g., yeast or mammalian). Further, the cells can express OGTA001, a fragment of OGTA001, an OGTA001-related polypeptide, a fragment of the OGTA001-related polypeptide, or an OGTA001 fusion protein endogenously or be genetically engineered to express OGTA001, a fragment of OGTA001, an OGTA001-related polypeptide, a fragment of the OGTA001-related polypeptide, or an OGTA001 fusion protein. In certain instances, OGTA001, a fragment of the OGTA001, an OGTA001-related polypeptide, a fragment of the OGTA001-related polypeptide, or an OGTA001 fusion protein or the candidate compound is labeled, for example with a radioactive label (such as $^{32}$P, $^{35}$S, and $^{125}$I) or a fluorescent label (such as fluorescein isothiocyanate, rhodamine, phycoerythrin, phycocyanin, allophycocyanin, o-phthaldehyde or fluorescamine) to enable detection of an interaction between OGTA001 and a candidate compound. The ability of the candidate compound to interact directly or indirectly with OGTA001, a fragment of OGTA001, an OGTA001-related polypeptide, a fragment of an OGTA001-related polypeptide, or an OGTA001 fusion protein can be determined by methods known to those of skill in the art. For example, the interaction between a candidate compound and OGTA001, an OGTA001-related polypeptide, a fragment of an OGTA001-related polypeptide, or an OGTA001 fusion protein can be determined by flow cytometry, a scintillation assay, immunoprecipitation or western blot analysis.

In another embodiment, agents that interact with (i.e., bind to) OGTA001, an OGTA001 fragment (e.g., a functionally active fragment), an OGTA001-related polypeptide, a fragment of an OGTA001-related polypeptide, or an OGTA001 fusion protein are identified in a cell-free assay system. In accordance with this embodiment, a native or recombinant OGTA001 or fragment thereof, or a native or recombinant OGTA001-related polypeptide or fragment thereof, or an OGTA001-fusion protein or fragment thereof, is contacted with a candidate compound or a control compound and the ability of the candidate compound to interact with OGTA001 or OGTA001-related polypeptide, or OGTA001 fusion protein is determined. If desired, this assay may be used to screen a plurality (e.g. a library) of candidate compounds. Preferably, OGTA001, an OGTA001 fragment, an OGTA001-related polypeptide, a fragment of an OGTA001-related polypeptide, or an OGTA001-fusion protein is first immobilized, by, for example, contacting OGTA001, an OGTA001 fragment, an OGTA001-related polypeptide, a fragment of an OGTA001-related polypeptide, or an OGTA001 fusion protein with an immobilized antibody (or other affinity reagent such as an Affibody, Nanobody or Unibody) which specifically recognizes and binds it, or by contacting a purified preparation of OGTA001, an OGTA001 fragment, an OGTA001-related polypeptide, a fragment of an OGTA001-related polypeptide, or an OGTA001 fusion protein with a surface designed to bind proteins. OGTA001, an OGTA001 fragment, an OGTA001-related polypeptide, a fragment of an OGTA001-related polypeptide, or an OGTA001 fusion protein may be partially or completely purified (e.g., partially or completely free of other polypeptides) or part of a cell lysate. Further, OGTA001, an OGTA001 fragment, an OGTA001-related polypeptide, a fragment of an OGTA001-related polypeptide may be a fusion protein comprising OGTA001 or a biologically active portion thereof, or OGTA001-related polypeptide and a domain such as glutathionine-5-transferase. Alternatively, OGTA001, an OGTA001 fragment, an OGTA001-related polypeptide, a fragment of an OGTA001-related polypeptide or an OGTA001 fusion protein can be biotinylated using techniques well known to those of skill in the art (e.g., biotinylation kit, Pierce Chemicals; Rockford, Ill.). The ability of the candidate compound to interact with OGTA001, an OGTA001 fragment, an OGTA001-related polypeptide, a fragment of an OGTA001-related polypeptide, or an OGTA001 fusion protein can be determined by methods known to those of skill in the art.

In another embodiment, a cell-based assay system is used to identify agents that bind to or modulate the activity of a protein, such as an enzyme, or a biologically active portion thereof, which is responsible for the production or degradation of OGTA001 or is responsible for the post-translational modification of OGTA001. In a primary screen, a plurality (e.g., a library) of compounds are contacted with cells that naturally or recombinantly express: (i) OGTA001, an isoform of OGTA001, an OGTA001 homolog, an OGTA001-related polypeptide, an OGTA001 fusion protein, or a biologically active fragment of any of the foregoing; and (ii) a protein that is responsible for processing of OGTA001, the OGTA001 isoform, the OGTA001 homolog, the OGTA001-related polypeptide, the OGTA001 fusion protein, or fragment in order to identify compounds that modulate the production, degradation, or post-translational modification of OGTA001, the OGTA001 isoform, the OGTA001 homolog, the OGTA001-related polypeptide, the OGTA001 fusion protein or fragment. If desired, compounds identified in the primary screen can then be assayed in a secondary screen against cells naturally or recombinantly expressing OGTA001. The ability of the candidate compound to modulate the production, degradation or post-translational modification of OGTA001, isoform, homolog, OGTA001-related polypeptide, or OGTA001 fusion protein can be determined by methods known to those of skill in the art, including without limitation, flow cytometry, a scintillation assay, immunoprecipitation and western blot analysis.

In another embodiment, agents that competitively interact with (i.e., bind to) OGTA001, an OGTA001 fragment, an OGTA001-related polypeptide, a fragment of an OGTA001-related polypeptide, or an OGTA001 fusion protein are identified in a competitive binding assay. In accordance with this embodiment, cells expressing OGTA001, an OGTA001 fragment, an OGTA001-related polypeptide, a fragment of an OGTA001-related polypeptide, or an OGTA001 fusion protein are contacted with a candidate compound and a compound known to interact with OGTA001, an OGTA001 fragment, an OGTA001-related polypeptide, a fragment of an OGTA001-related polypeptide or an OGTA001 fusion protein; the ability of the candidate compound to preferentially interact with OGTA001, the OGTA001 fragment, the OGTA001-related polypeptide, the fragment of the OGTA001-related polypeptide, or the OGTA001 fusion protein is then determined. Alternatively, agents that preferentially interact with (i.e., bind to) OGTA001, an OGTA001 fragment, an OGTA001-related polypeptide or fragment of an OGTA001-related polypeptide are identified in a cell-free assay system by contacting OGTA001, an OGTA001 fragment, an OGTA001-related polypeptide, a fragment of an OGTA001-related polypeptide, or an OGTA001 fusion protein with a candidate compound and a compound known to interact with OGTA001, the OGTA001-related polypeptide or the OGTA001 fusion protein. As stated above, the ability of the candidate compound to interact with OGTA001, an OGTA001 fragment, an OGTA001-related polypeptide, a fragment of an OGTA001-related polypeptide, or an OGTA001 fusion protein can be determined by methods known to those of skill in the art. These assays, whether cell-based or cell-free, can be used to screen a plurality (e.g., a library) of candidate compounds.

In another embodiment, agents that modulate (i.e., upregulate or downregulate) the expression or activity of OGTA001, or an OGTA001-related polypeptide are identified by contacting cells (e.g., cells of prokaryotic origin or eukaryotic origin) expressing OGTA001, or the OGTA001-related polypeptide with a candidate compound or a control compound (e.g., phosphate buffered saline (PBS)) and determining the expression of OGTA001, the OGTA001-related polypeptide, or the OGTA001 fusion protein, mRNA encoding OGTA001, or mRNA encoding the OGTA001-related polypeptide. The level of expression of OGTA001, the OGTA001-related polypeptide, mRNA encoding OGTA001, or mRNA encoding the OGTA001-related polypeptide in the presence of the candidate compound is compared to the level of expression of OGTA001, the OGTA001-related polypeptide, mRNA encoding OGTA001, or mRNA encoding the OGTA001-related polypeptide in the absence of the candidate compound (e.g., in the presence of a control compound). The candidate compound can then be identified as a modulator of the expression of OGTA001, or the OGTA001-related polypeptide based on this comparison. For example, when expression of OGTA001 or mRNA is significantly greater in the presence of the candidate compound than in its absence, the candidate compound is identified as a stimulator of expression of OGTA001 or mRNA. Alternatively, when expression of OGTA001 or mRNA is significantly less in the presence of the candidate compound than in its absence, the candidate compound is identified as an inhibitor of the expression of OGTA001 or mRNA. The level of expression of OGTA001 or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of OGTA001 or an OGTA001-related polypeptide are identified by contacting a preparation containing OGTA001 or the OGTA001-related polypeptide or cells (e.g., prokaryotic or eukaryotic cells) expressing OGTA001 or the OGTA001-related polypeptide with a test compound or a control compound and determining the ability of the test compound to modulate (e.g., stimulate or inhibit) the activity of OGTA001 or the OGTA001-related polypeptide. The activity of OGTA001 or an OGTA001-related polypeptide can be assessed by detecting induction of a cellular signal transduction pathway of OGTA001 or the OGTA001-related polypeptide (e.g., intracellular $Ca^{2+}$, diacylglycerol, IP3, etc.), detecting catalytic or enzymatic activity of the target on a suitable substrate, detecting the induction of a reporter gene (e.g., a regulatory element that is responsive to OGTA001 or an OGTA001-related polypeptide and is operably linked to a nucleic acid encoding a detectable marker, e.g., luciferase), or detecting a cellular response, for example, cellular differentiation, or cell proliferation. Based on the present description, techniques known to those of skill in the art can be used for measuring these activities (see, e.g., U.S. Pat. No. 5,401,639, which is incorporated herein by reference). The candidate compound can then be identified as a modulator of the activity of OGTA001 or an OGTA001-related polypeptide by comparing the effects of the candidate compound to the control compound. Suitable control compounds include phosphate buffered saline (PBS) and normal saline (NS).

In another embodiment, agents that modulate (i.e., upregulate or downregulate) the expression, activity or both the expression and activity of OGTA001 or an OGTA001-related polypeptide are identified in an animal model. Examples of suitable animals include, but are not limited to, mice, rats, rabbits, monkeys, guinea pigs, dogs and cats. Preferably, the animal used represent a model of colorectal cancer (e.g., xenografts of human colorectal cancer cell lines such as MDA-MB-345 in oestrogen-deprived Severe Combined Immunodeficient (SCID) mice, Eccles et al. 1994 Cell Biophysics 24/25, 279). These can be utilized to test compounds that modulate OGTA001 levels, since the pathology exhibited in these models is similar to that of colorectal cancer. In accordance with this embodiment, the test compound or a control compound is administered (e.g., orally, rectally or parenterally such as intraperitoneally or intravenously) to a suitable animal and the effect on the expression, activity or both expression and activity of OGTA001 or an OGTA001-related polypeptide is determined. Changes in the expression of OGTA001 or an OGTA001-related polypeptide can be assessed by the methods outlined above.

In yet another embodiment, OGTA001 or an OGTA001-related polypeptide is used as a "bait protein" in a two-hybrid assay or three hybrid assay to identify other proteins that bind to or interact with OGTA001 or an OGTA001-related polypeptide (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by OGTA001 as, for example, upstream or downstream elements of a signaling pathway involving OGTA001.

This invention further provides novel agents identified by the above-described screening assays and uses thereof for treatments as described herein. In addition, the invention also provides the use of an agent which interacts with, or modulates the activity of, OGTA001 in the manufacture of a medicament for the treatment of colorectal cancer.

Therapeutic Use of OGTA001

The invention provides for treatment or prevention of various diseases and disorders by administration of a therapeutic compound. Such compounds include but are not limited to: OGTA001, OGTA001 analogs, OGTA001-related polypeptides and derivatives (including fragments) thereof; antibodies (or other affinity reagents such as Affibodies, Nanobodies or Unibodies) to the foregoing; nucleic acids encoding OGTA001, OGTA001 analogs, OGTA001-related polypeptides and fragments thereof; antisense nucleic acids to a gene encoding OGTA001 or an OGTA001-related polypeptide; and modulator (e.g., agonists and antagonists) of a gene encoding OGTA001 or an OGTA001-related polypeptide. An important feature of the present invention is the identification of genes encoding OGTA001 involved in colorectal cancer. Colorectal cancer can be treated (e.g. to ameliorate symptoms or to retard onset or progression) or prevented by administration of a therapeutic compound that reduces function or expression of OGTA001 in the serum or tissue of subjects having colorectal cancer.

In one embodiment, one or more antibodies (or other affinity reagents such as Affibodies, Nanobodies or Unibodies) each specifically binding to OGTA001 are administered alone or in combination with one or more additional therapeutic compounds or treatments.

Preferably, a biological product such as an antibody (or other affinity reagent such as an Affibody, Nanobody or Unibody) is allogeneic to the subject to which it is administered. In a preferred embodiment, a human OGTA001 or a human OGTA001-related polypeptide, a nucleotide sequence encoding a human OGTA001 or a human OGTA001-related polypeptide, or an antibody (or other affinity reagent such as an Affibody, Nanobody or Unibody) to a human OGTA001 or a human OGTA001-related polypeptide, is administered to a human subject for therapy (e.g. to ameliorate symptoms or to retard onset or progression) or prophylaxis.

Without being limited by theory, it is conceived that the therapeutic activity of antibodies (or other affinity reagents such as Affibodies, Nanobodies or Unibodies) which specifically bind to OGTA001 may be achieved through the phenomenon of Antibody-Dependent Cell-mediated Cytotoxicity (ADCC) (see e.g. Janeway Jr. C. A. et al., Immunobiology, 5th ed., 2001, Garland Publishing, ISBN 0-8153-3642-X; Pier G. B. et al., Immunology, Infection, and Immunity, 2004, p246-5; Albanell J. et al., Advances in Experimental Medicine and Biology, 2003, 532:p2153-68 and Weng, W.-K. et al., Journal of Clinical Oncology, 2003, 21:p 3940-3947).

Treatment and Prevention of Colorectal Cancer

Colorectal cancer is treated or prevented by administration to a subject suspected of having or known to have colorectal cancer or to be at risk of developing colorectal cancer of a compound that modulates (i.e., increases or decreases) the level or activity (i.e., function) of OGTA001 that is differentially present in the serum or tissue of subjects having colorectal cancer compared with serum or tissue of subjects free from colorectal cancer. In one embodiment, colorectal cancer is treated or prevented by administering to a subject suspected of having or known to have colorectal cancer or to be at risk of developing colorectal cancer a compound that upregulates (i.e., increases) the level or activity (i.e., function) of OGTA001 that are decreased in the serum or tissue of subjects having colorectal cancer. Examples of such a compound include, but are not limited to, OGTA001 antisense oligonucleotides, ribozymes, antibodies (or other affinity reagents such as Affibodies, Nanobodies or Unibodies) directed against OGTA001, and compounds that inhibit the enzymatic activity of OGTA001. Other useful compounds e.g., OGTA001 antagonists and small molecule OGTA001 antagonists, can be identified using in vitro assays.

Colorectal cancer is also treated or prevented by administration to a subject suspected of having or known to have colorectal cancer or to be at risk of developing colorectal cancer of a compound that downregulates the level or activity (i.e. function) of OGTA001 that are increased in the serum or tissue of subjects having colorectal cancer. Examples of such a compound include but are not limited to: OGTA001, OGTA001 fragments and OGTA001-related polypeptides; nucleic acids encoding OGTA001, an OGTA001 fragment and an OGTA001-related polypeptide (e.g., for use in gene therapy); and, for those OGTA001 or OGTA001-related polypeptides with enzymatic activity, compounds or molecules known to modulate that enzymatic activity. Other compounds that can be used, e.g., OGTA001 agonists, can be identified using in in vitro assays.

In a preferred embodiment, therapy or prophylaxis is tailored to the needs of an individual subject. Thus, in specific embodiments, compounds that promote the level or function of OGTA001 are therapeutically or prophylactically administered to a subject suspected of having or known to have colorectal cancer, in whom the levels or functions of OGTA001 are absent or are decreased relative to a control or normal reference range. In further embodiments, compounds that promote the level or function of OGTA001 are therapeutically or prophylactically administered to a subject suspected of having or known to have colorectal cancer in whom the levels or functions of OGTA001 are increased relative to a control or to a reference range. In further embodiments, compounds that decrease the level or function of OGTA001 are therapeutically or prophylactically administered to a subject suspected of having or known to have colorectal cancer in whom the levels or functions of OGTA001 are increased relative to a control or to a reference range. In further embodiments, compounds that decrease the level or function of OGTA001 are therapeutically or prophylactically administered to a subject suspected of having or known to have colorectal cancer in whom the levels or functions of OGTA001 are decreased relative to a control or to a reference range. The change in OGTA001 function or level due to the administration of such compounds can be readily detected, e.g., by obtaining a sample (e.g., blood or urine) and assaying in vitro the levels or activities of OGTA001, or the levels of mRNAs encoding OGTA001, or any combination of the foregoing. Such assays can be performed before and after the administration of the compound as described herein.

The compounds of the invention include but are not limited to any compound, e.g., a small organic molecule, protein, peptide, antibody (or other affinity reagent such as an Affibody, Nanobody or Unibody), nucleic acid, etc. that restores the OGTA001 profile towards normal. The compounds of the invention may be given in combination with any other chemotherapy drugs.

Vaccine Therapy

OGTA001 may be useful as antigenic material, and may be used in the production of vaccines for treatment or prophylaxis of colorectal cancer. Such material can be "antigenic" and/or "immunogenic". Generally, "antigenic" is taken to mean that the protein is capable of being used to raise antibodies (or other affinity reagents such as Affibodies, Nanobodies or Unibodies) or indeed is capable of inducing an antibody response in a subject or experimental animal. "Immunogenic" is taken to mean that the protein is capable of eliciting a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in-vitro setting eg a T-cell proliferation assay.

The skilled person will appreciate that homologues or derivatives of OGTA001 will also find use as antigenic/immunogenic material. Thus, for instance proteins which include one or more additions, deletions, substitutions or the like are encompassed by the present invention. In addition, it may be possible to replace one amino acid with another of similar "type". For instance, replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) with the proteins or polypeptides described herein are provided. Preferably, homologues or derivatives having at least 70% similarity, more preferably at least 80% similarity, are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of OGTA001, or of homologues or derivatives thereof.

OGTA001, or antigenic fragments thereof, can be provided alone, as a purified or isolated preparation. They may be provided as part of a mixture with one or more other proteins or antigenic fragments thereof. In a further aspect, therefore, the invention provides an antigen composition comprising OGTA001 and/or one or more antigenic fragments thereof. Such a composition can be used for the detection and/or diagnosis of colorectal cancer.

In a sixth aspect, the present invention provides a method of detecting and/or diagnosing colorectal cancer which comprises:

bringing into contact with a sample to be tested an antigenic OGTA001, or an antigenic fragment thereof, or an antigen composition of the invention; and detecting the presence of antibodies (or other affinity reagents such as Affibodies, Nanobodies or Unibodies) to colorectal cancer.

In particular, the protein, antigenic fragment thereof or antigen composition of the present invention can be used to detect IgA, IgM or IgG antibodies. Suitably, the sample to be tested will be a biological sample, e.g. a sample of blood or saliva.

In a further aspect, the invention provides the use of an antigenic OGTA001, antigenic fragment thereof or an antigenic composition of the present invention in detecting and/or diagnosing colorectal cancer. Preferably, the detecting and/or diagnosing are carried out in vitro.

The antigenic OGTA001, antigenic fragments thereof or antigenic composition of the present invention can be provided as a kit for use in the in vitro detection and/or diagnosis of colorectal cancer. Thus, in a still further aspect, the present invention provides a kit for use in the detection and/or diagnosis of colorectal cancer, which kit comprises an antigenic OGTA001, an antigenic fragment thereof or an antigenic composition of the present invention.

In addition, the antigenic OGTA001, antigenic fragment thereof or antigen composition of the invention can be used to induce an immune response against colorectal cancer. Thus, in a yet further aspect, the invention provides the use of an antigenic OGTA001, an antigenic fragment thereof or an antigen composition of the invention in medicine.

In a further aspect, the present invention provides a composition capable of eliciting an immune response in a subject, which composition comprises OGTA001, an antigenic fragment thereof, or an antigen composition of the invention. Suitably, the composition will be a vaccine composition, optionally comprising one or more suitable adjuvants. Such a vaccine composition may be either a prophylactic or therapeutic vaccine composition.

The vaccine compositions of the invention can include one or more adjuvants. Examples well-known in the art include inorganic gels, such as aluminium hydroxide, and water-in-oil emulsions, such as incomplete Freund's adjuvant. Other useful adjuvants will be well known to the skilled person.

In yet further aspects, the present invention provides:

(a) the use of OGTA001, an antigenic fragment thereof, or an antigen composition of the invention in the preparation of an immunogenic composition, preferably a vaccine;

(b) the use of such an immunogenic composition in inducing an immune response in a subject; and (c) a method for the treatment or prophylaxis of colorectal cancer in a subject, or of vaccinating a subject against colorectal cancer which comprises the step of administering to the subject an effective amount of OGTA001, at least one antigenic fragment thereof or an antigen composition of the invention, preferably as a vaccine.

In a specific embodiment, a preparation of OGTA001 or OGTA001 peptide fragments is used as a vaccine for the treatment of colorectal cancer. Such preparations may include adjuvants or other vehicles.

In another embodiment, a preparation of oligonucleotides comprising 10 or more consecutive nucleotides complementary to a nucleotide sequence encoding OGTA001 or OGTA001 peptide fragments is used as vaccines for the treatment of colorectal cancer. Such preparations may include adjuvants or other vehicles.

Inhibition of OGTA001 to Treat Colorectal Cancer

In one embodiment of the invention, colorectal cancer is treated or prevented by administration of a compound that antagonizes (inhibits) the level(s) and/or function(s) of OGTA001 which are elevated in the serum or tissue of subjects having colorectal cancer as compared with serum or tissue of subjects free from colorectal cancer.

Compounds useful for this purpose include but are not limited to anti-OGTA001 antibodies (or other affinity reagents such as Affibodies, Nanobodies or Unibodies, and fragments and derivatives containing the binding region thereof), OGTA001 antisense or ribozyme nucleic acids, and nucleic acids encoding dysfunctional OGTA001 that are used to "knockout" endogenous OGTA001 function by homologous recombination (see, e.g., Capecchi, 1989, *Science* 244: 1288-1292). Other compounds that inhibit OGTA001 function can be identified by use of known in vitro assays, e.g., assays for the ability of a test compound to inhibit binding of OGTA001 to another protein or a binding partner, or to inhibit a known OGTA001 function. Preferably such inhibition is assayed in vitro or in cell culture, but genetic assays may also be employed. The Preferred Technologies can also be used to detect levels of OGTA001 before and after the administration of the compound. Preferably, suitable in vitro or in vivo assays are utilized to determine the effect of a specific compound and whether its administration is indicated for treatment of the affected tissue, as described in more detail below.

In a specific embodiment, a compound that inhibits OGTA001 function is administered therapeutically or prophylactically to a subject in whom an increased serum or tissue level or functional activity of OGTA001 (e.g., greater than the normal level or desired level) is detected as compared with serum or tissue of subjects free from colorectal cancer or a predetermined reference range. Methods standard in the art can be employed to measure the increase in OGTA001 level or function, as outlined above. Preferred OGTA001 inhibitor compositions include small molecules, i.e., molecules of 1000 daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of colorectal cancer. Test compounds can be assayed for their ability to restore OGTA001 levels in a subject having colorectal cancer towards levels found in subjects free from colorectal cancer or to produce similar changes in experimental animal models of colorectal cancer. Compounds able to restore OGTA001 levels in a subject having colorectal cancer towards levels found in subjects free from colorectal cancer or to produce similar changes in experimental animal models of colorectal cancer can be used as lead compounds for further drug discovery, or used therapeutically. OGTA001 expression can be assayed by the Preferred Technologies, immunoassays, gel electrophoresis followed by visualization, detection of OGTA001 activity, or any other method taught herein or known to those skilled in the art. Such assays can be used to screen candidate drugs, in clinical monitoring or in drug development, where abundance of OGTA001 can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of colorectal cancer include, but are not limited to xenografts of human colorectal cancer cell lines such as MDA-MB-435 in oestrogen-deprived Severe Combined Immunodeficient (SCID) mice (Eccles et al., 1994 Cell Biophysics 24/25, 279). These can be utilized to test compounds that modulate OGTA001 levels, since the pathology exhibited in these models is similar to that of colorectal cancer. It is also apparent to the skilled artisan that based upon the present disclosure, transgenic animals can be produced with "knock-out" mutations of the gene or genes encoding OGTA001. A "knock-out" mutation of a gene is a mutation that causes the mutated gene to not be expressed, or expressed in an aberrant form or at a low level, such that the activity associated with the gene product is nearly or entirely absent. Preferably, the transgenic animal is a mammal; more preferably, the transgenic animal is a mouse.

In one embodiment, test compounds that modulate the expression of OGTA001 are identified in non-human animals (e.g., mice, rats, monkeys, rabbits, and guinea pigs), preferably non-human animal models for colorectal cancer, expressing OGTA001. In accordance with this embodiment, a test compound or a control compound is administered to the animals, and the effect of the test compound on expression of OGTA001 is determined. A test compound that alters the expression of OGTA001 can be identified by comparing the level of OGTA001 (or mRNA encoding the same) in an animal or group of animals treated with a test compound with the level of OGTA001 or mRNA in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of OGTA001 or a biologically active portion thereof are identified in non-human animals (e.g., mice, rats, monkeys, rabbits, and guinea pigs), preferably non-human animal models for colorectal cancer, expressing OGTA001. In accordance with this embodiment, a test compound or a control compound is administered to the animals, and the effect of a test compound on the activity of OGTA001 is determined. A test compound that alters the activity of OGTA001 can be identified by assaying animals treated with a control compound and animals treated with the test compound. The activity of OGTA001 can be assessed by detecting induction of a cellular second messenger of OGTA001 (e.g., intracellular $Ca^{2+}$, diacylglycerol, IP3, etc.), detecting catalytic or enzymatic activity of OGTA001 or binding partner thereof, detecting the induction of a reporter gene (e.g., a regulatory element that is responsive to OGTA001 operably linked to a nucleic acid encoding a detectable marker, such as luciferase or green fluorescent protein), or detecting a cellular response (e.g., cellular differentiation or cell proliferation). Techniques known to those of skill in the art can be utilized to detect changes in the activity of OGTA001 (see, e.g., U.S. Pat. No. 5,401,639, which is incorporated herein by reference).

In yet another embodiment, test compounds that modulate the level or expression of OGTA001 are identified in human subjects having colorectal cancer, preferably those having severe colorectal cancer. In accordance with this embodiment, a test compound or a control compound is administered to the human subject, and the effect of a test compound on OGTA001 expression is determined by analyzing the expression of OGTA001 or the mRNA encoding the same in a biological sample (e.g., serum, plasma, or urine). A test compound that alters the expression of OGTA001 can be identified by comparing the level of OGTA001 or mRNA encoding the same in a subject or group of subjects treated with a control compound to that in a subject or group of subjects treated with a test compound. Alternatively, alterations in the expression of OGTA001 can be identified by comparing the level of OGTA001 or mRNA encoding the same in a subject or group of subjects before and after the administration of a test compound. Techniques known to those of skill in the art can be used to obtain the biological sample and analyze the mRNA or protein expression. For example, the Preferred Technologies described herein can be used to assess changes in the level of OGTA001.

In another embodiment, test compounds that modulate the activity of OGTA001 are identified in human subjects having colorectal cancer, (preferably those with severe colorectal cancer). In this embodiment, a test compound or a control compound is administered to the human subject, and the effect of a test compound on the activity of OGTA001 is determined. A test compound that alters the activity of OGTA001 can be identified by comparing biological samples from subjects treated with a control compound to samples from subjects treated with the test compound. Alternatively, alterations in the activity of OGTA001 can be identified by comparing the activity of OGTA001 in a subject or group of subjects before and after the administration of a test compound. The activity of OGTA001 can be assessed by detecting in a biological sample (e.g., serum, plasma, or urine) induction of a cellular signal transduction pathway of OGTA001 (e.g., intracellular $Ca^{2+}$, diacylglycerol, IP3, etc.), catalytic or enzymatic activity of OGTA001 or a binding partner thereof, or a cellular response, for example, cellular differentiation, or cell proliferation. Techniques known to those of skill in the art can be used to detect changes in the induction of a second messenger of OGTA001 or changes in a cellular response. For example, RT-PCR can be used to detect changes in the induction of a cellular second messenger.

In a preferred embodiment, a test compound that changes the level or expression of OGTA001 towards levels detected in control subjects (e.g., humans free from colorectal cancer) is selected for further testing or therapeutic use. In another preferred embodiment, a test compound that changes the activity of OGTA001 towards the activity found in control subjects (e.g., humans free from colorectal cancer) is selected for further testing or therapeutic use.

In another embodiment, test compounds that reduce the severity of one or more symptoms associated with colorectal cancer are identified in human subjects having colorectal cancer, preferably subjects with severe colorectal cancer. In accordance with this embodiment, a test compound or a control compound is administered to the subjects, and the effect of a test compound on one or more symptoms of colorectal cancer is determined. A test compound that reduces one or more symptoms can be identified by comparing the subjects treated with a control compound to the subjects treated with the test compound. Techniques known to physicians familiar with colorectal cancer can be used to determine whether a test compound reduces one or more symptoms associated with colorectal cancer. For example, a test compound that reduces tumour burden in a subject having colorectal cancer will be beneficial for subjects having colorectal cancer.

In a preferred embodiment, a test compound that reduces the severity of one or more symptoms associated with colorectal cancer in a human having colorectal cancer is selected for further testing or therapeutic use.

Therapeutic and Prophylactic Compositions and their Use

The invention provides methods of treatment (and prophylaxis) comprising administering to a subject an effective amount of a compound of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection into colorectal tissue or at the site (or former site) of a malignant tumor or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the colon, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of colorectal cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Determining Abundance of OGTA001 by Imaging Technology

An advantage of determining abundance of OGTA001 by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of OGTA001 using such techniques requires incorporation or binding of a suitable label e.g. a radiotracer such as $^{18}F$, $^{11}C$ or $^{123}I$ (see e.g. NeuroRx—The Journal of the American Society for Experimental NeuroTherapeutics (2005) 2(2), 348-360 and idem pages 361-371 for further details of the techniques). Radiotracers or other labels may be incorporated into OGTA001 by administration to the subject (e.g. by injection) of a suitably labelled specific ligand. Alternatively they may be incorporated into a binding affinity reagent (antibody, Affibody, Nanobody, Unibody etc.) specific for OGTA001 which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding affibody molecule, Cancer Res. 2006 Apr. 15; 66(8):4339-48).

Diagnosis and Treatment of Colorectal Cancer Using Immunohistochemistry

Immunohistochemistry is an excellent detection technique and may therefore be very useful in the diagnosis and treatment of colorectal cancer. Immunohistochemistry may be used to detect, diagnose, or monitor colorectal cancer through the localization of OGTA001 antigens in tissue sections by the use of labeled antibodies (or other affinity reagents such as Affibodies, Nanobodies or Unibodies), derivatives and analogs thereof, which specifically bind to OGTA001, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutical approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

Preferred features of each aspect of the invention are as for each of the other aspects mutatis mutandis. The prior art documents mentioned herein are incorporated to the fullest extent permitted by law.

EXAMPLE 1

Identification of Membrane Proteins Expressed in Colorectal Cancer Blood and Tissue Samples Using 1D Gel Electrophoresis Using the following Reference Protocol, membrane proteins extracted from colorectal cancer tissue samples were separated by 1D gel and analysed.

1.1 Materials and Methods
1.1.1—Plasma Membrane Fractionation

The cells recovered from the epithelium of a colorectal adenocarcinoma were lysed and submitted to centrifugation at 1000G. The supernatant was taken, and it was subsequently centrifuged at 3000G. Once again, the supernatant was taken, and it was then centrifuged at 100 000G.

The resulting pellet was recovered and put on 15-60% sucrose gradient.

A Western blot was used to identify sub cellular markers, and the Plasma Membrane fractions were pooled.

The pooled solution was either run directly on 1D gels (see section 1.1.4 below), or further fractionated into heparin binding and nucleotide binding fractions as described below.

1.1.2—Plasma Membrane Heparin-Binding Fraction

The pooled solution from 1.1.1 above was applied to a Heparin column, eluted from column and run on 1D gels (see section 1.1.4 below).

1.1.3—Plasma Nucleotide-Binding Fraction

The pooled solution from 1.1.1 above was applied to a Cibacrom Blue 3GA column, eluted from column and run on 1D gels (see section 1.1.4 below).

1.1.4—1D Gel Technology

Protein or membrane pellets were solubilised in 1D sample buffer (1-2 μg/μl). The sample buffer and protein mixture was then heated to 95° C. for 3 min.

A 9-16% acrylamide gradient gel was cast with a stacking gel and a stacking comb according to the procedure described in Ausubel F. M. et al., eds., 1989, Current Protocols in Molecular Biology, Vol. II, Green Publishing Associates, Inc., and John Wiley & Sons, Inc., New York, section 10.2, incorporated herein by reference in its entirety.

30-50 micrograms of the protein mixtures obtained from detergent and the molecular weight standards (66, 45, 31, 21, 14 kDa) were added to the stacking gel wells using a 10 microlitre pipette tip and the samples run at 40 mA for 5 hours.

The plates were then prised open, the gel placed in a tray of fixer (10% acetic acid, 40% ethanol, 50% water) and shaken overnight. Following this, the gel was primed by 30 minutes shaking in a primer solution (7.5% acetic acid (75 ml), 0.05% SDS (5 ml of 10%)). The gel was then incubated with a fluorescent dye (7.5% acetic acid, 0.06% OGS in-house dye (600 µl)) with shaking for 3 hrs. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety.

A computer-readable output was produced by imaging the fluorescently stained gels with an Apollo 3 scanner (Oxford Glycosciences, Oxford, UK). This scanner is developed from the scanner described in WO 96/36882 and in the Ph.D. thesis of David A. Basiji, entitled "Development of a High-throughput Fluorescence Scanner Employing Internal Reflection Optics and Phase-sensitive Detection (Total Internal Reflection, Electrophoresis)", University of Washington (1997), Volume 58/12-B of Dissertation Abstracts International, page 6686, the contents of each of which are incorporated herein by reference. The latest embodiment of this instrument includes the following improvements: The gel is transported through the scanner on a precision lead-screw drive system. This is preferable to laying the glass plate on the belt-driven system that is defined in the Basiji thesis as it provides a reproducible means of accurately transporting the gel past the imaging optics.

The gel is secured into the scanner against three alignment stops that rigidly hold the glass plate in a known position. By doing this in conjunction with the above precision transport system and the fact that the gel is bound to the glass plate, the absolute position of the gel can be predicted and recorded. This ensures that accurate co-ordinates of each feature on the gel can be communicated to the cutting robot for excision. This cutting robot has an identical mounting arrangement for the glass plate to preserve the positional accuracy.

The carrier that holds the gel in place has integral fluorescent markers (Designated M1, M2, M3) that are used to correct the image geometry and are a quality control feature to confirm that the scanning has been performed correctly.

The optical components of the system have been inverted. The laser, mirror, waveguide and other optical components are now above the glass plate being scanned. The embodiment of the Basiji thesis has these underneath. The glass plate is therefore mounted onto the scanner gel side down, so that the optical path remains through the glass plate. By doing this, any particles of gel that may break away from the glass plate will fall onto the base of the instrument rather than into the optics.

In scanning the gels, they were removed from the stain, rinsed with water and allowed to air dry briefly and imaged on the Apollo 3. After imaging, the gels were sealed in polyethylene bags containing a small volume of staining solution, and then stored at 4° C.

Apparent molecular weights were calculated by interpolation from a set of known molecular weight markers run alongside the samples.

1.1.5—Recovery and Analysis of Selected Proteins

Proteins were robotically excised from the gels by the process described in U.S. Pat. No. 6,064,754, Sections 5.4 and 5.6, 5.7, 5.8 (incorporated herein by reference), as is applicable to 1D-electrophoresis, with modification to the robotic cutter as follows: the cutter begins at the top of the lane, and cuts a gel disc 1.7 mm in diameter from the left edge of the lane. The cutter then moves 2 mm to the right, and 0.7 mm down and cuts a further disc. This is then repeated. The cutter then moves back to a position directly underneath the first gel cut, but offset by 2.2 mm downwards, and the pattern of three diagonal cuts are repeated. This is continued for the whole length of the gel.

NOTE: If the lane is observed to broaden significantly then a correction can be made also sideways i.e. instead of returning to a position directly underneath a previous gel cut, the cut can be offset slightly to the left (on the left of the lane) and/or the right (on the right of the lane). The proteins contained within the gel fragments were processed to generate tryptic peptides; partial amino acid sequences of these peptides were determined by mass spectroscopy as described in WO98/53323 and application Ser. No. 09/094,996, filed Jun. 15, 1998.

Proteins were processed to generate tryptic digest peptides. Tryptic peptides were analyzed by mass spectrometry using a PerSeptive Biosystems Voyager-DETM STR Matrix-Assisted Laser Desorption Ionization Time-of-Flight (MALDI-TOF) mass spectrometer, and selected tryptic peptides were analyzed by tandem mass spectrometry (MS/MS) using a Micromass Quadrupole Time-of-Flight (Q-TOF) mass spectrometer (Micromass, Altrincham, U.K.) equipped with a Nanoflow™ electrospray Z-spray source. For partial amino acid sequencing and identification of OGTA001, uninterpreted tandem mass spectra of tryptic peptides were searched using the SEQUEST search program (Eng et al., 1994, J. Am. Soc. Mass Spectrom. 5:976-989), version v.C.1. Criteria for database identification included: the cleavage specificity of trypsin; the detection of a suite of a, b and y ions in peptides returned from the database, and a mass increment for all Cys residues to account for carbamidomethylation. The database searched was a database constructed of protein entries in the non-redundant database held by the National Centre for Biotechnology Information (NCBI) which is accessible at www.ncbi.nlm.nih.gov. Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art. (In the case of interpretation of low-energy fragmentation mass spectra of peptide ions see Gaskell et al., 1992, Rapid Commun. Mass Spectrom. 6:658-662).

1.1.6—Discrimination of Colorectal Cancer Associated Proteins

The process to identify OGTA001 uses the peptide sequences obtained experimentally by mass spectrometry described above of naturally occurring human proteins to identify and organize coding exons in the published human genome sequence.

Recent dramatic advances in defining the chemical sequence of the human genome have led to the near completion of this immense task (Venter, J. C. et al. (2001). The sequence of the human genome. Science 16: 1304-51; International Human Genome Sequencing Consortium. (2001).

Initial sequencing and analysis of the human genome Nature 409: 860-921). There is little doubt that this sequence information will have a substantial impact on our understanding of many biological processes, including molecular evolution, comparative genomics, pathogenic mechanisms and molecular medicine. For the full medical value inherent in the sequence of the human genome to be realised, the genome needs to be 'organised' and annotated. By this, is meant at least the following three things: (i) The assembly of the sequences of the individual portions of the genome into a coherent, continuous sequence for each chromosome. (ii) The unambiguous identification of those regions of each chromosome that contain genes. (iii) Determination of the fine structure of the genes and the properties of its mRNA and protein products. While the definition of a 'gene' is an increasingly complex issue (H Pearson: What is a gene? Nature (2006) 24: 399-401), what is of immediate interest for drug discovery and development is a catalogue of those genes that encode functional, expressed proteins. A subset of these genes will be involved in the molecular basis of most if not all pathologies. Therefore an important and immediate goal for the pharmaceutical industry is to identify all such genes in the human genome and describe their fine structure.

Processing and Integration of Peptide Masses, Peptide Signatures, ESTs and Public Domain Genomic Sequence Data to form OGAP® Database Discrete genetic units (exons, transcripts and genes) were identified using the following sequential steps:

1. A 'virtual transcriptome' is generated, containing the tryptic peptides which map to the human genome by combining the gene identifications available from Ensembl and various gene prediction programs. This also incorporates SNP data (from dbSNP) and all alternate splicing of gene identifications. Known contaminants were also added to the virtual transcriptome.
2. All tandem spectra in the OGeS Mass Spectrometry Database are interpreted in order to produce a peptide that can be mapped to one in the virtual transcriptome. A set of automated spectral interpretation algorithms were used to produce the peptide identifications.
3. The set of all mass-matched peptides in the OGeS Mass Spectrometry Database is generated by searching all peptides from transcripts hit by the tandem peptides using a tolerance based on the mass accuracy of the mass spectrometer, typically 20 ppm.
4. All tandem and mass-matched peptides are combined in the form of "protein clusters". This is done using a recursive process which groups sequences into clusters based on common peptide hits. Biological sequences are considered to belong to the same cluster if they share one or more tandem or mass-matched peptide.
5. After initial filtering to screen out incorrectly identified peptides, the resulting clusters are then mapped on the human genome.
6. The protein clusters are then aggregated into regions that define preliminary gene boundaries using their proximity and the co-observation of peptides within protein clusters. Proximity is defined as the peptide being within 80,000 nucleotides on the same strand of the same chromosome. Various elimination rules, based on cluster observation scoring and multiple mapping to the genome are used to refine the output. The resulting 'confirmed genes' are those which best account for the peptides and masses observed by mass spectrometry in each cluster. Nominal co-ordinates for the gene are also an output of this stage.
7. The best set of transcripts for each confirmed gene are created from the protein clusters, peptides, ESTs, candidate exons and molecular weight of the original protein spot.
8. Each identified transcript was linked to the sample providing the observed peptides.
9. Use of an application for viewing and mining the data. The result of steps 1-8 was a database containing genes, each of which consisted of a number of exons and one or more transcripts. An application was written to display and search this integrated genome/proteome data. Any features (OMIM disease locus, InterPro etc.) that had been mapped to the same Golden Path co-ordinate system by Ensembl could be cross-referenced to these genes by coincidence of location and fine structure.

Results

The process was used to generate approximately 1 million peptide sequences to identify protein-coding genes and their exons resulted in the identification of protein sequences for 18083 genes across 67 different tissues and 57 diseases including 506 genes in Bladder cancer, 4,713 genes in Breast cancer, 766 genes in Burkitt's lymphoma, 1,371 genes in Cervical cancer, 949 genes in Colorectal cancer, 1,782 genes in Hepatocellular carcinoma, 2,424 genes in CLL, 978 genes in Lung cancer, 1,764 genes in Melanoma, 1,033 genes in Ovarian Cancer, 2,961 genes in Pancreatic cancer and 3,307 genes in Prostate cancer, illustrated here by OGTA001 isolated and identified from colorectal cancer samples. Following comparison of the experimentally determined sequences with sequences in the OGAP® database, OGTA001 showed a high degree of specificity to colorectal cancer indicative of the prognostic and diagnostic nature.

1.2 Results

These experiments identified OGTA001, as further described herein. The full-length OGTA001 was detected in the plasma membrane of colorectal cancer samples and was not detected in the cytosol.

FIG. 3 shows the Protein Index for OGTA001. For each gene, the protein index uses the mass spectrometry data to assign a score to each disease, relative to the global database. The Protein Index can then be used to identify cancer specific genes with a high score in cancer indications and low/negligible scores in normal and other diseases. The index contains ~1 million peptides sequenced via mass spectrometry from 56 diseases. For each gene, this yields a score for each disease and subcellular location. The results are summarized below:

| Protein Index Report for OGTA001 |
| --- |
| Indications positive: |
| Colorectal cancer |
| Disease controls |
| Acute monocytic leukaemia |
| Acute T-cell leukaemia |
| Alzheimer's Disease |
| Arthritis |
| Asthma |
| Atherosclerosis |
| B-cell non-Hodgkin's lymphoma |
| Bladder carcinoma |
| Breast cancer |
| Breast diseases, benign |
| Burkitt's lymphoma |
| Bursitis |
| Cancer, unspecified |

Protein Index Report for OGTA001

Cervical cancer
Chronic lymphocytic leukaemia
Chronic obstructive pulmonary disease
Colorectal cancer
Dementia, vascular
Depression
Diabetes and Obesity
Diverticulitis
Dyslipidaemia
Emphysema
Focal apocrine metaplasia
Gastric cancer
Gaucher disease
Glioblastoma
Hepatoblastoma
Hepatocellular carcinoma
Hypertension
Lactational foci
Leukaemia, unspecified
Liver cirrhosis
Lung cancer
Lymphoma, histiocytic
Melanoma
Metabolic syndrome X
Migraine, acute
Multiple sclerosis
Neuroblastoma
Normal
Obesity
Osteoarthritis
Osteosarcoma
Ovarian cancer
Pancreatic cancer
Prostate cancer
Prostatic diseases, benign
Prostatitis
Renal cell cancer
Retinoblastoma
Schizophrenia
Skin ulcer
Smoker
Teratocarcinoma Subcellular Location Birbeck Granules
Cell surface digest
Chromatin Fraction
Crude Cell Membrane
Cytosol
Golgi/Mitochondrial Membrane
Membrane Glycoprotein Binding Fraction
Mitochondria
Nucleus
Peroxisomes
Plasma Membrane
Secreted
Soluble Fraction
Supernatant
Whole Cell FIG. 3 shows the Protein Index for OGTA001 is very high in colorectal cancer plasma membrane and very low in normal plasma membrane. OGTA001 was not detected in any other diseases. This indicates that OGTA001 is potentially a good marker for colorectal cancer.

EXAMPLE 2

Identification of Membrane Proteins Expressed in Colorectal Cancer Blood and Tissue Samples Using Isotope Tagging for Absolute and Relative Quantitation (Itraq)

Using the following Reference Protocol, membrane proteins extracted from colorectal cancer tissue and normal adjacent colorectal tissue samples were digested, labelled with Isotope Tagging for Absolute & Relative Quantitation reagents (iTRAQ; Applied Biosystems, Foster City, Calif., USA) and resulting peptides sequenced by tandem mass spectrometry.

2.1 Materials and Methods 2.1.1—Plasma Membrane Fractionation

The cells recovered from a colorectal cancer or normal adjacent tissue were lysed and submitted to centrifugation at 1000G. The supernatant was taken, and it was subsequently centrifuged at 3000G. Once again, the supernatant was taken, and it was then centrifuged at 100 000G.

The resulting pellet was recovered and put on 15-60% sucrose gradient.

A Western blot was used to identify sub cellular markers, and the Plasma Membrane fractions were pooled.

The pooled solution was then analysed directly by iTRAQ (see section 2.1.2 below).

2.1.2—iTRAQ Methodology

Membrane protein pellets from colorectal cancer and normal adjacent tissue were solubilised in sample buffer (2-4 µg/µl in 0.5% SDS) by the addition of buffer and then heating to 95° C. for 3 min.

To a volume of each protein solution equating to 50 µg, 150 µl of 0.5M triethylammonium bicarbonate (TEAB) solution was added. To each sample, 3 µl of 50 mM tris-(2-carboxyethyl)phosphine was added and the mixture was incubated at 60° C. for 1 hour. 1 µl of cysteine blocking reagent, 200 mM methyl methanethiosulphonate (MMTS) in isopropanol, was then added. After incubation at room temperature for 10 minutes, 15 µl of 1 µg/µl trypsin was added to each sample followed by incubation at 37° C. overnight.

The digested samples were dried under a vacuum and re-constituted with 30 µl of 0.5M TEAB solution. 70 µl ethanol was added to each of the four iTRAQ reagents (114/115/116/117) and one reagent added to each of the four samples analysed (two colorectal cancer samples and two corresponding normal adjacent tissue samples) and left at room temperature for 1 hour. The specific reagent added to each sample was recorded. The four labeled samples were combined & vortexed.

The combined sample was reduced to dryness under a vacuum and de-salted by loading onto a C18 spin column, washing with aqueous solvent and then eluting with 70% acetonitrile. The sample fraction was again reduced to dryness and then re-dissolved in 40 µl of solvent A (97.9 water, 2% acetonitrile, 0.1% formic acid) prior to ion exchange fractionation.

2.1.3—Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 µm; 50×0.8 mm) using a 20 µl/min gradient of 0-100 mM sodium acetate over 20 minutes and then to 1M over 10 minutes. 1 minute fractions were collected over the 30 minute run.

Each fraction was analysed by liquid chromatography/mass spectrometry using an Agilent 1200 chromatograph fitted with a Zorbax 300SB-C18 (150 mm×75 μm) and an Agilent 6510 quadrupole-time-of-flight instrument (Agilent, Santa Clara, Calif., USA). Peptides were eluted with a 300 nl/min gradient increasing from 15% to 45% acetonitrile in 60 minutes. Data was acquired in auto MS/MS mode such that up to 3 precursor ions above the intensity threshold were selected and product ion spectra accumulated to facilitate the sequencing of the labeled peptides. Raw was processed to create peak lists using Spectrum Mill software (Agilent, Santa Clara, Calif., USA).

2.1.4—Amino Acid Sequence Analysis of Labeled Peptides

For partial amino acid sequencing and identification of OGTA001, uninterpreted tandem mass spectra of tryptic peptides were searched using the SEQUEST search program (Eng et al., 1994, J. Am. Soc. Mass Spectrom. 5:976-989). Criteria for database identification included: the cleavage specificity of trypsin; the detection of a suite of a, b and y ions in peptides returned from the database, and a mass increment for all cysteine residues to account for modification with methyl methanethiosulphonate and the addition of iTRAQ labels to free amines (N-terminus & lysine). The data was searched through IPI Human v3.23 (www.ebi.ac.uk/IPI/IPI-human.html).

2.1.5—Discrimination of Colorectal Cancer Associated Proteins

The process described in Example 1 section 1.1.6 was employed to discriminate the colorectal cancer associated proteins in the experimental samples.

2.2 Results

These experiments identified OGTA001, as further described herein. The full-length OGTA001 was detected in the plasma membrane of colorectal cancer samples. The iTRAQ analysis showed that levels of OGTA001 in the colorectal cancer samples were higher than in the matched normal adjacent tissue samples.

FIG. 2 shows the Protein Index for OGTA001. See Example 1 section 1.2 for a description of the Protein Index for OGTA001.

EXAMPLE 3

Multiplex Assay to Detect Soluble OGTA001 in Patient Serum Using Luminex Technology Using the following Reference Protocol, multiplex assays using the Luminex technology were performed using antibodies to soluble OGTA001.

3.1 Materials and Methods

Antibodies to OGTA001 (as defined by SEQ ID No: 1) were developed at Biosite. Each primary antibody to soluble OGTA001 (as defined by SEQ ID No: 1) was conjugated to a unique Luminex magnetic microsphere (Mug beads, Luminex Corporation, Austin, Tex.). Mag bead cocktail (50 ul) was added to a 96 black well round bottom Costar plate (Corning Incorporated, Corning N.Y.). Using a 96 well magnetic ring stand, the Mag beads were pulled down for 1 minute and washed with wash/assay buffer (PBS with 1% BSA and 0.02% Tween 20). 50 ul of sample or standard was added along with an additional 50 ul of wash/assay buffer and allowed to incubate on a shaker for 1 hour at room temperature. Plate was placed on magnetic ring stand and allowed to sit for 1 minute. Mag beads were then washed again. Biotin labeled antibody was then added at 50 ul per well with an additional 50 ul of wash/assay buffer and allowed to incubate on a shaker for 1 hour at room temperature. The plate again was placed on a magnetic stand and the Mag beads were washed. Streptavidin-RPE (Prozyme, San Leandro, Calif., Phycolin, Code#PJ31S) was diluted to 1 ug/ml in wash/assay buffer and 50 ul was added to each well along with an additional 50 ul of wash/assay buffer and allowed to incubate on a shaker for 1 hour at room temperature. Final wash was performed and the beads were re-suspended with 100 ul of wash/assay buffer and each well was then read in a Luminex 200 reader using Xponent software 3.0. All reagent dilutions were made in wash/assay buffer. Biotin-antibody varied for each assay to optimal concentration. Initial Mag bead amounts added were approximately 50,000 for each assay. Magnetic beads were allowed 1 minute pull down time prior to each wash. Each wash step was 3 times washed with 100 ul of wash/assay buffer. Assay standard curves were made in a normal donor patient serum pool. Luminex reader and Mag beads were used and prepared according to manufacturer guidelines. Standard curves were calculated using a 5 parameter log-logistic fit and each sample concentration was determined from this curve fit.

Final Box and ROC results were analyzed using Analyse-it General+Clinical Laboratory 1.73 (Analyse-it Software Ltd., Leeds England).

3.2 Results

Experiments using 61 normal samples and 65 colorectal cancer resulted in further evidence that soluble OGTA001 can be detected in colorectal cancer patient serum samples and also that the concentration of soluble OGTA001 is higher in colorectal cancer patient serum than in normal serum samples. These results demonstrate that soluble OGTA001 may be used as a serum diagnostic for colorectal cancer.

Figure 4:
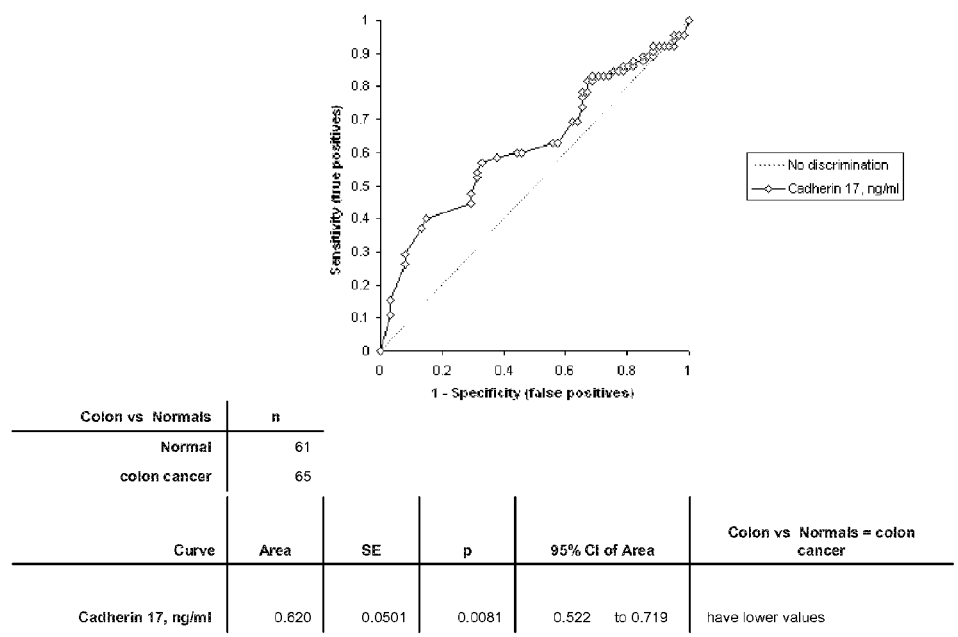
FIG. 4 shows ROC curve data for the presence of the protein of the invention in colorectal cancer patient serum samples.
Figure 5:
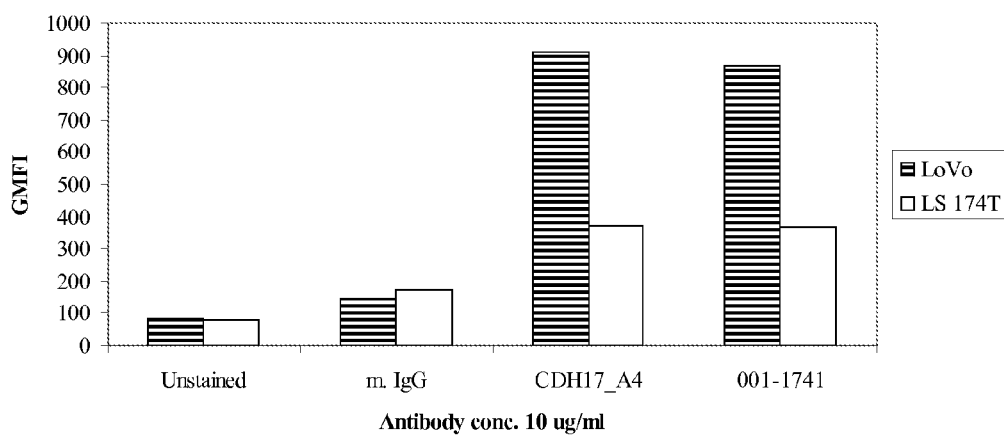
FIG. 5 shows results of FACS analysis on CDH17_A4 in LoVo and LS174T cells.
Figure 6A:
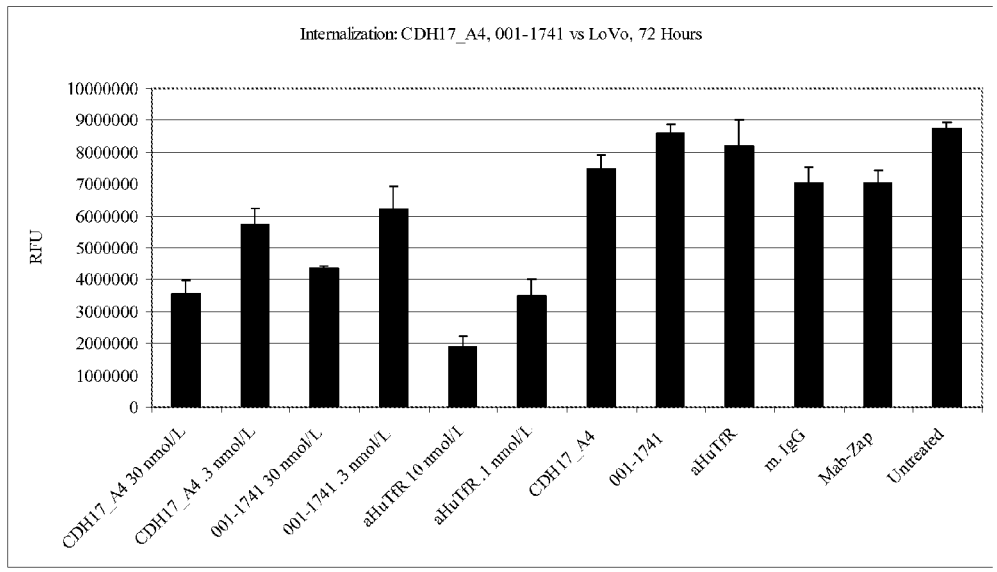
FIG. 6A shows results of internalisation of CDH17_A4 by MabZAP assay in LoVo colon cancer cells.
Figure 6B:
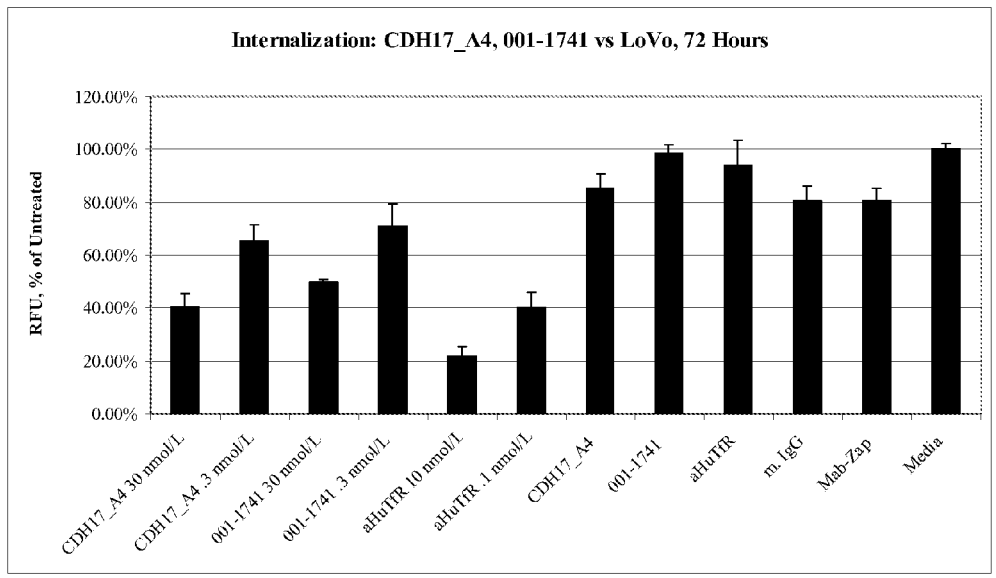
FIG. 6B shows results of internalisation of CDH17_A4 by MabZAP assay in LoVo colon cancer cells.
Figure 6C:
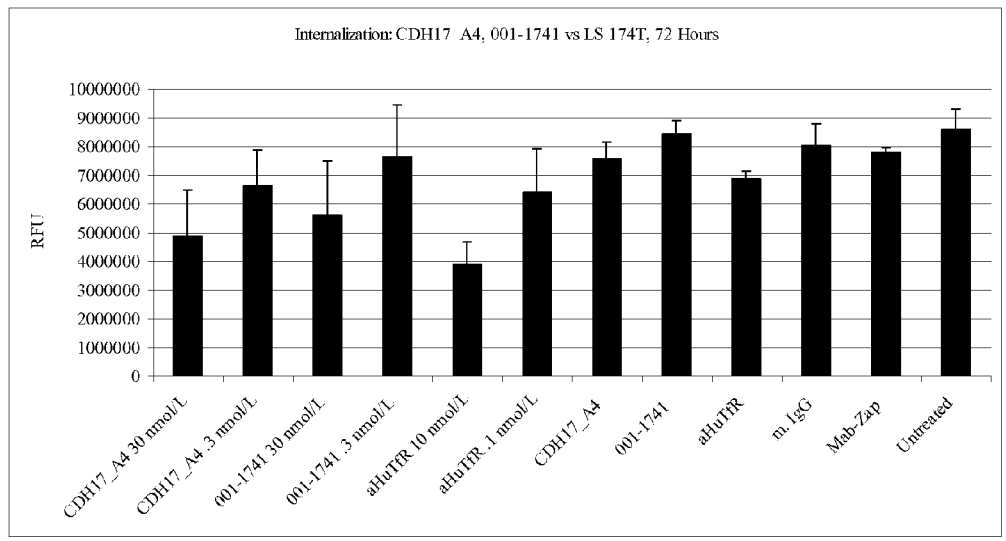
FIG. 6C shows results of internalisation of CDH17_A4 by MabZAP assay in LS174T colon cancer cells.
Figure 6D:
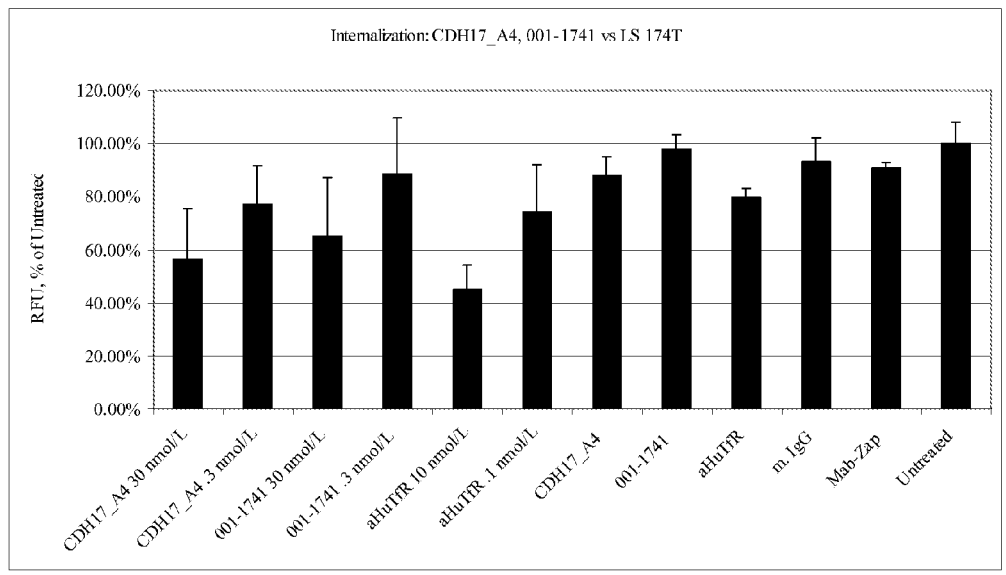
FIG. 6D shows results of internalisation of CDH17_A4 by MabZAP assay in LS174T colon cancer cells.
Figure 7A:
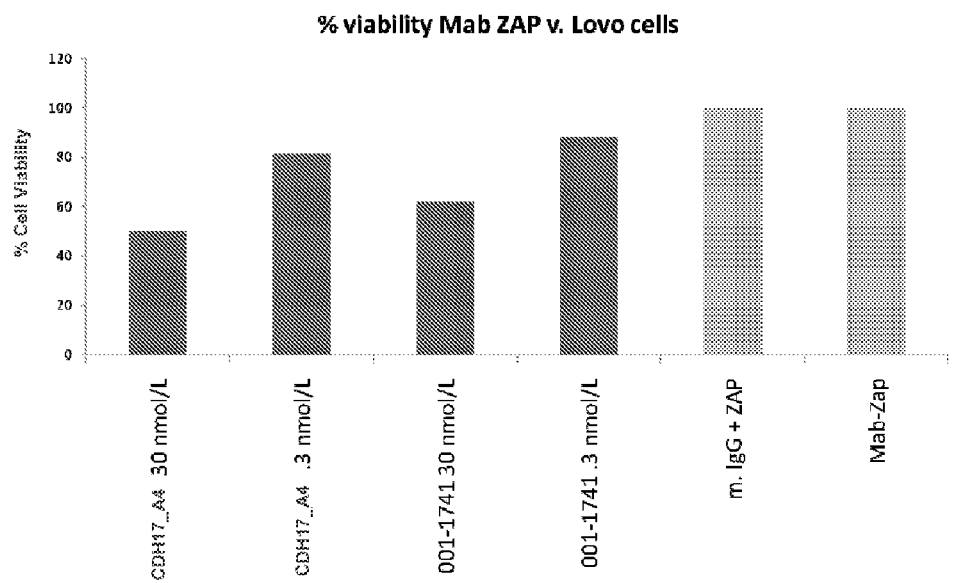
FIG. 7A shows results of internalisation of CDH17_A4 by MabZAP assay in LoVo colon cancer cells.
Figure 7B:
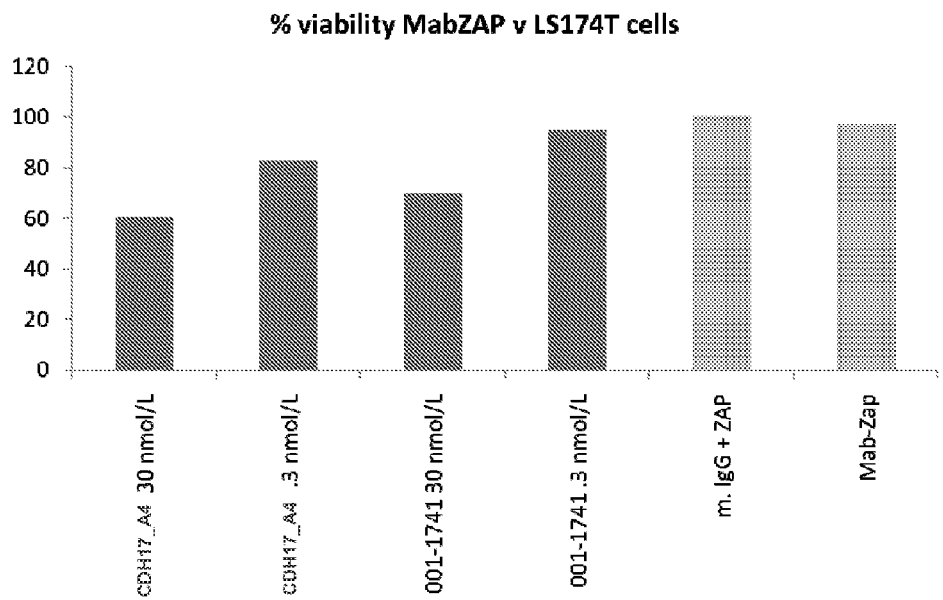
FIG. 7B shows results of internalisation of CDH17_A4 by MabZAP assay in LS174T colon cancer cells.

FIG. 3 shows ROC curve data for soluble OGTA001 in colorectal cancer patient serum samples. The ROC curves plot sensitivity (true positives) against 1-specificity (false positives). An area under the ROC curve of greater than 0.5 indicates good discrimination between disease and normal. This is the case in the data shown in FIG. 4, which, along with the low p values, indicate that the concentration of soluble OGTA001 is significantly higher in colorectal cancer patient serum samples than in normal serum samples.

The following examples and the antibodies prepared and used therein are based in part, upon disclosure found in co-pending parent International Application No. PCT/US2010/031739, having an international filing date of Apr. 20, 2010, and the disclosure of this application is accordingly incorporated herein by reference in its entirety.

EXAMPLE 4

Construction of a Phage-Display Library

A recombinant protein composed of the extracellular domain of the CDH17 (SEQ ID NO:1) was eurkaryotically synthesized by standard recombinant methods and used as antigen for immunization.

Immunization and mRNA Isolation

A phage display library for identification of the CDH17-binding molecules was constructed as follows. A/J mice (Jackson Laboratories, Bar Harbor, Me.) were immunized intraperitoneally with the recombinant CDH17 antigen (the extracellular domain), using 100 μg protein in Freund's complete adjuvant, on day 0, and with 100 μg antigen on day 28. Test bleeds of mice were obtained through puncture of the retro-orbital sinus. If, by testing the titers, they were deemed high by ELISA using the biotinylated CDH17 antigen immobilized via neutravidin (Reacti-Bind™) NeutrAvidin™-Coated Polystyrene Plates, Pierce, Rockford, Ill.), the mice were boosted with 100 μg of protein on day 70, 71 and 72, with subsequent sacrifice and splenectomy on day 77. If titers of antibody were not deemed satisfactory, mice were boosted with 100 μg antigen on day 56 and a test bleed taken on day 63. If satisfactory titers were obtained, the animals were boosted with 100 μg of antigen on day 98, 99, and 100 and the spleens harvested on day 105.

The spleens were harvested in a laminar flow hood and transferred to a petri dish, trimming off and discarding fat and connective tissue. The spleens were macerated quickly with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate pH 7.0, 2.64 ml 10% sarkosyl (Fisher Scientific, Pittsburgh, Pa.), 0.36 ml 2-mercaptoethanol (Fisher Scientific, Pittsburgh, Pa.). This spleen suspension was pulled through an 18 gauge needle until all cells were lysed and the viscous solution was transferred to a microcentrifuge tube. The petri dish was washed with 100 μl of solution D to recover any remaining spleen. This suspension was then pulled through a 22 gauge needle an additional 5-10 times.

The sample was divided evenly between two microcentrifuge tubes and the following added, in order, with mixing by inversion after each addition: 50 μl 2 M sodium acetate pH 4.0, 0.5 ml water-saturated phenol (Fisher Scientific, Pittsburgh, Pa.), 100 μl chloroform/isoamyl alcohol 49:1 (Fisher Scientific, Pittsburgh, Pa.). The solution was vortexed for 10 sec and incubated on ice for 15 min. Following centrifugation at 14 krpm for 20 min at 2-8° C., the aqueous phase was transferred to a fresh tube. An equal volume of water saturated phenol:chloroform:isoamyl alcohol (50:49:1) was added, and the tube vortexed for ten seconds. After 15 min incubation on ice, the sample was centrifuged for 20 min at 2-8° C., and the aqueous phase transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed from the RNA pellet.

The RNA pellets were each dissolved in 300 μl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 μl of ice-cold 70% ethanol. The sample was again centrifuged 14 krpm for 20 min at 4° C., the 70% ethanol solution aspirated, and the RNA pellet dried in vacuo. The pellet was resuspended in 100 μl of sterile diethyl pyrocarbonate-treated water. The concentration was determined by A260 using an absorbance of 1.0 for a concentration of 40 μg/ml. The RNAs were stored at −80° C.

Preparation of Complementary DNA (cDNA)

The total RNA purified from mouse spleens as described above was used directly as template for cDNA preparation. RNA (50 μg) was diluted to 100 μL with sterile water, and 10 μL of 130 ng/μL oligo dT12 (synthesized on Applied Biosystems Model 392 DNA synthesizer) was added. The sample was heated for 10 min at 70° C., then cooled on ice. Forty μL 5* first strand buffer was added (Gibco/BRL, Gaithersburg, Md.), along with 20 μL 0.1 M dithiothreitol (Gibco/BRL, Gaithersburg, Md.), 10 μL 20 mM deoxynucleoside triphosphates (dNTP's, Boehringer Mannheim, Indianapolis, Ind.), and 10 μL water on ice. The sample was then incubated at 37° C. for 2 min. Ten μL reverse transcriptase (Superscript™) II, Gibco/BRL, Gaithersburg, Md.) was added and incubation was continued at 37° C. for 1 hr. The cDNA products were used directly for polymerase chain reaction (PCR).

Amplification of Antibody Genes by PCR

To amplify substantially all of the H and L chain genes using PCR, primers were chosen that corresponded to substantially all published sequences. Because the nucleotide sequences of the amino termini of H and L contain considerable diversity, 33 oligonucleotides were synthesized to serve as 5' primers for the H chains, and 29 oligonucleotides were synthesized to serve as 5' primers for the kappa L chains as described in U.S. Pat. No. 6,555,310. The constant region nucleotide sequences for each chain required only one 3' primer for the H chains and one 3' primer for the kappa L chains.

A 50 μL reaction was performed for each primer pair with 50 μmol of 5' primer, 50 μmol of 3' primer, 0.25 μL Taq DNA Polymerase (5 units/μL, Boehringer Mannheim, Indianapolis, Ind.), 3 μL cDNA (prepared as described), 5 μL 2 mM dNTP's, 5 μL 10*Taq DNA polymerase buffer with MgCl2 (Boehringer Mannheim, Indianapolis, Ind.), and $H_2O$ to 50 μL. Amplification was done using a GeneAmp® 9600 thermal cycler (Perkin Elmer, Foster City, Calif.) with the following thermocycle program: 94° C. for 1 min; 30 cycles of 94° C. for 20 sec, 55° C. for 30 sec, and 72° C. for 30 sec, 72° C. for 6 min; 4° C.

The dsDNA products of the PCR process were then subjected to asymmetric PCR using only a 3' primer to generate substantially only the anti-sense strand of the target genes. A 100 μL reaction was done for each dsDNA product with 200 μmol of 3' primer, 2 μL of ds-DNA product, 0.5 μL Taq DNA Polymerase, 10 μL 2 mM dNTP's, 10 μL 10*Taq DNA polymerase buffer with $MgCl_2$ (Boehringer Mannheim, Indianapolis, Ind.), and $H_2O$ to 100 μL. The same PCR program as that described above was used to amplify the single-stranded (ss)-DNA.

1. Purification of Single-Stranded DNA by High Performance Liquid Chromatography and Kinasing Single-Stranded DNA The H chain ss-PCR products and the L chain single-stranded PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2-8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 μL water and the L chain products were pooled separately in 210 μL water. The single-stranded DNA was purified by high performance liquid chromatography (HPLC) using a Hewlett Packard 1090 HPLC and a Gen-Pak™) FAX anion exchange column (Millipore Corp., Milford, Mass.). The gradient used to purify the single-stranded DNA is shown in Table 3, and the oven temperature was 60° C. Absorbance was monitored at 260 nm. The single-stranded DNA eluted from the HPLC was collected in 0.5 min fractions. Fractions containing single-stranded DNA were ethanol precipitated, pelleted and dried as described above. The dried DNA pellets were pooled in 200 μL sterile water.

TABLE 3

HPLC gradient for purification of ss-DNA

| Time (min) | % A | % B | % C | Flow (ml/min) |
| --- | --- | --- | --- | --- |
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |

TABLE 3-continued

HPLC gradient for purification of ss-DNA

| Time (min) | % A | % B | % C | Flow (ml/min) |
|---|---|---|---|---|
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The single-stranded DNA was 5'-phosphorylated in preparation for mutagenesis. Twenty-four μL 10* kinase buffer (United States Biochemical, Cleveland, Ohio), 10.4 μL 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of Tris equilibrated phenol (pH>8.0, United States Biochemical, Cleveland, Ohio):chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 μL sterile water. The concentration was determined by measuring the absorbance of an aliquot of the DNA at 260 nm using 33 μg/ml for an absorbance of 1.0. Samples were stored at −20° C.

2. Preparation of Uracil Templates Used in Generation of Spleen Antibody Phage Libraries One ml of *E. coli* CJ236 (BioRAD, Hercules, Calif.) overnight culture was added to 50 ml 2*YT in a 250 ml baffled shake flask. The culture was grown at 37° C. to OD600=0.6, inoculated with 10 μl of a 1/100 dilution of BS45 vector phage stock (described in U.S. Pat. No. 6,555,310) and growth continued for 6 hr. Approximately 40 ml of the culture was centrifuged at 12 krpm for 15 min at 4° C. The supernatant (30 ml) was transferred to a fresh centrifuge tube and incubated at room temperature for 15 min after the addition of 15 μl of 10 mg/ml RNaseA (Boehringer Mannheim, Indianapolis, Ind.). The phages were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2-8° C. The supernatant was carefully discarded, and the tube briefly spun to remove all traces of supernatant. The pellet was resuspended in 400 μl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 μl sterile water and the concentration determined by A260 using an absorbance of 1.0 for a concentration of 40 μg/ml. The template was diluted to 250 ng/μL with sterile water, aliquoted and stored at −20° C.

Mutagenesis of Uracil Template with ss-DNA and Electroporation into *E. coli* to Generate Antibody Phage Libraries Antibody phage display libraries were generated by simultaneously introducing single-stranded heavy and light chain genes onto a phage display vector uracil template. A typical mutagenesis was performed on a 2 μg scale by mixing the following in a 0.2 ml PCR reaction tube: 8 μl of (250 ng/μL) uracil template, 8 μL of 10* annealing buffer (200 mM Tris pH 7.0, 20 mM $MgCl_2$, 500 mM NaCl), 3.33 μl of kinased single-stranded heavy chain insert (100 ng/μL), 3.1 μl of kinased single-stranded light chain insert (100 ng/μL), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10* synthesis buffer (5 mM each dNTP, 10 mM ATP, 100 mM Tris pH 7.4, 50 mM MgCl2, 20 mM DTT), 8 μL T4 DNA ligase (1 U/μL, Boehringer Mannheim, Indianapolis, Ind.), 8 μL diluted T7 DNA polymerase (1 U/μL, New England BioLabs, Beverly, Mass.) and incubating at 37° C. for 30 min. The reaction was stopped with 300 μL of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μL of sterile water.

One μL of mutagenesis DNA (500 ng) was transferred into 40 μl electrocompetent *E. coli* DH12S (Gibco/BRL, Gaithersburg, Md.) using electroporation. The transformed cells were mixed with approximately 1.0 ml of overnight XL-1 cells which were diluted with 2*YT broth to 60% the original volume. This mixture was then transferred to a 15-ml sterile culture tube and 9 ml of top agar added for plating on a 150-mm LB agar plate. Plates were incubated for 4 hr at 37° C. and then transferred to 20° C. overnight. First round antibody phage were made by eluting phage off these plates in 10 ml of 2*YT, spinning out debris, and taking the supernatant. These samples are the antibody phage display libraries used for selecting antibodies against the CDH17. Efficiency of the electroporations was measured by plating 10 μl of a $10^{-4}$ dilution of suspended cells on LB agar plates, follow by overnight incubation of plates at 37° C. The efficiency was calculated by multiplying the number of plaques on the $10^{-4}$ dilution plate by 106. Library electroporation efficiencies are typically greater than $1*10^7$ phages under these conditions.

Transformation of *E. coli* by Electroporation

Electrocompetent *E. coli* cells were thawed on ice. DNA was mixed with 40 L of these cells by gently pipetting the cells up and down 2-3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the *E. coli* Pulser (BioRAD, Hercules, Calif.) and electroporated with the voltage set at 1.88 kV according to the manufacturer's recommendation. The transformed sample was immediately resuspended in 1 ml of 2*YT broth or 1 ml of a mixture of 400 μl 2*YT/600 μl overnight XL-1 cells and processed as procedures dictated.

Plating M13 Phage or Cells Transformed with Antibody Phage-Display Vector Mutagenesis Reaction Phage samples were added to 200 μL of an overnight culture of *E. coli* XL1-Blue when plating on 100 mm LB agar plates or to 600 μL of overnight cells when plating on 150 mm plates in sterile 15 ml culture tubes. After adding LB top agar (3 ml for 100 mm plates or 9 ml for 150 mm plates, top agar stored at 55° C. (see, Appendix A1, Sambrook et al., supra.), the mixture was evenly distributed on an LB agar plate that had been pre-warmed (37° C.-55° C.) to remove any excess moisture on the agar surface. The plates were cooled at room temperature until the top agar solidified. The plates were inverted and incubated at 37° C. as indicated.

3. Preparation of Biotinylated Cadherin-17 and Biotinylated Antibodies

The concentrated recombinant CDH17 antigen (full length extracellular domain SEQ ID No: 67) (Cadherin domains 1-2 SEQ ID No: 68) was extensively dialyzed into BBS (20 mM borate, 150 mM NaCl, 0.1% $NaN_3$, pH 8.0). After dialysis, 1 mg of the CDH17 (1 mg/ml in BBS) was reacted with a 15 fold molar excess of biotin-XX-NHS ester (Molecular Probes, Eugene, Oreg., stock solution at 40 mM in DMSO). The reaction was incubated at room temperature for 90 min and then quenched with taurine (Sigma Chemical Co., St. Louis, Mo.) at a final concentration of 20 mM. The biotinylation reaction mixture was then dialyzed against BBS at 2-8° C. After dialysis, the biotinylated CDH17 was diluted in panning buffer (40 mM Tris, 150 mM NaCl, 20 mg/ml BSA, 0.1% Tween 20, pH 7.5), aliquoted, and stored at −80° C. until needed.

Antibodies were reacted with 3-(N-maleimidylpropionyl) biocytin (Molecular Probes, Eugene, Oreg.) using a free cysteine located at the carboxy terminus of the heavy chain. Antibodies were reduced by adding DTT to a final concentration of 1 mM for 30 min at room temperature. Reduced antibody was passed through a Sephadex G50 desalting column equilibrated in 50 mM potassium phosphate, 10 mM boric acid, 150 mM NaCl, pH 7.0. 3-(N-maleimidylpropionyl)-biocytin was added to a final concentration of 1 mM and the reaction allowed to proceed at room temperature for 60 min. Samples were then dialyzed extensively against BBS and stored at 2-8° C.

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham, Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture mixed an additional 30 sec. This mixture was incubated at 45° C. for 2 hr, shaking every 30 min. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM Tris, 150 mM NaCl, 20 mg/ml BSA, 0.1% Tween 20, pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

EXAMPLE 5

Selection of Recombinant Polyclonal Antibodies to CDH17 Antigen

Binding reagents that specifically bind to the CDH17 were selected from the phage display libraries created from hyperimmunized mice as described in Example 4.

Panning

First round antibody phage were prepared as described in Example 4 using BS45 uracil template. Electroporations of mutagenesis DNA were performed yielding phage samples derived from different immunized mice. To create more diversity in the recombinant polyclonal library, each phage sample was panned separately.

Before the first round of functional panning with the biotinylated CDH17 antigen, antibody phage libraries were selected for phage displaying both heavy and light chains on their surface by panning with 7F11-magnetic latex (as described in Examples 21 and 22 of U.S. Pat. No. 6,555,310). Functional panning of these enriched libraries was performed in principle as described in Example 16 of U.S. Pat. No. 6,555,310. Specifically, 10 μL of $1*10^{-6}$ M biotinylated CDH17 antigen was added to the phage samples (approximately $1*10^{-8}$ M final concentration of the CDH17), and the mixture allowed to come to equilibrium overnight at 2-8° C.

After reaching equilibrium, samples were panned with avidin magnetic latex to capture antibody phage bound to the CDH17. Equilibrated avidin magnetic latex (Example 4), 200 μL latex per sample, was incubated with the phage for 10 min at room temperature. After 10 min, approximately 9 ml of panning buffer was added to each phage sample, and the magnetic latex separated from the solution using a magnet. After a ten minute separation, unbound phage was carefully removed using a 10 ml sterile pipette. The magnetic latex was then resuspended in 10 ml of panning buffer to begin the second wash. The latex was washed a total of three times as described above. For each wash, the tubes were in contact with the magnet for 10 min to separate unbound phage from the magnetic latex. After the third wash, the magnetic latex was resuspended in 1 ml of panning buffer and transferred to a 1.5 mL tube. The entire volume of magnetic latex for each sample was then collected and resuspended in 200 μl 2*YT and plated on 150 mm LB plates as described in Example 1 to amplify bound phage. Plates were incubated at 37° C. for 4 hr, then overnight at 20° C.

The 150 mm plates used to amplify bound phage were used to generate the next round of antibody phage. After the overnight incubation, second round antibody phage were eluted from the 150 mm plates by pipetting 10 mL of 2*YT media onto the lawn and gently shaking the plate at room temperature for 20 min. The phage samples were then transferred to 15 ml disposable sterile centrifuge tubes with a plug seal cap, and the debris from the LB plate pelleted by centrifuging the tubes for 15 min at 3500 rpm. The supernatant containing the second round antibody phage was then transferred to a new tube.

A second round of functional panning was set up by diluting 100 μL of each phage stock into 900 μL of panning buffer in 15 ml disposable sterile centrifuge tubes. The biotinylated CDH17 antigen was then added to each sample as described for the first round of panning, and the phage samples incubated for 1 hr at room temperature. The phage samples were then panned with avidin magnetic latex as described above. The progress of panning was monitored at this point by plating aliquots of each latex sample on 100 mm LB agar plates to determine the percentage of kappa positives. The majority of latex from each panning (99%) was plated on 150 mm LB agar plates to amplify the phage bound to the latex. The 100 mm LB agar plates were incubated at 37° C. for 6-7 hr, after which the plates were transferred to room temperature and nitrocellulose filters (pore size 0.45 mm, BA85 Protran, Schleicher and Schuell, Keene, N.H.) were overlaid onto the plaques.

Plates with nitrocellulose filters were incubated overnight at room temperature and then developed with a goat anti-mouse kappa alkaline phosphatase conjugate to determine the percentage of kappa positives as described below. Phage samples with lower percentages (<70%) of kappa positives in the population were subjected to a round of panning with 7F11-magnetic latex before performing a third functional round of panning overnight at 2-8° C. using the biotinylated CDH17 antigen at approximately $2*10^{-9}$ M. This round of panning was also monitored for kappa positives. Individual phage samples that had kappa positive percentages greater than 80% were pooled and subjected to a final round of panning overnight at 2-8° C. at $5*10^{-9}$ M. The CDH17 antibody genes contained within the eluted phage from this fourth round of functional panning were subcloned into the expression vector, pBRncoH3.

The subcloning process was done generally as described in Example 18 of U.S. Pat. No. 6,555,310. After subcloning, the expression vector was electroporated into DH10B cells and the mixture grown overnight in 2*YT containing 1% glycerol and 10 μg/ml tetracycline. After a second round of growth and selection in tetracycline, aliquots of cells were frozen at −80° C. as the source for the CDH17 polyclonal antibody production. Monoclonal antibodies were selected from these polyclonal mixtures by plating a sample of the mixture on LB agar plates containing 10 μg/ml tetracycline and screening for antibodies that recognized the CDH17.

Expression and Purification of Recombinant Antibodies Against Cadherin-17

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium [Pack et al. (1993) *BioTechnology* 11: 1271-1277] supplemented with 3 g/L L-leucine, 3 g/L L-isoleucine, 12 g/L casein digest (Difco, Detroit, Mich.), 12.5 g/L glycerol and 10 μg/ml tetracycline. The temperature, pH and dissolved oxygen in the fermentor were controlled at 26° C., 6.0-6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17,000 psi. The high pressure homogenization of the cells released the Fab into the culture supernatant.

The first step in purification was expanded bed immobilized metal affinity chromatography (EB-IMAC). Streamline™ chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% $NaN_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% $NaN_3$, pH 8.0. The Fab elution pool from the EB-IMAC step was diluted four-fold in 20 mM borate, 0.01% $NaN_3$, pH 8.0 and loaded onto the IEC column. After washing, the Fab was eluted with a 37.5-200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% $NaN_3$, pH 8.0 buffer for storage. This was achieved in a Sartocon Slice™ system fitted with a 10,000 MWCO cassette (Sartorius, Bohemia, N.Y.). The final purification yields were typically 50%. The concentration of the purified Fab was measured by UV absorbance at 280 nm, assuming an absorbance of 1.6 for a 1 mg/ml solution.

EXAMPLE 6

Specificity of Monoclonal Antibodies to CDH17 Determined by Flow Cytometry Analysis The specificity of antibodies against Cadherin-17 selected in Example 5 was tested by flow cytometry. To test the ability of the antibodies to bind to cell surface Cadherin-17 protein, the antibodies were incubated with Cadherin-17-expressing cells: LoVo and LS174T, human colorectal cancer lines. Cells were washed and resuspended in PBS. Four microliters of the suspensions were applied to wells of an eight well microscope slide and allowed to air dry. The slides were lightly heated to fix the smears to the slide and covered with 0.1 mg/ml of antibody diluted in PBS containing 1% BSA. The smears were incubated with antibody for 1 h at 37° C. in a moist chamber. After washing the slides three times by soaking in PBS for 5 min each, the smears were covered with fluorescein isothiocyanate conjugated rabbit anti-mouse IgG (H&L) F(ab')2 (Zymed Laboratories, Inc., South San Francisco, Calif.) diluted 1:80 in PBS, 1% BSA, 0.05% Evans Blue (Sigma). The slides were incubated for 1 h at 37° C. in a moist chamber then washed as described above. After a final wash in deionized water, the slides were allowed to air dry in the dark. Coverslips were mounted using a 90% glycerol mounting medium containing 10 mg/ml p-phenylenediamine, pH 8.0.

4. The results of the flow cytometry analysis demonstrated that 14 monoclonal antibodies designated CDH17_A1, CDH17_A2, CDH17_A3, CDH17_A4, CDH17_A5, CDH17_A6, CDH17_A7, CDH17_A8, CDH17_A9, CDH17_A10, CDH17_A11, CDH17_A12, CDH17_A13 and CDH17_A14 bind effectively to cell-surface human Cadherin-17.

EXAMPLE 7

Structural Characterization of Monoclonal Antibodies to Cadherin-17

The cDNA sequences encoding the heavy and light chain variable regions of the CDH17_A1, CDH17_A2, CDH17_A3, CDH17_A4, CDH17_A5, CDH17_A6, CDH17_A7, CDH17_A8, CDH17_A9, CDH17_A10, CDH17_A11, CDH17_A12, CDH17_A13 and CDH17_A14 monoclonal antibodies were obtained using standard PCR techniques and were sequenced using standard DNA sequencing techniques.

The antibody sequences may be mutagenized to revert back to germline residues at one or more residues.

The nucleotide and amino acid sequences of the light chain variable region of CDH17_A1 are SEQ ID NO: 54 and 30, respectively.

The nucleotide and amino acid sequences of the heavy chain variable region of CDH17_A1 are SEQ ID NO: 42 and 18, respectively.

The nucleotide and amino acid sequences of the light chain variable region of CDH17_A2 are SEQ ID NO: 55 and 31, respectively.

The nucleotide and amino acid sequences of the heavy chain variable region of CDH17_A2 are SEQ ID NO: 43 and 19, respectively.

The nucleotide and amino acid sequences of the light chain variable region of CDH17_A3 are SEQ ID NO: 55 and 31, respectively.

The nucleotide and amino acid sequences of the heavy chain variable region of CDH17_A3 are SEQ ID NO: 44 and 20, respectively.

The nucleotide and amino acid sequences of the light chain variable region of CDH17_A4 are SEQ ID NO: 56 and 32, respectively.

The nucleotide and amino acid sequences of the heavy chain variable region of CDH17_A4 are SEQ ID NO: 45 and 21, respectively.

The nucleotide and amino acid sequences of the light chain variable region of CDH17_A5 are SEQ ID NO: 57 and 33, respectively.

The nucleotide and amino acid sequences of the heavy chain variable region of CDH17_A5 are SEQ ID NO: 46 and 22, respectively.

The nucleotide and amino acid sequences of the light chain variable region of CDH17_A6 are SEQ ID NO: 58 and 34, respectively.

The nucleotide and amino acid sequences of the heavy chain variable region of CDH17_A6 are SEQ ID NO: 47 and 23, respectively.

The nucleotide and amino acid sequences of the light chain variable region of CDH17_A7 are SEQ ID NO: 59 and 35, respectively.

The nucleotide and amino acid sequences of the heavy chain variable region of CDH17_A7 are SEQ ID NO: 48 and 24, respectively.

The nucleotide and amino acid sequences of the light chain variable region of CDH17_A8 are SEQ ID NO: 60 and 36, respectively.

The nucleotide and amino acid sequences of the heavy chain variable region of CDH17_A8 are SEQ ID NO: 49 and 25, respectively.

The nucleotide and amino acid sequences of the light chain variable region of CDH17_A9 are SEQ ID NO: 61 and 37, respectively.

The nucleotide and amino acid sequences of the heavy chain variable region of CDH17_A9 are SEQ ID NO: 47 and 23, respectively.

The nucleotide and amino acid sequences of the light chain variable region of CDH17_A10 are SEQ ID NO: 62 and 38, respectively.

The nucleotide and amino acid sequences of the heavy chain variable region of CDH17_A10 are SEQ ID NO: 47 and 23, respectively.

The nucleotide and amino acid sequences of the light chain variable region of CDH17_A11 are SEQ ID NO: 63 and 39, respectively.

The nucleotide and amino acid sequences of the heavy chain variable region of CDH17_A11 are SEQ ID NO: 50 and 26, respectively.

The nucleotide and amino acid sequences of the light chain variable region of CDH17_A12 are SEQ ID NO: 64 and 38, respectively.

The nucleotide and amino acid sequences of the heavy chain variable region of CDH17_A12 are SEQ ID NO: 51 and 27, respectively.

The nucleotide and amino acid sequences of the light chain variable region of CDH17_A13 are SEQ ID NO: 65 and 40, respectively.

The nucleotide and amino acid sequences of the heavy chain variable region of CDH17_A13 are SEQ ID NO: 52 and 28, respectively.

The nucleotide and amino acid sequences of the light chain variable region of CDH17_A14 are SEQ ID NO: 66 and 41, respectively.

The nucleotide and amino acid sequences of the heavy chain variable region of CDH17_A14 are SEQ ID NO: 53 and 29, respectively.

EXAMPLE 8

Immunohistochemistry on FFPE Sections Using Anti-Cadherin-17 Antibodies

Immunohistochemistry was performed on FFPE sections of colorectal tumor and normal adjacent tissue using the anti-Cadherin-17 antibodies CDH17_A3, CDH17_A4, CDH17_A6, CDH17_A8 and CDH17_A9.

EX-De-Wax was from BioGenex, CA, USA. Tissue sections and arrays were from Biomax, MD, USA. Slides were heated for 2 h at 60° C. in 50 ml Falcons in a water bath with no buffer. Each Falcon had one slide or two slides back-to back with long gel loading tip between them to prevent slides from sticking to each other. Slides were deparaffinised in EZ-DeWax for 5 min in black slide rack, then rinsed well with the same DeWax solution using 1 ml pipette, then washed with water from the wash bottle. Slides were placed in a coplin jar filled with water until the pressure cooker was ready; the water was changed a couple of times. Water was exchanged for antigen retrieval solution=1× citrate buffer, pH 6 (DAKO). Antigen was retrieved by the pressure cooker method. The slides in the plastic coplin jar in antigen retrieval solution were placed into a pressure cooker which was then heated up to position 6 (the highest setting). 15-20 min into the incubation, the temperature was reduced to position 3 and left at that (when the temperature inside the pressure cooker was 117° C.) for another 20-25 minutes. Then the hob was switched off and the cooker was placed onto the cold hob and the pressure was released by carefully moving the handle into the position between "open" and "closed". The whole system was left to release the pressure and to cool down for another 20 minutes. The lid was opened and samples taken out to rest on the bench. The slides were washed 1×5 min with PBS-3T (0.5 L PBS+3 drops of Tween-20) and placed in PBS.

After antigen retrieval, slides were mounted in the Shandon Coverplate system. Trapping of air bubbles between the slide and plastic coverplate was prevented by placing the coverplate into the coplin jar filled with PBS and gently sliding the slide with tissue sections into the coverplate. The slide was pulled out of the coplin jar while holding it tightly together with the coverplate. The assembled slide was placed into the rack, letting PBS trapped in the funnel and between the slide and coverplate to run through. Slides were washed with 2×2 ml (or 4×1 ml) PBS-3T, 1×2 ml PBS, waiting until all PBS had gone through the slide and virtually no PBS was left in the funnel.

Endogenous peroxide blockade was performed using 1-4 drops of peroxide solution per slide; the incubation time was 5 minutes. The slides were rinsed with water and then once with 2 ml PBS-3T and once with 2 ml PBS; it was important to wait until virtually no liquid was left in the funnel before adding a new portion of wash buffer.

The primary antibody was diluted with an Antibody diluent reagent (DAKO). Optimal dilution was determined to be 1:400. Up to 200 µl of diluted primary antibody was applied to each slide and incubated for 45 minutes at room temperature. Slides were washed with 2×2 ml (or 4×1 ml) PBS-3T and then 1×2 ml PBS.

The goat anti-mouse kappa HRP secondary (1 mg/ml, cat.1050-05, Southern Biotech) was applied 2×2 drops per slide and incubated for 35 min at room temperature. The slides were washed as above.

The DAB substrate was made up in dilution buffer; 2 ml containing 2 drops of substrate was enough for 10 slides. The DAB reagent was applied to the slides by applying a few drops at a time and left for 10 min. The slides were washed 1×2 ml (or 2×1 ml) with PBS-3T and 1×2 ml (or 2×1 ml) with PBS.

Hematoxylin (DAKO) was applied; 1 ml was enough for 10 slides and slides were incubated for 1 min at room temperature. The funnels of the Shandon Coverplate system were filled with 2 ml of water and let to run through. When slides were clear of the excess of hematoxylin, the system was disassembled, tissue sections and/or arrays were washed with water from the wash bottle and placed into black slide rack. Tissues were dehydrated by incubating in EZ-DeWax for 5 min and then in 95% ethanol for 2-5 min.

Slides were left to dry on the bench at room temperature and then mounted in mounting media and covered with coverslip.

Immunohistochemical analysis on antibodies CDH17_A3, CDH17_A4, CDH17_A6, CDH17_A8 and CDH17_A9 revealed specific membrane staining of tumor cells in colorectal cancer and no appreciable staining of normal adjacent tissue in all cases. Antibody CDH17_A4, in particular, showed clear specific membrane staining of tumor cells.

EXAMPLE 9

Immunohistochemistry on Frozen Sections Using Anti-Cadherin-17 Antibodies

Immunohistochemistry was performed on frozen paired tumor and normal adjacent tissues using the anti-Cadherin-17 antibodies CDH17_A4, CDH17_A6, CDH17_A8 and CDH17_A9.

Tissue sections were from BioChain Institute Inc., CA, USA.

Frozen sections were washed with PBS twice for 3 minutes each and were then placed in PBS.

Endogenous peroxide blockade was performed using Peroxidase Blocker (S2001, DAKO). 1-4 drops of peroxidase blocker was added to each slide and incubated for 5 minutes. The slides were rinsed three times with 3 ml PBS.

The primary antibody was diluted with an Antibody diluent reagent (DAKO). 150 µl of diluted primary antibody was applied to each slide and incubated for 45 minutes at room temperature. Slides were washed with twice for 3 minutes with PBS-3T (500 ml PBS+3 drops of Tween-20) and then once for 3 minutes with PBS.

The goat anti-mouse kappa HRP secondary was applied at 1:1000 (1 mg/ml, cat. 1050-05, Southern Biotech) and incubated for 35 min at room temperature. The slides were washed as above.

The DAB substrate was made up in dilution buffer; 2 ml containing 2 drops of substrate was enough for 10 slides. The DAB reagent was applied to the slides by applying a few drops at a time and incubated for 10 min. The slides were washed once for 3 minutes with PBS-3T and twice for 3 minutes with water.

Hematoxylin (DAKO) was applied; 1 ml was enough for 10 slides and slides were incubated for 1 min at room temperature.

Slides were left to dry on the bench at room temperature and then mounted in water-based mounting media from Vector and covered with coverslip.

Immunohistochemical analysis on antibodies CDH17_A4, CDH17_A6, CDH17_A8 and CDH17_A9 on three colorectal cancer samples along with the paired normal adjacent tissue samples revealed strong specific membrane staining of tumor cells in colorectal cancer and some weak staining of normal adjacent tissue. Antibody CDH17_A4, in particular, showed clear specific membrane staining of tumor cells.

EXAMPLE 10

Internalization and MABZAP of CDH17_A4 in LS174T and LoVo Cells

CDH17_A4 was shown to be internalized by LoVo cells upon binding to the cells using a Immunofluorescence microscopy assay. The Immunofluorescence microscopy assay showed internalization of the anti-Cadherin-17 monoclonal antibodies through binding of an anti-human IgG secondary antibody conjugated to Fluorescein isothiocyanate (GamK-FITC). First, CDH17_A4 were bound to the surface of the LoVo cells. Then, the secondary antibody conjugated to Fluorescein isothiocyanate were bound to the primary antibodies. Next, the CDH17_A4/secondary antibody FITC conjugate complex was internalized by the cells.

The Immunofluorescence microscopy assay was conducted as follows. LoVo cell were incubated at 37° C. for 12 hours for cells to adhere to each other. CDH17_A4 and secondary antibody conjugated to Fluorescein isothiocyanate were serially diluted, washed with FACS buffer (PBS, 2% FBS) and then added to the culture media. The media was then washed again with FACS buffer (PBS, 2% FBS) and incubated at 37%, after which 200 ul 2% PFA was added. Coverslips were mounted using a 9 ul aqueous mountaing media and the cells were then visualized at regular time intervals using Leica fluorescent microscope.

The monoclonal antibody, CDH17_A4, was shown to be internalized by LS147T and LoVo cells upon binding to the cells using a MabZap assay. The MabZAP assay showed internalization of the anti-CDH17 monoclonal antibodies through binding of an anti-human IgG secondary antibody conjugated to the toxin saporin. (Advanced Targeting System, San Diego, Calif., IT-22-100). First, CDH17_A4 was bound to the surface of the LS147T and LoVo cells. Then, the MabZAP antibodies were bound to the primary antibodies. Next, the MabZAP complex was internalized by the cells. The entrance of Saporin into the cells resulted in protein synthesis inhibition and eventual cell death.

The MabZAP assay was conducted as follows. Each of the cells was seeded at a density of 5×103 cells per well. The anti-CDH17 monoclonal antibodies or an isotype control human IgG were serially diluted then added to the cells. The MabZAP was then added at a concentration of 50 µg/ml and the plates allowed too incubate for 48 and 72 hours. Cell viability in the plates was detected by CellTiter-Glo® Luminescent Cell Viability Assay kit (Promega, G7571) and the plates were read at 490nM by a Luminomitor (Tuner BioSystems, Sunnyvale, Calif.). The data was analyzed by Prism (Graphpad). Cell death was proportional to the concentration of CDH17_A4 and monoclonal antibody. FIGS. 6A, 6B, 6C, 6D, 7A and 7B show that the anti-CDH17 monoclonal antibodies were efficiently internalized by LS174T and LoVo cells respectively as compared to the anti-human IgG isotype control antibody.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A method of treating colorectal cancer comprising administering to a subject an antibody capable of immunospecific binding to Cadherin-17, or a fragment or derivative thereof which comprises the binding domain of the antibody, wherein the antibody or fragment or derivative thereof contains or is conjugated to a therapeutic moiety.

2. A method as claimed in claim 1, wherein the antibody is selected from the group consisting of polyclonal, monoclonal, bispecific, humanized, chimeric and single chain antibodies; or where the fragment is selected from the group consisting of a Fab fragment and a F(ab')$_2$ fragment.

3. A method as claimed in claim 2, wherein the antibody is a monoclonal antibody.

* * * * *